(12) United States Patent
Tanetani et al.

(10) Patent No.: US 11,198,710 B2
(45) Date of Patent: Dec. 14, 2021

(54) TRANSGENIC PLANT HAVING HERBICIDE RESISTANCE

(71) Applicant: KUMIAI CHEMICAL INDUSTRY CO., LTD., Tokyo (JP)

(72) Inventors: Yoshitaka Tanetani, Tokyo (JP); Kiyoshi Kawai, Tokyo (JP)

(73) Assignee: KUMIAI CHEMICAL INDUSTRY CO., LTD., Tokyo (JP)

( * ) Notice: Subject to any disclaimer, the term of this patent is extended or adjusted under 35 U.S.C. 154(b) by 0 days.

(21) Appl. No.: 16/312,883

(22) PCT Filed: Jul. 4, 2017

(86) PCT No.: PCT/JP2017/024421
§ 371 (c)(1),
(2) Date: Dec. 21, 2018

(87) PCT Pub. No.: WO2018/008617
PCT Pub. Date: Jan. 11, 2018

(65) Prior Publication Data
US 2019/0263874 A1  Aug. 29, 2019

(30) Foreign Application Priority Data
Jul. 4, 2016 (JP) .............................. JP2016-132689

(51) Int. Cl.
C12N 15/82    (2006.01)
A01N 43/80    (2006.01)
C07K 14/415   (2006.01)

(52) U.S. Cl.
CPC ............ *C07K 14/415* (2013.01); *A01N 43/80* (2013.01); *C12N 15/8274* (2013.01); *C12Y 205/01018* (2013.01)

(58) Field of Classification Search
None
See application file for complete search history.

(56) References Cited

U.S. PATENT DOCUMENTS 6,730,828 B1 *   5/2004   Cole ..................... C12N 9/1088
                                                            435/252.3

FOREIGN PATENT DOCUMENTS

WO    WO99/14337    *  3/1999
WO    WO 99/14337  A2   3/1999

OTHER PUBLICATIONS

Tidemann, Breanne Darlene, Master of Science in Plant Science, University of Alberta, 2014 (Year: 2014).*
Walsh et al, Weed Technology, 2011, vol. 25, pp. 30-37 (Year: 2011).*
Tanetani et al. (2013) J Pestic Sci 38(3): 152-56.*
B.D. Tidemann (2014) Masters Thesis, Univ. Alta.*
Malcolm (2017) Agribusiness Perspectives on Transgenic Wheat. In: Bhalla P., Singh M. (eds) Wheat Biotechnology. Methods in Molecular Biology, vol. 1679. Humana Press, New York, NY.*
Walsh et al. (2011) Weed Tech 25:30-37.*
Boyland et al., "The Role of Glutathione and Glutathione S-Transferases in Mercapturic Acid Biosynthesis", Advances in Enzymology and Related Areas of Molecular Biology, vol. 32, 1969, p. 173-219.
Cummins et al., "A role for glutathione transferases functioning as glutathione peroxidases in resistance to multiple herbicides in black-grass", The Plant Journal, vol. 18, No. 3, 1999, p. 285-292.
Cummins et al., "Cloning, characterization and regulation of a family of phi class glutathione transferases from wheat", Plant Molecular Biology, vol. 52, 2003, p. 591-603.
Dixon et al., "Plant glutathione transferases", Genome Biology, vol. 3, No. 3, 2002, p. 1-10.
Edwards et al., "Plant Glutathione Transferases", Methods in Enzymology, vol. 401, 2005, p. 169-186.
Hatton et al., "Glutathione Transferase Activities and Herbicide Selectivity in Maize and Associated Weed Species", Pesticide Science, vol. 46, 1996, p. 267-275.
International Search Report for PCT/JP2017/024421 (PCT/ISA/210) dated Sep. 19, 2018.
Karavangeli et al., "Development of transgenic tobacco plants overexpressing maize glutathione S-transferase I for chloroacetanilide herbicides phytoremediation", Biomolecular Engineering, vol. 22, 2005, p. 121-128.
Lamoureux et al., "Metabolism of 2-Chloro-N-Isopropylacetanilide (Propachlor) in the Leaves of Corn, Sorghum, Sugarcane, and Barley", Journal of Agricultural and Food Chemistry, vol. 19, No. 2, 1971, p. 346-350.
Leavitt et al., "In Vitro Conjugation of Glutathione and Other Thiols with Acetanilide Herbicides and EPTC Sulfoxide and the Action of the Herbicide Antidote R-25788", Journal of Agricultural and Food Chemistry, vol. 27, No. 3, 1979, p. 533-536.
Mannervik, "The Isoenzymes of Glutathione Transferase", Advances in Enzymology and Related Areas of Molecular Biology, vol. 57, 1985, p. 357-417.
Mozer et al., "Purification and Characterization of Corn Glutathione S-Transferase", Biochemistry, vol. 22, 1983, p. 1068-1072.
Roxas et al., "Stress Tolerance in Transgenic Tobacco Seedlings that Overexpress Glutathione S-Transferase/Glutathione Peroxidase", Plant and Cell Physiology, vol. 41, No. 11, 2000, p. 1229-1234.
Tanetani et al., "Action mechanism of a novel herbicide, pyroxasulfone", Pesticide Biochemistry and Physiology, vol. 95, 2009, p. 47-55.

(Continued)

*Primary Examiner* — Russell T Boggs
(74) *Attorney, Agent, or Firm* — Birch, Stewart, Kolasch & Birch, LLP.

(57) ABSTRACT

The invention is intended to identify glutathione-S-transferase that exhibits the activities to metabolize and detoxify an isoxazoline derivative, such as pyroxasulfone. The invention provides a method for cultivating a transgenic plant into which a nucleic acid encoding a protein (a or b) below has been introduced in the presence of isoxazoline derivatives:
(a) a protein comprising the amino acid sequence as shown in SEQ ID NO: 2; or
(b) a protein comprising an amino acid sequence having 80% or higher identity to the amino acid sequence as shown in SEQ ID NO: 2 and having the activity of glutathione-S-transferase.

21 Claims, 49 Drawing Sheets
Specification includes a Sequence Listing.

(56) References Cited

OTHER PUBLICATIONS

Tanetani et al., "Role of metabolism in the selectivity of a herbicide, pyroxasulfone, between wheat and rigid ryegrass seedlings", Journal of Pesticide Science, vol. 38, No. 3, Jan. 2013, p. 152-156.
Tanetani et al., "Studies on the inhibition of plant very-long-chain fatty acid elongase by a novel herbicide, pyroxasulfone", Journal of Pesticide Science, vol. 36, No. 2, p. 221-228, 2011.
Written Opinion of the International Searching Authority for PCT/JP2017/024421 (PCT/ISA/237) dated Sep. 19, 2018.
Partial Supplementary European Search Report for European Application No. 17824220.2, dated Jan. 13, 2020.
Chinese Office Action issued in Application No. 201780054166.3 dated Jul. 20, 2021.
Lei et al., "Function, Application, Cloning and Expression of Glutathione S-transferases", Envronmental Science & Technology, vol. 32, No. 12, Dec. 2009, pp. 85-91.

\* cited by examiner

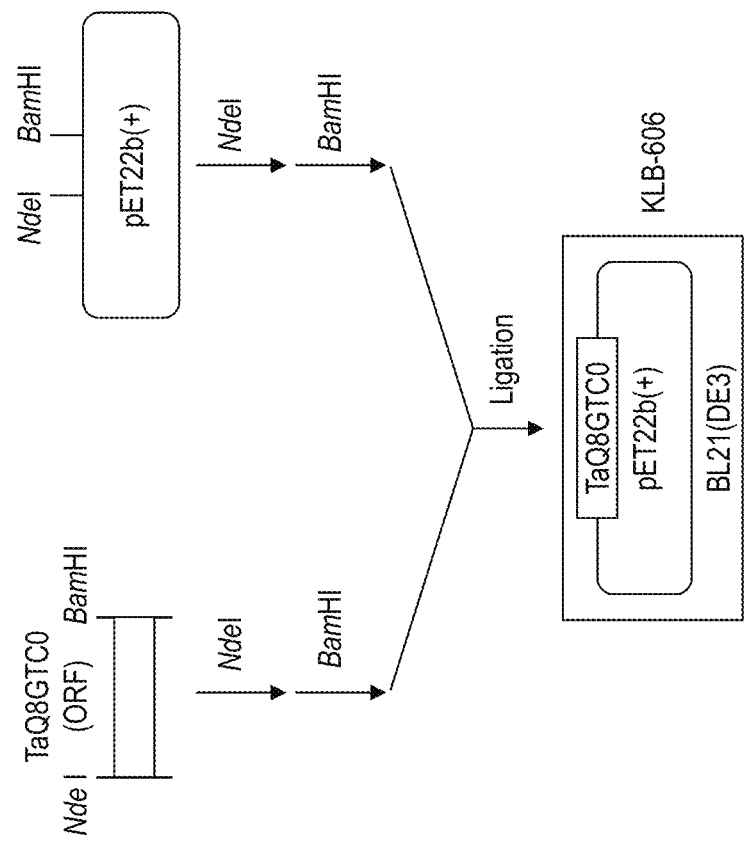
[Fig. 1]

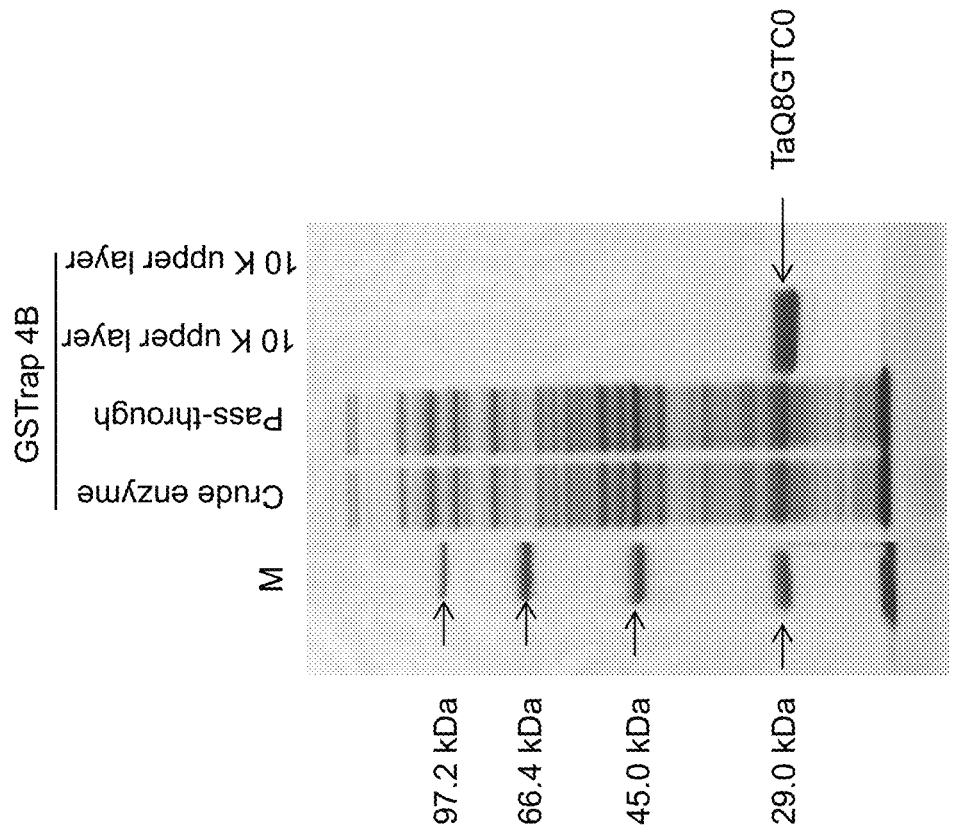
[Fig. 2]

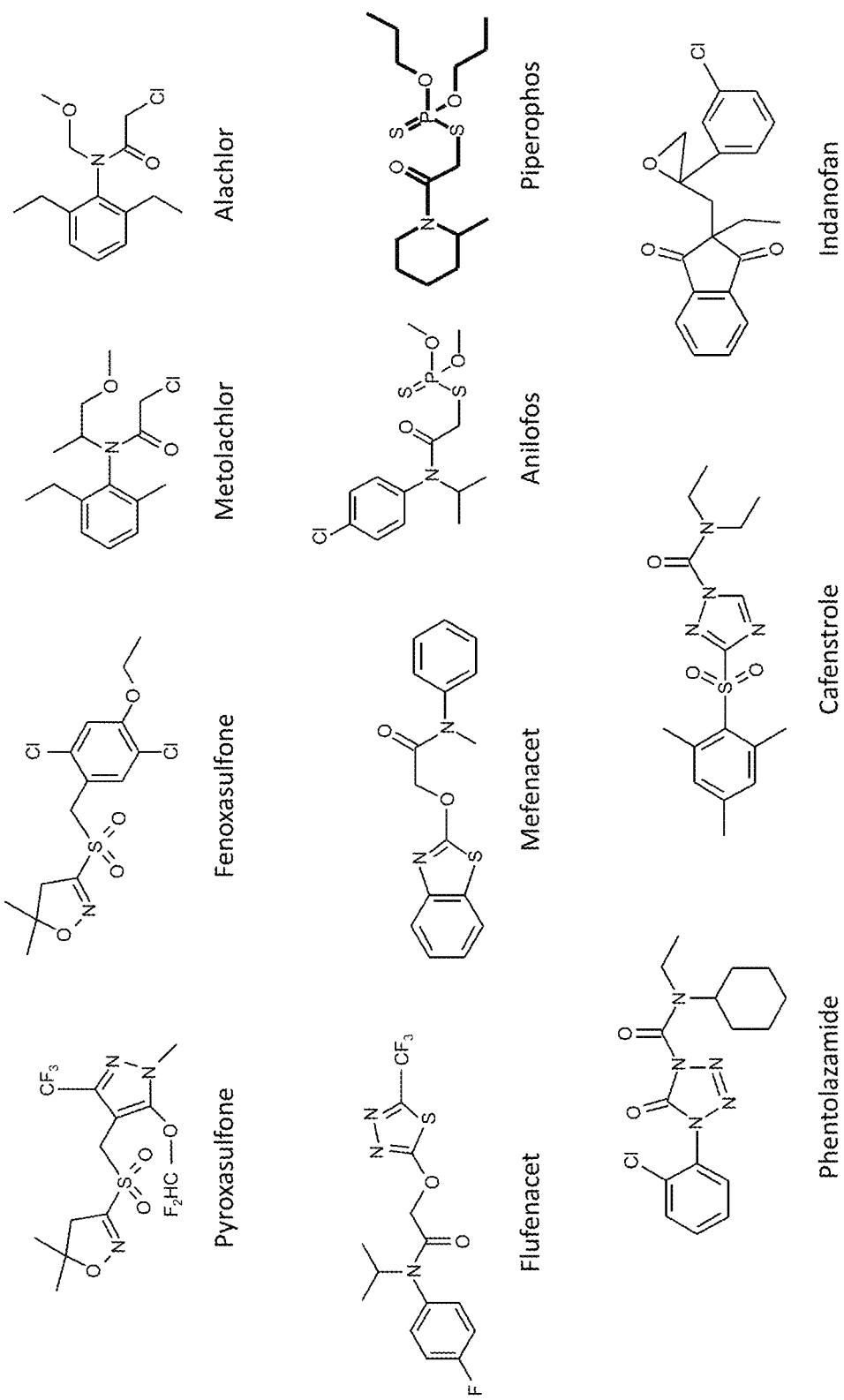
[Fig. 3]

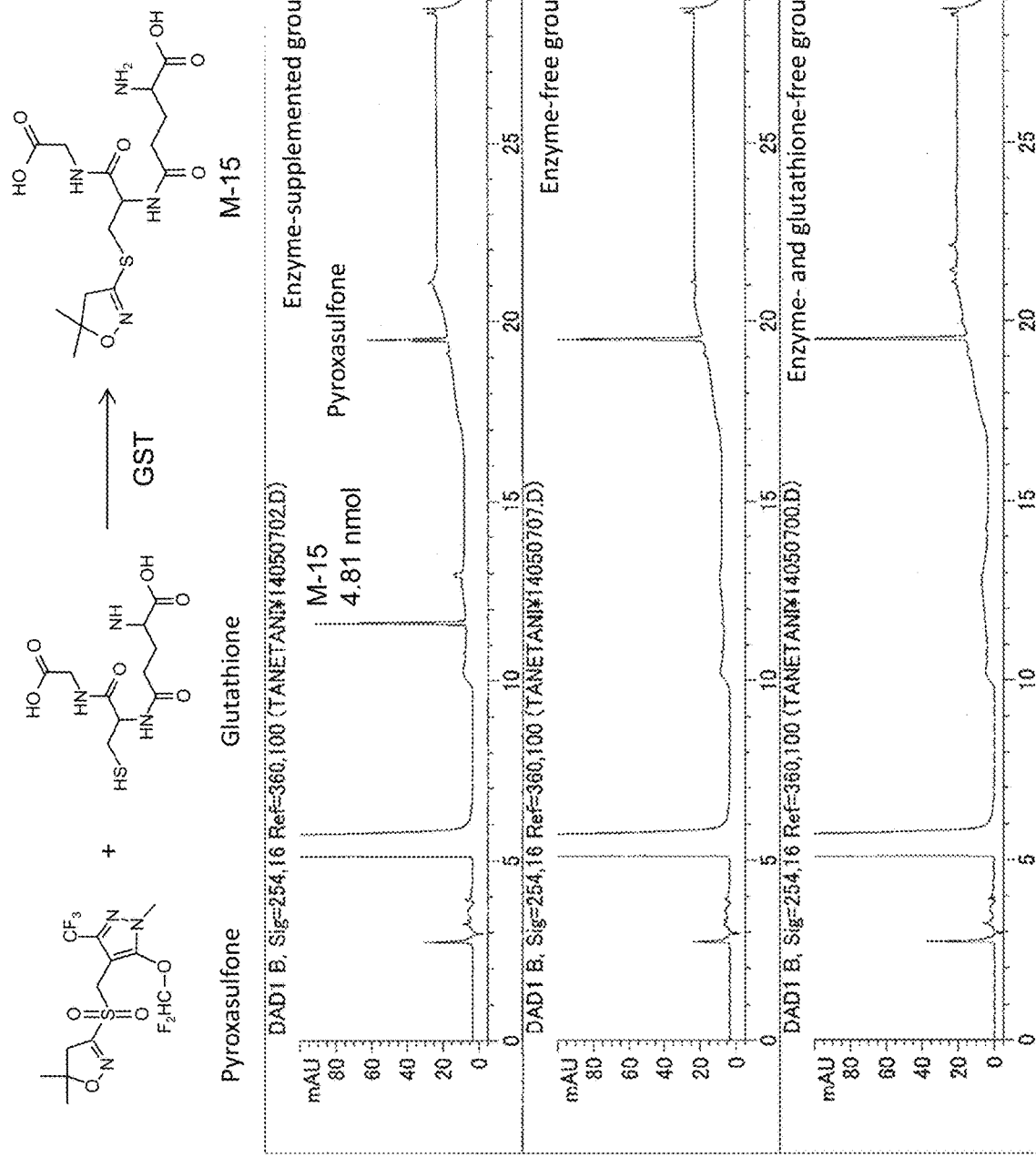
[Fig. 4]

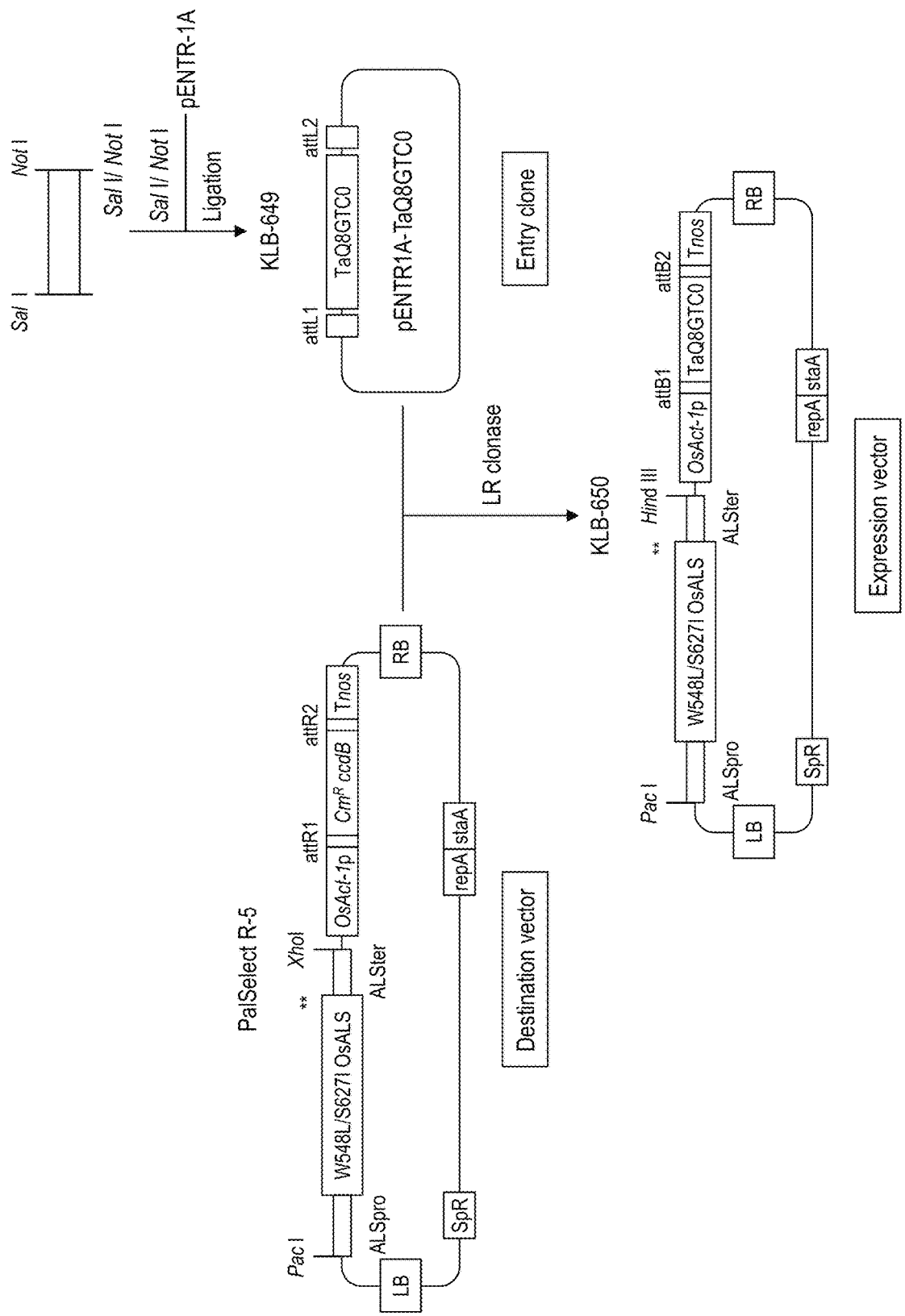
[Fig. 5]

[Fig. 6]
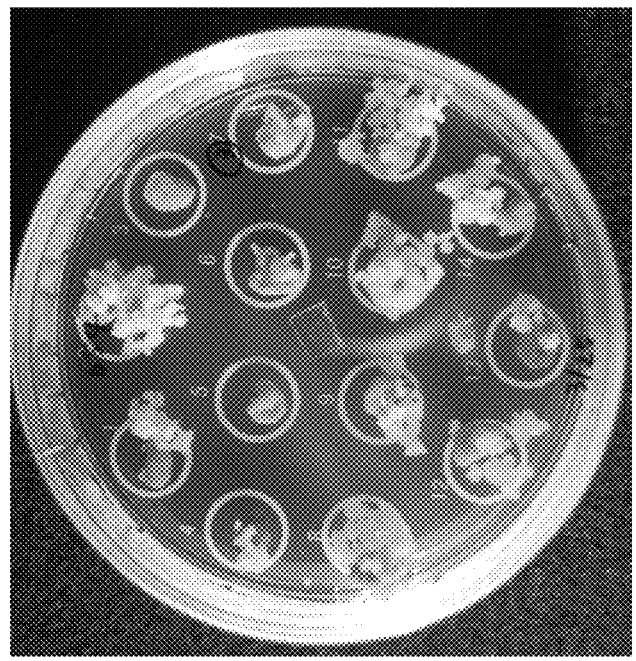
TaQ8GTC0
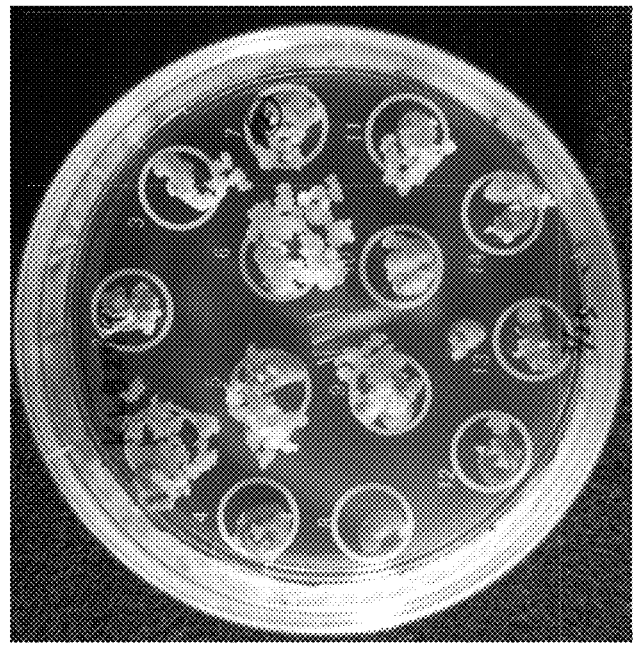
KLB-279

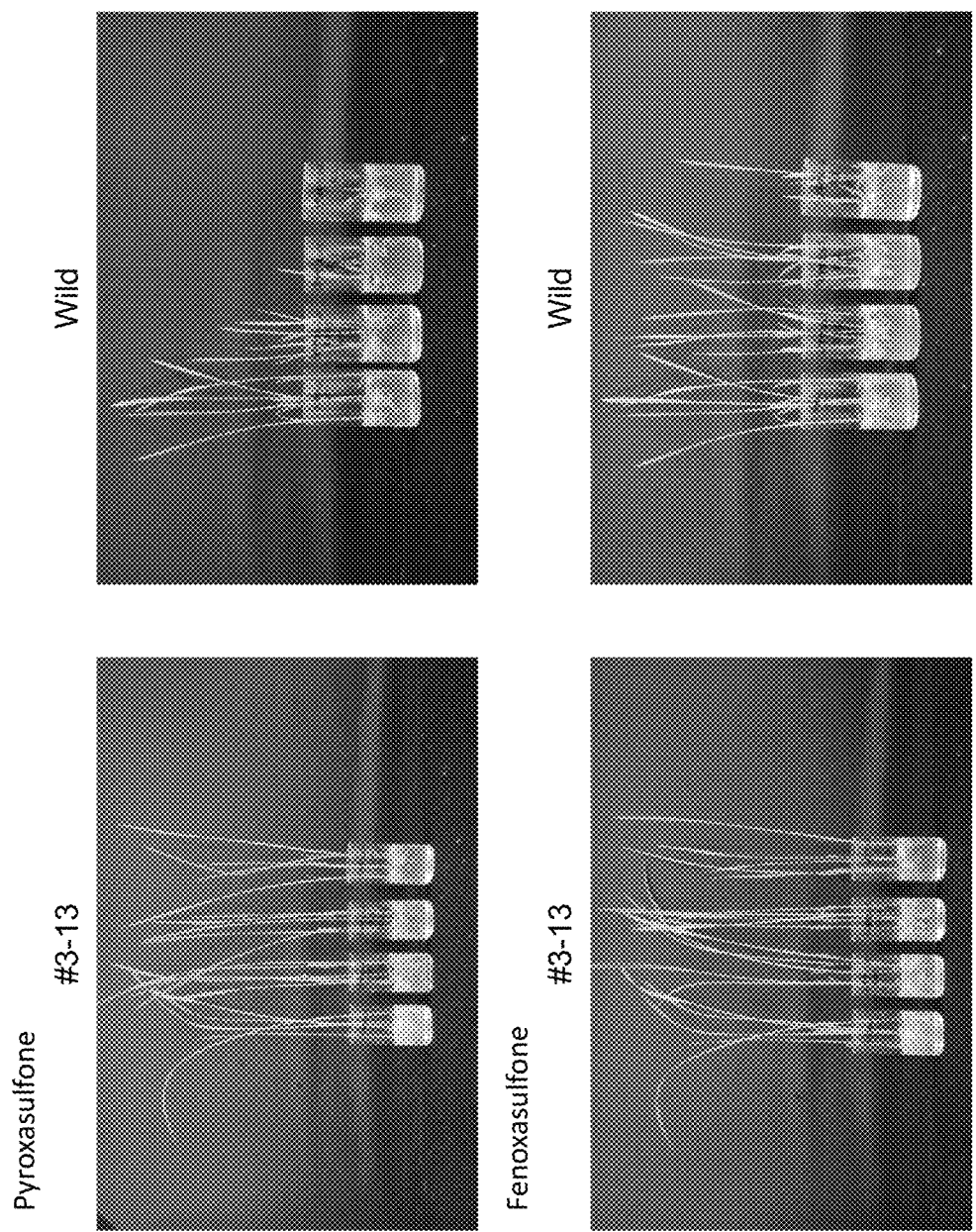
[Fig. 7-1]

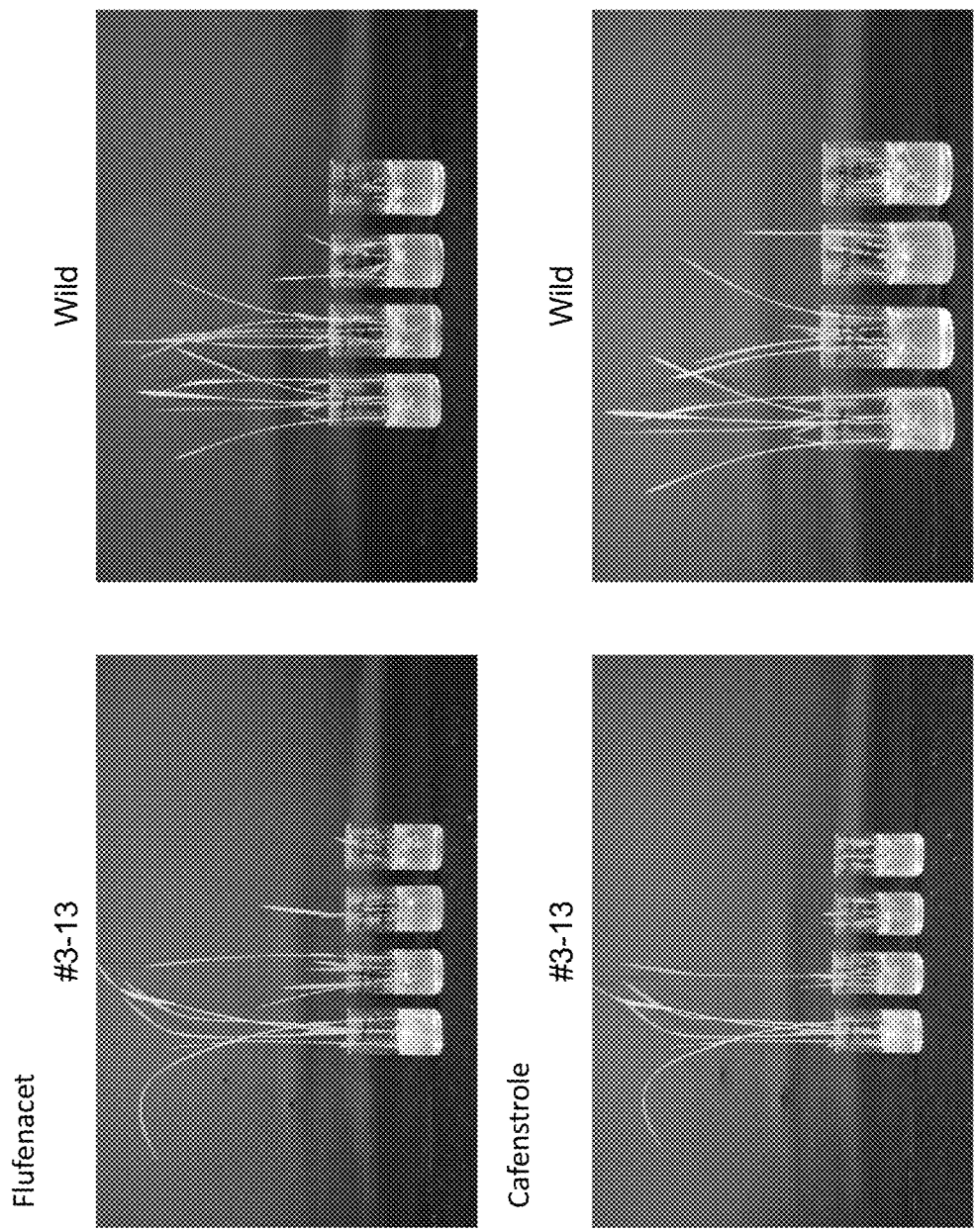
[Fig. 7-2]

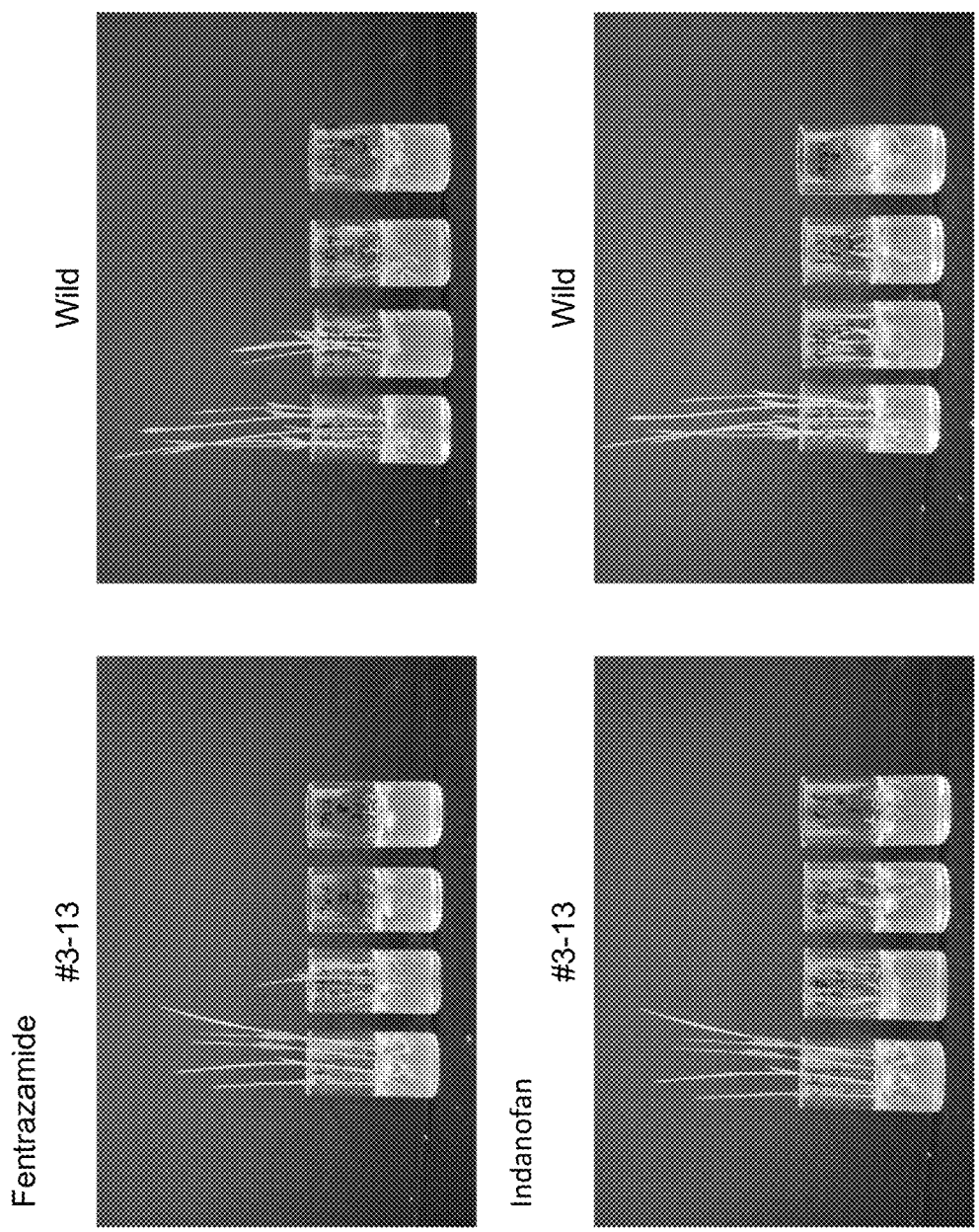
[Fig. 7-3]

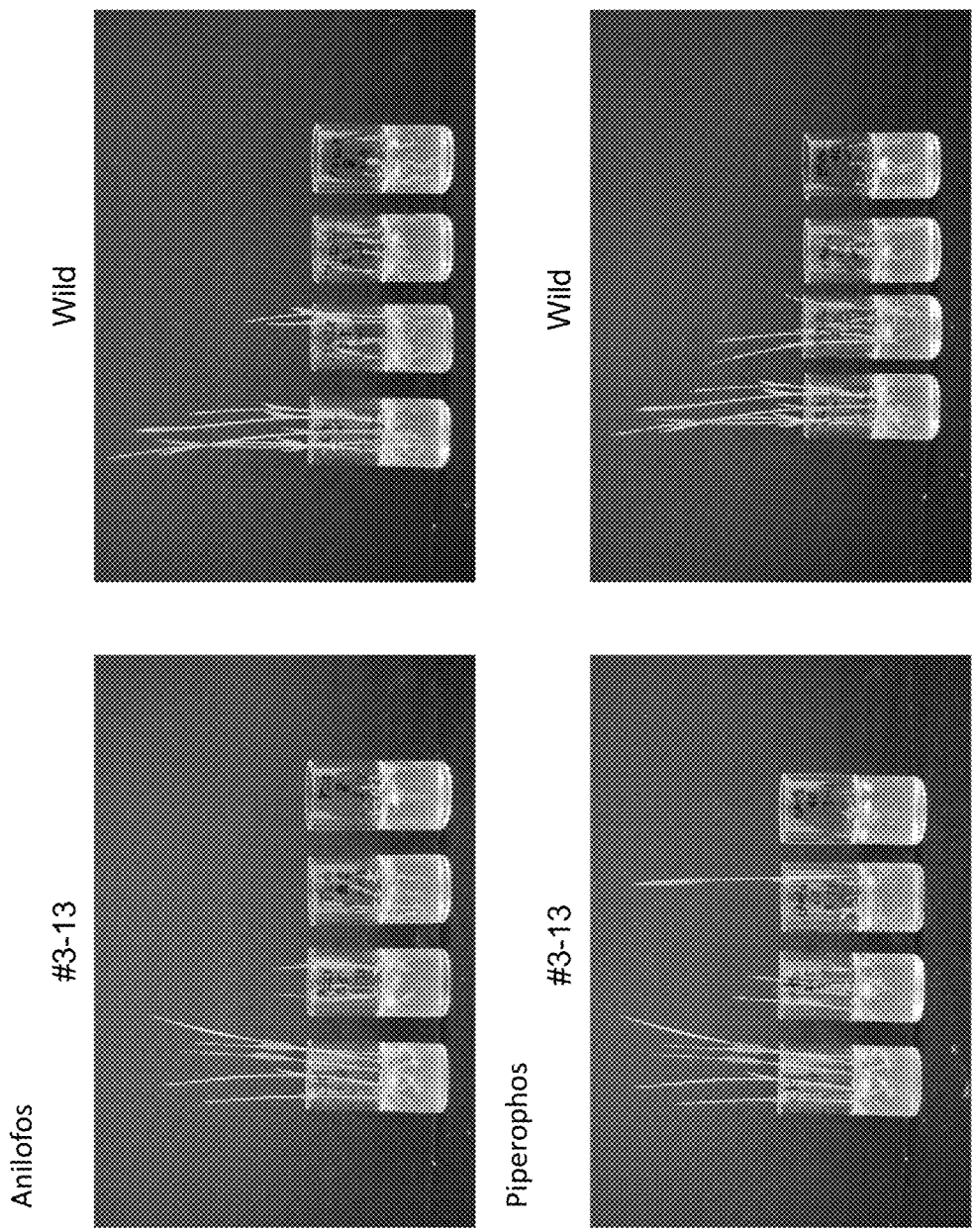
[Fig. 7-4]

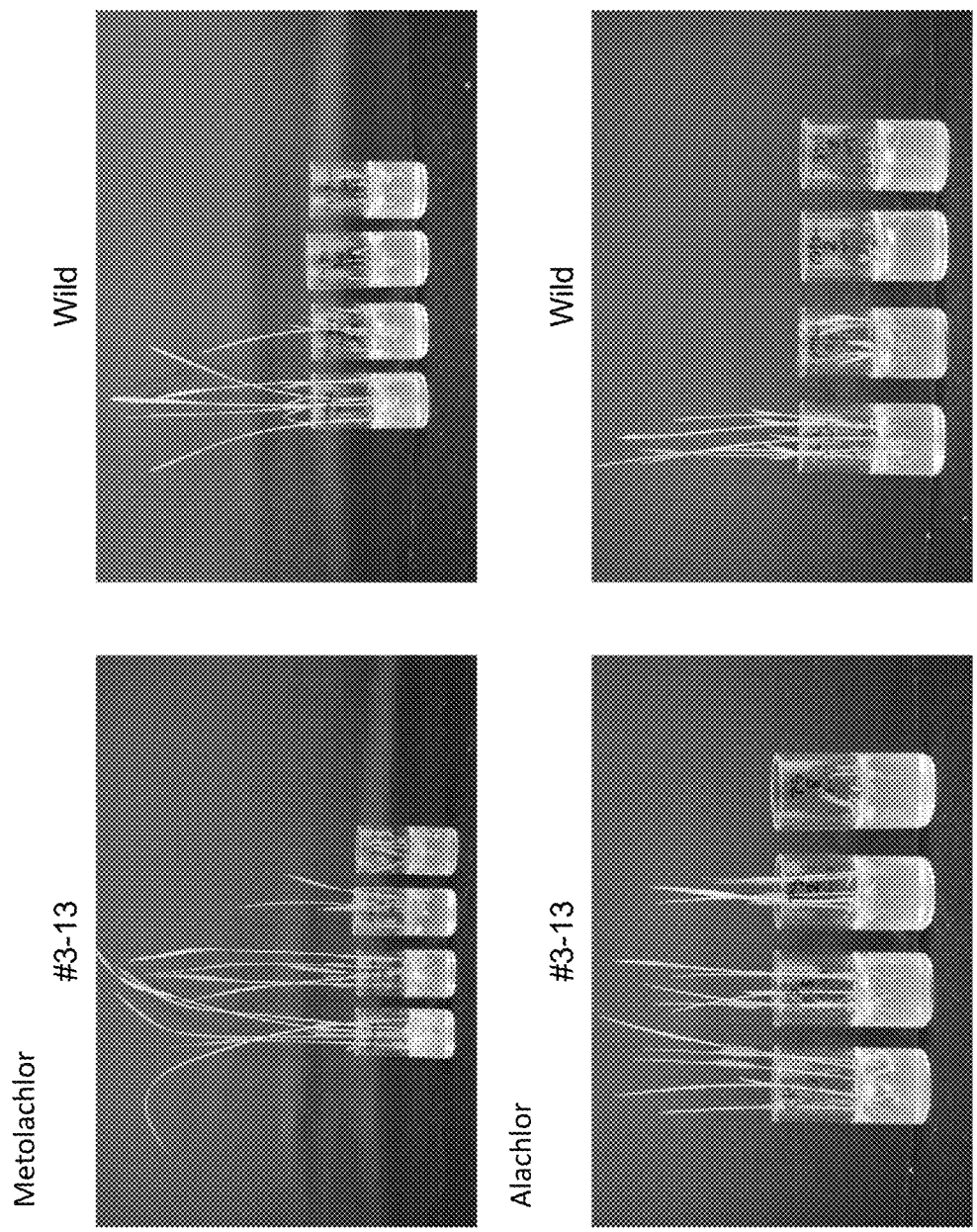
[Fig. 7-5]

[Fig. 7-6]
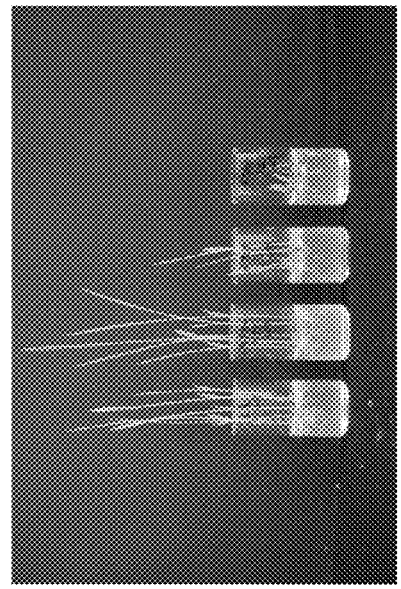
Wild
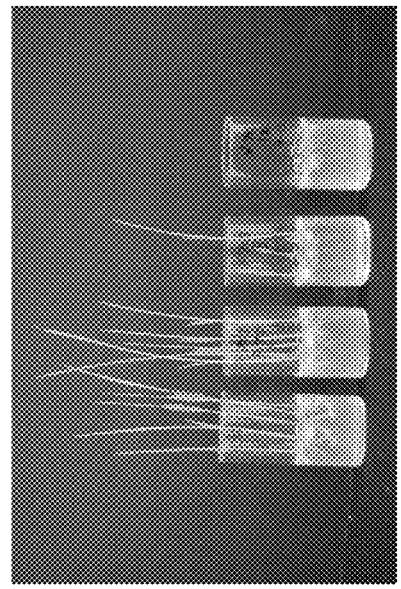
Mefenacet #3-13

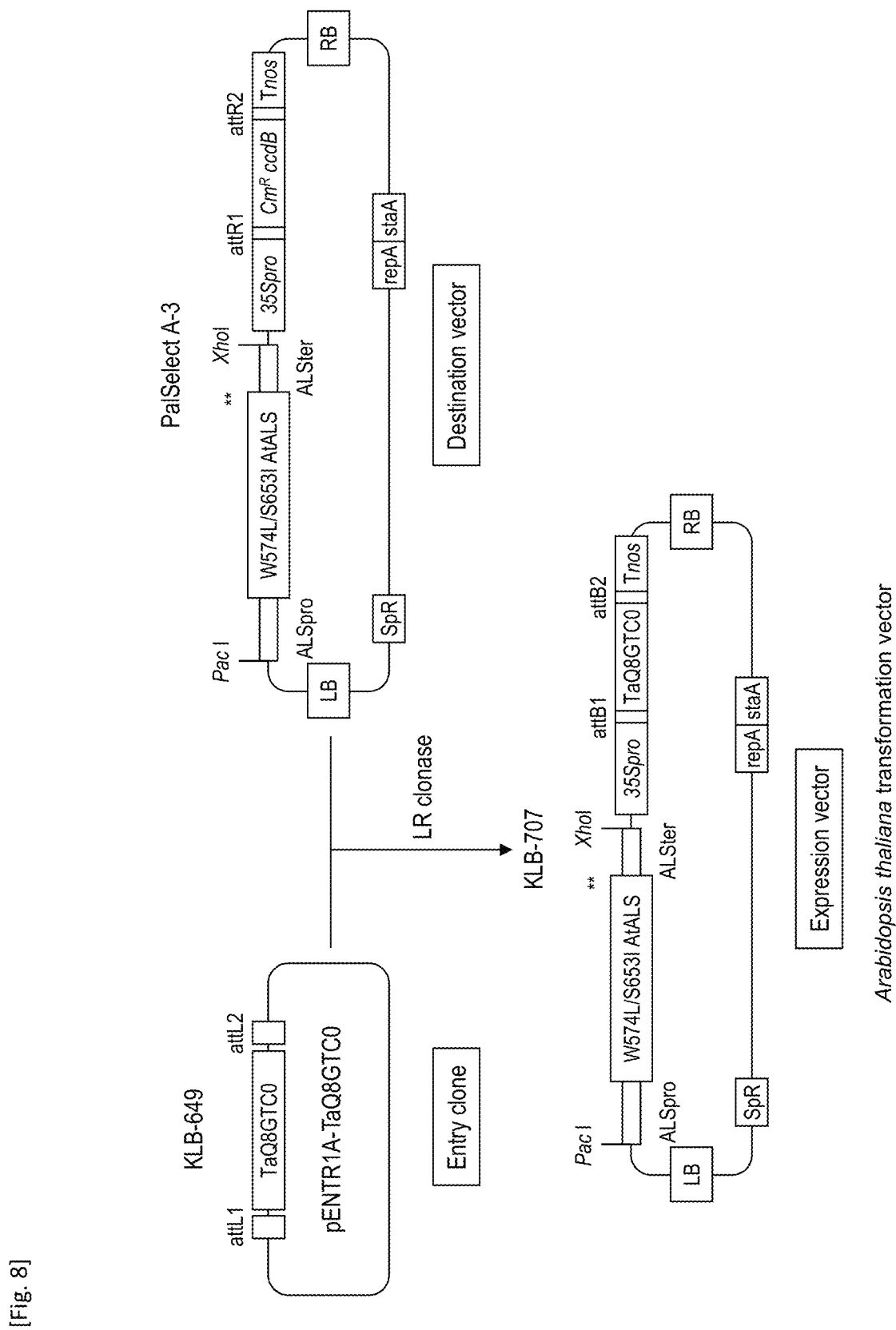
[Fig. 8]

[Fig. 9]
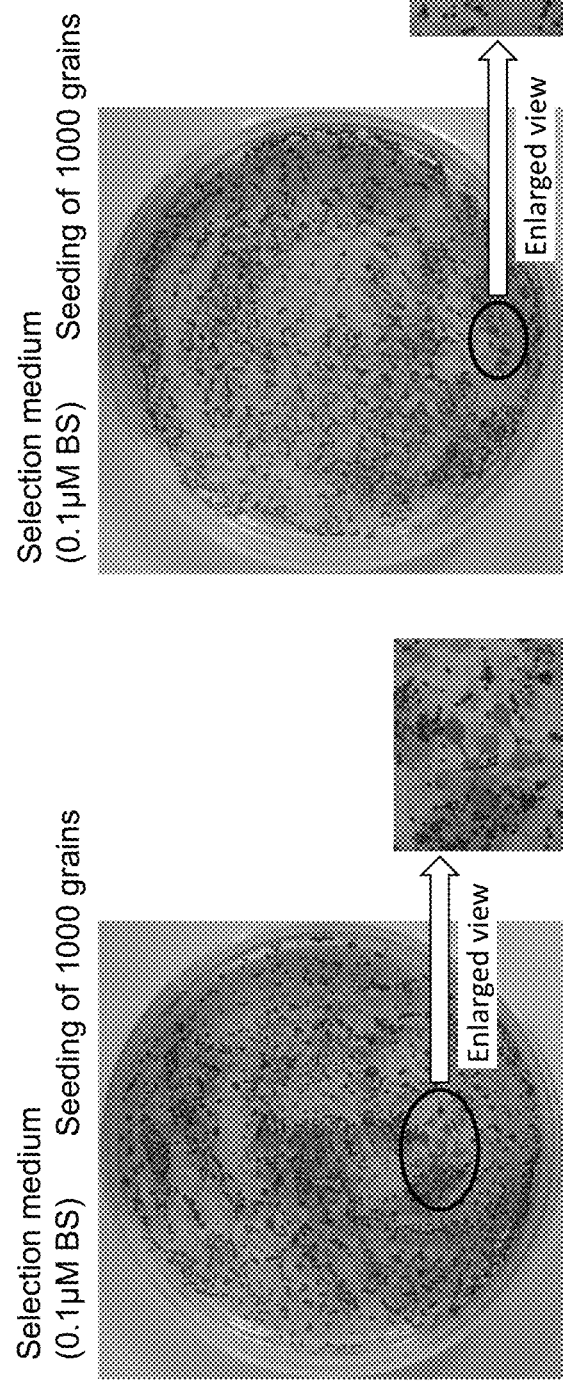

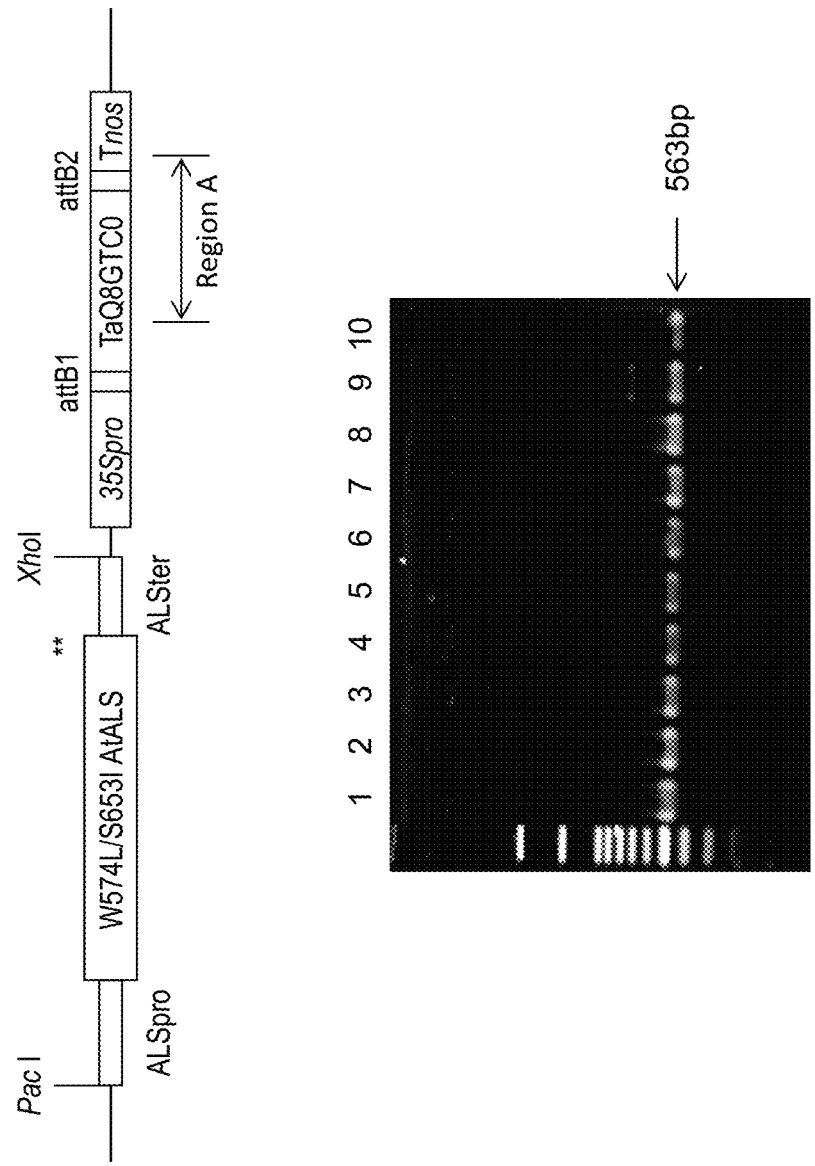
[Fig. 10]

[Fig. 11]
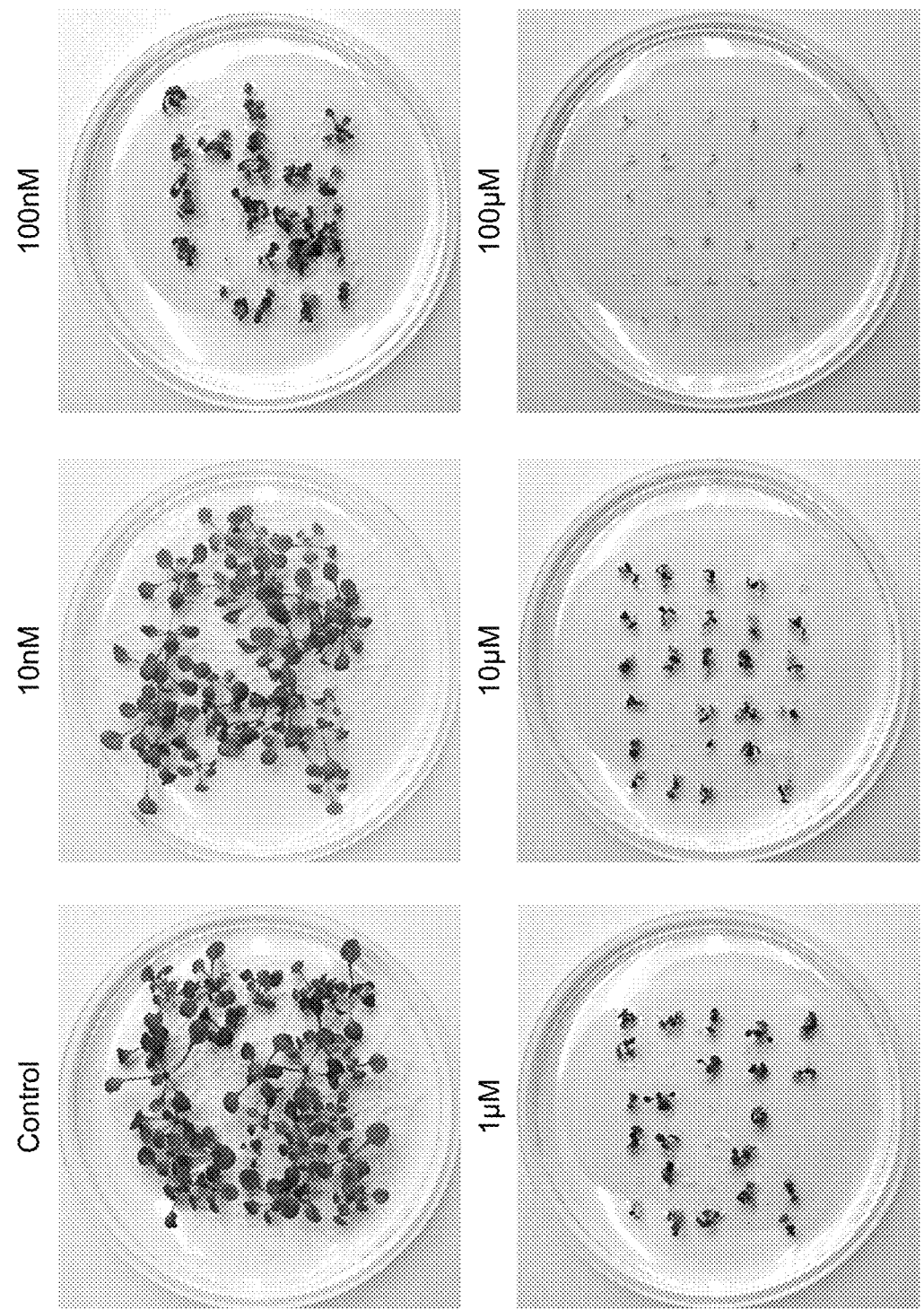

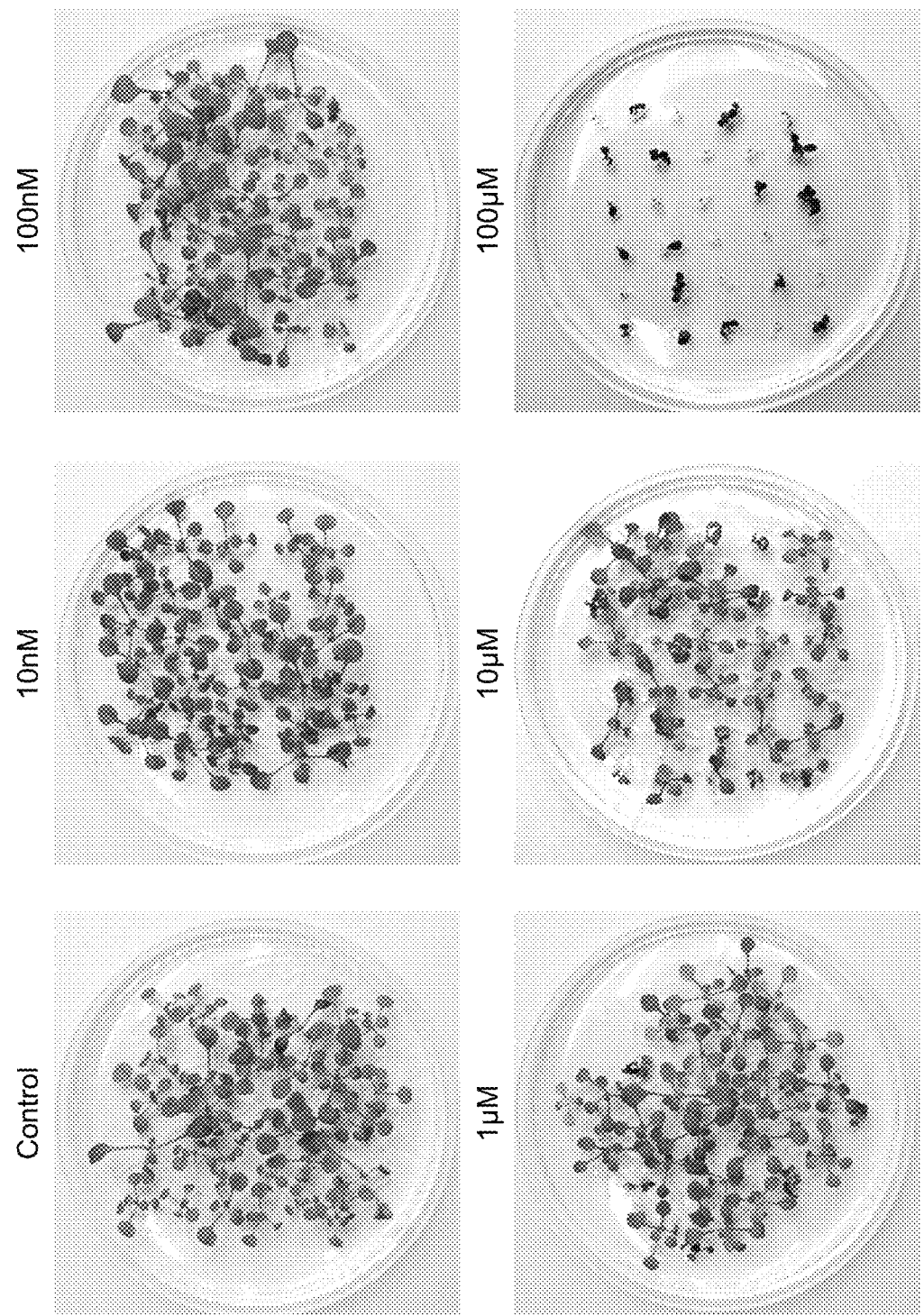
[Fig. 12]

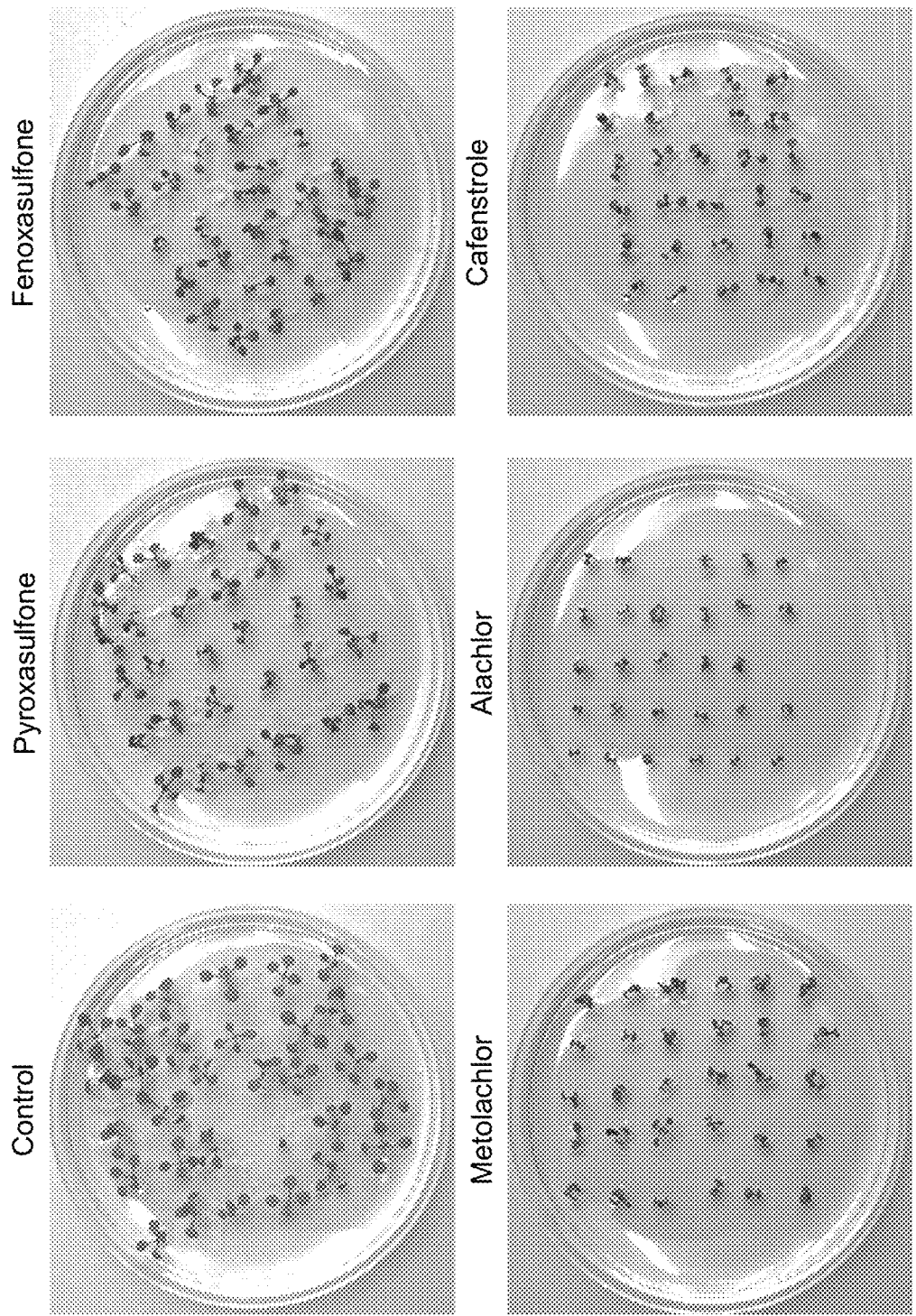
[Fig. 13]

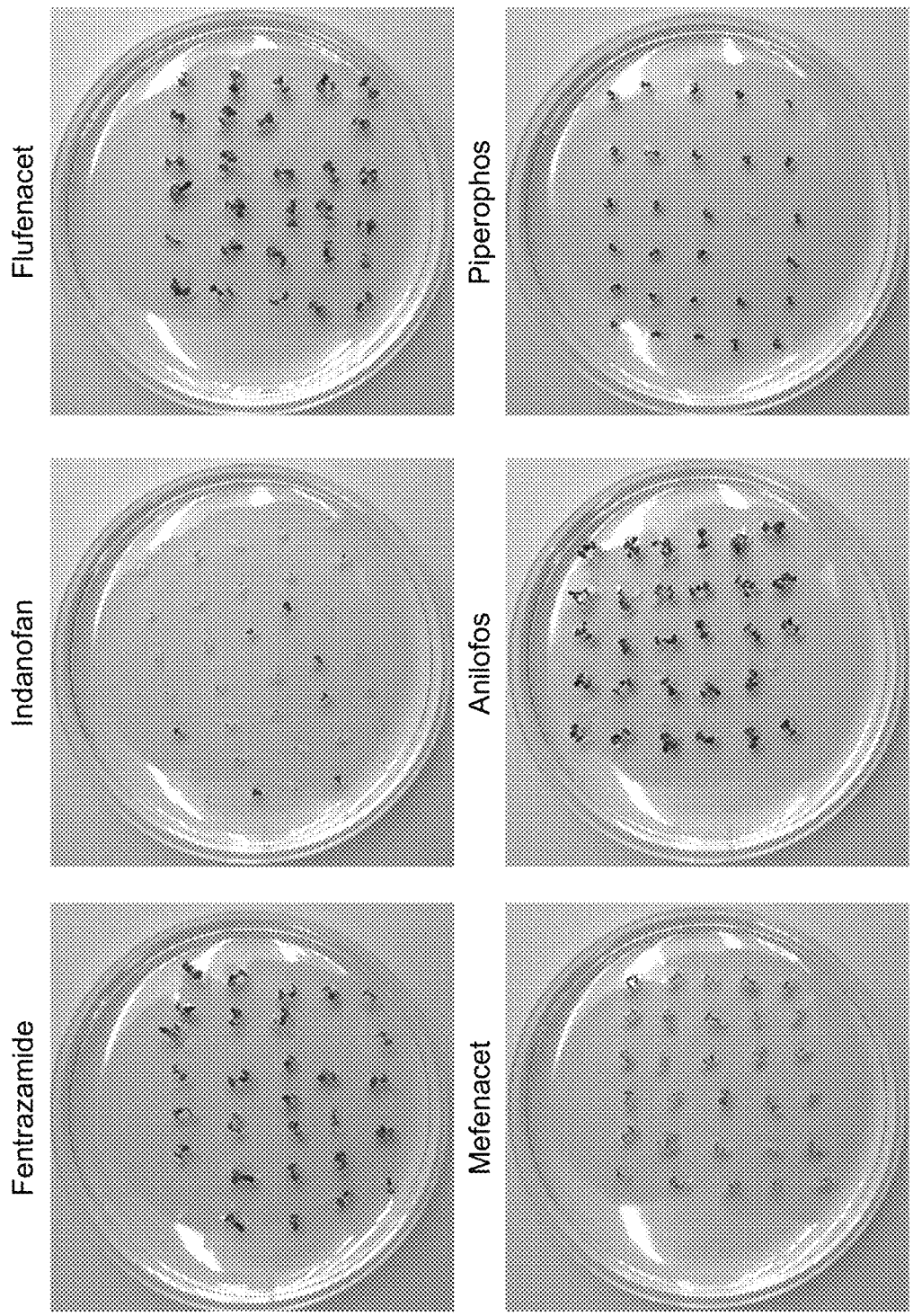
[Fig. 14]

[Fig. 15]
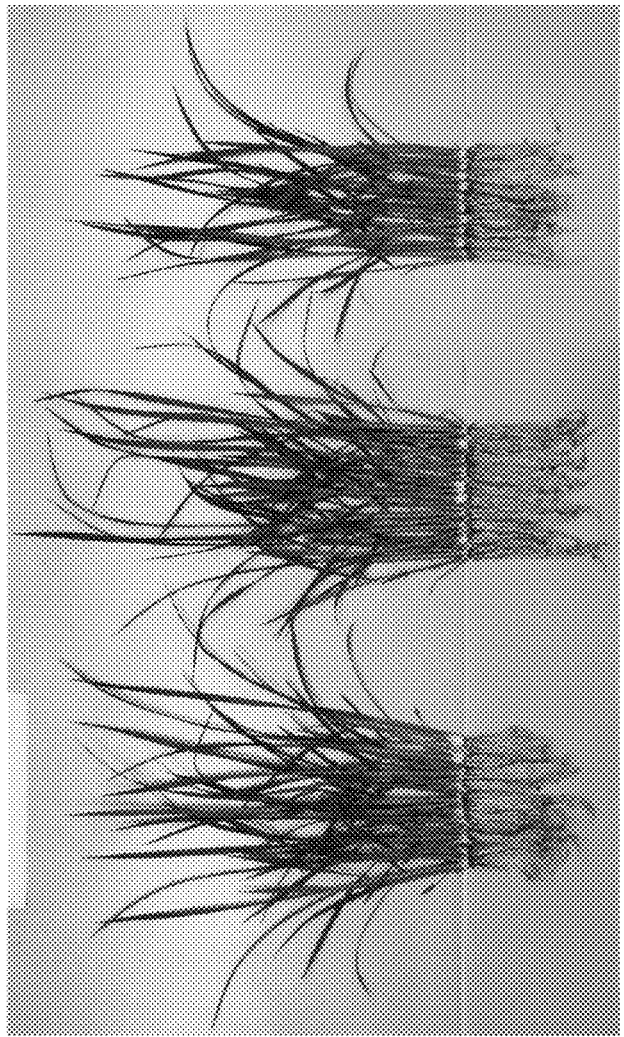

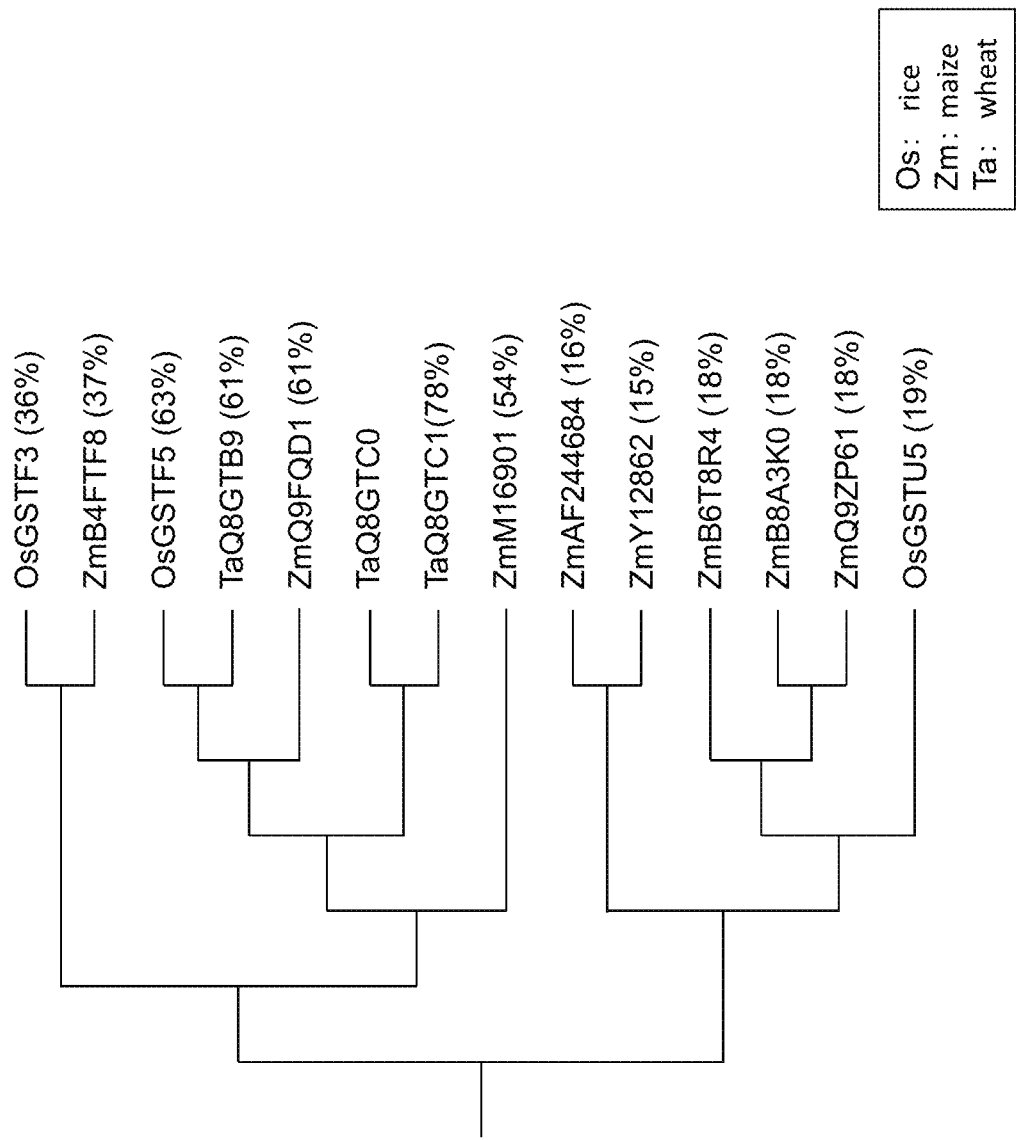
[Fig. 16]

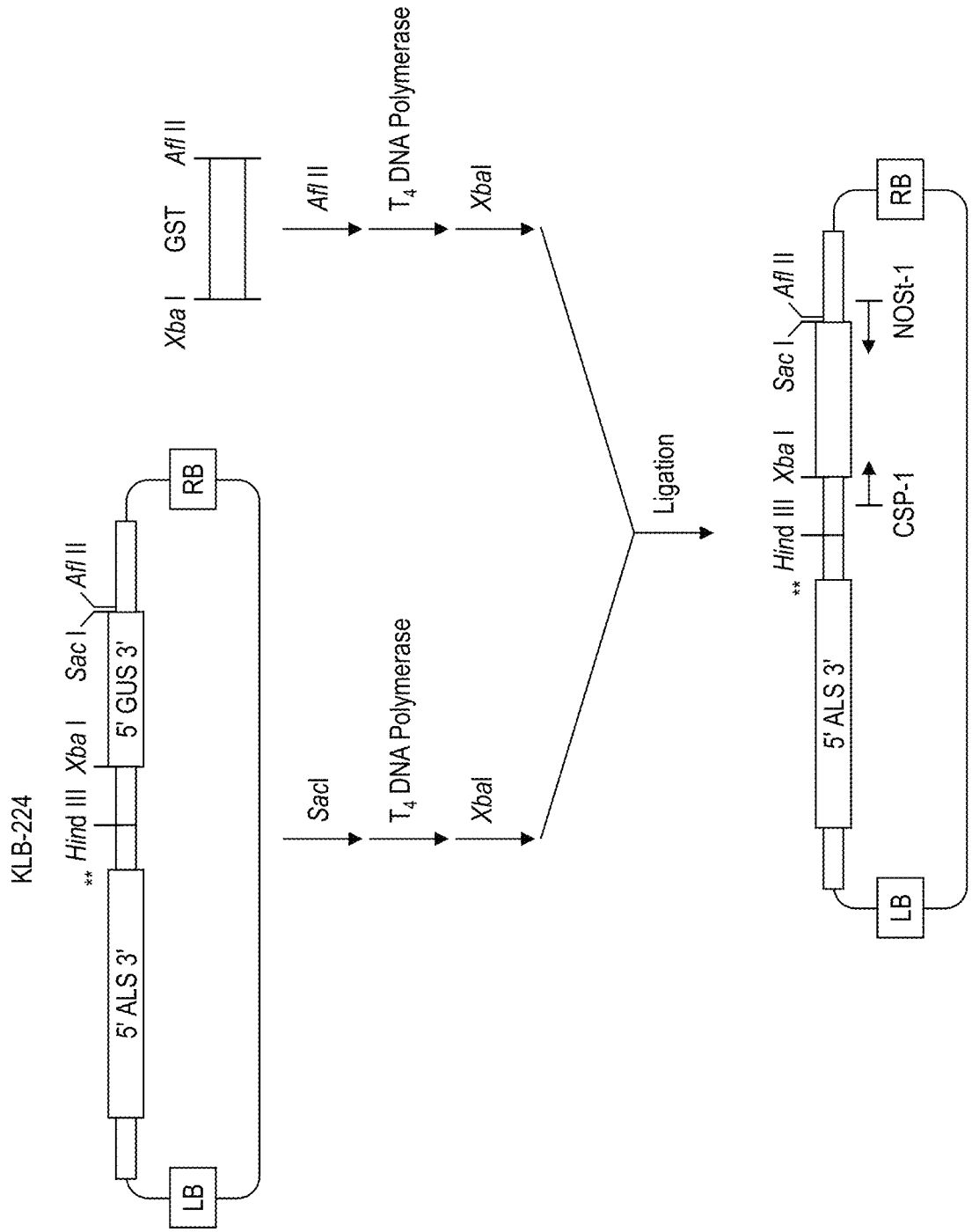
[Fig. 17]

[Fig. 18]

Fatty acid content in cultured rice cells

| Fatty acid | Control | | TaQ8GTB9 | | ZmM16901 | |
|---|---|---|---|---|---|---|
| | | | Lineage 1 | Lineage 2 | Lineage 1 | Lineage 2 |
| | \\ | | Content (μg/g fresh weight) | | | |
| | $10^{-7}$ | 0 | $10^{-7}$ | $10^{-7}$ | $10^{-7}$ | $10^{-7}$ |
| | | | Pyroxasulfone concentration (M) | | | |
| C14:0 | 60.25 | 41.97 | 58.45 | 41.18 | 46.19 | 61.3 |
| C15:0 | 103.21 | 6.99 | 141.43 | 50.04 | 101.52 | 96.88 |
| C16:0 | 996.47 | 952.62 | 1149.52 | 692.54 | 1249.92 | 985.17 |
| C18:0 | 156.07 | 96.68 | 227.6 | 181.81 | 210.92 | 160.46 |
| C18:1 | 857.16 | 246.16 | 802 | 486.33 | 832.95 | 725.42 |
| C18:2 | 3083.96 | 2660.85 | 3662.86 | 1844.68 | 3920.97 | 3188.48 |
| C18:3 | 785.07 | 592 | 886.11 | 471.64 | 856.52 | 891.24 |
| C20:0 | 27.78 | 28.01 | 24.52 | 25.06 | 37.26 | 29.59 |
| C20:1 | 20.48 | 26.11 | 16.28 | 10.36 | 28.04 | 18.81 |
| C22:0 | 36.67 | 50.68 | 13.05 | 19.79 | 34.41 | 27.07 |
| C22:1 | 12.61 | 35.56 | 5.22 | 3.95 | 10.53 | 5.84 |
| C24:0 | 19.33 | 53.69 | 10.41 | 13.46 | 13.83 | 17.42 |

[Fig. 19]

Fatty acid content in cultured rice cells

| Fatty acid | Control | | ZmY12862 | | ZmB6T8R4 | | ZmQ9ZP61 | |
|---|---|---|---|---|---|---|---|---|
| | | | Lineage 1 | Lineage 2 | Lineage 1 | Lineage 2 | Lineage 1 | Lineage 2 |
| | | | Content (μg/g fresh weight) | | | | | |
| | $10^{-7}$ | 0 | $10^{-7}$ | $10^{-7}$ | $10^{-7}$ | $10^{-7}$ | $10^{-7}$ | $10^{-7}$ |
| | | | Pyroxasulfone concentration (M) | | | | | |
| C14:0 | 43.7 | 36.6 | 25.3 | 34.6 | 40.9 | 36.5 | 44.1 | 45.3 |
| C15:0 | 20.5 | 9.03 | 20.5 | 18.8 | 22.8 | 23.7 | 19.5 | 24.2 |
| C16:0 | 1022 | 876 | 894 | 978.3 | 812 | 98.3 | 875 | 1023 |
| C18:0 | 377 | 261 | 157 | 247 | 300 | 363 | 286 | 369 |
| C18:1 | 393 | 359 | 345 | 345 | 339 | 378 | 409 | 424 |
| C18:2 | 2953 | 2680 | 2784 | 3007 | 2306 | 2595 | 2710 | 2883 |
| C18:3 | 840 | 779 | 938 | 969 | 597 | 689 | 712.9 | 753 |
| C20:0 | 74.9 | 43.6 | 36.5 | 48.3 | 50.8 | 64 | 55.6 | 75.3 |
| C20:1 | 17.2 | 34 | 22.5 | 23.2 | 12.6 | 13.8 | 15.5 | 18.4 |
| C22:0 | 90.3 | 75.5 | 71.3 | 89.8 | 48.5 | 64.1 | 71.8 | 85.4 |
| C22:1 | 13.5 | 34.5 | 17.7 | 17.7 | 10.1 | 10.4 | 12.4 | 16.7 |
| C24:0 | 38.7 | 106 | 61.9 | 59.8 | 26.7 | 28.5 | 34.6 | 46.1 |

[Fig. 20]

Fatty acid content in cultured rice cells

| Fatty acid | Control | OsGSTF5 | | | | OsGSTU5 | |
|---|---|---|---|---|---|---|---|
| | | Lineage 1 | | Lineage 2 | Lineage 1 | | Lineage 2 |
| | | Content (μg/g fresh weight) | | | | | |
| | | Pyroxasulfone concentration (M) | | | | | |
| | $10^{-6}$ | $10^{-6}$ | $10^{-6}$ | $10^{-6}$ | $10^{-6}$ | $10^{-6}$ | $10^{-6}$ |
| C14:0 | 38.4 | 43.3 | 40.9 | 49.9 | 57 | 59.5 |
| C15:0 | 153 | 119 | 166 | 144 | 159 | 183 |
| C16:0 | 462 | 498 | 532 | 456 | 460 | 595 |
| C18:0 | 84.9 | 140 | 110 | 108 | 124 | 103 |
| C18:1 | 163 | 261 | 141 | 156 | 226 | 173 |
| C18:2 | 1661 | 1752 | 1696 | 1536 | 1636 | 1915 |
| C18:3 | 758 | 627 | 648 | 595 | 668.3 | 757 |
| C20:0 | 6.07 | 10.2 | 5.69 | 6.69 | 15.2 | 7.86 |
| C20:1 | 2.58 | 3.94 | 1.4 | 1.54 | 3.82 | 3.19 |
| C22:0 | 3.01 | 3.1 | 2.31 | 2.43 | 3.17 | 3.3 |
| C22:1 | 0.27 | 1.22 | 2.9 | 1.09 | 2.19 | 3.62 |
| C24:0 | 4.01 | 5.44 | 6.36 | 6.53 | 8.33 | 5.66 |

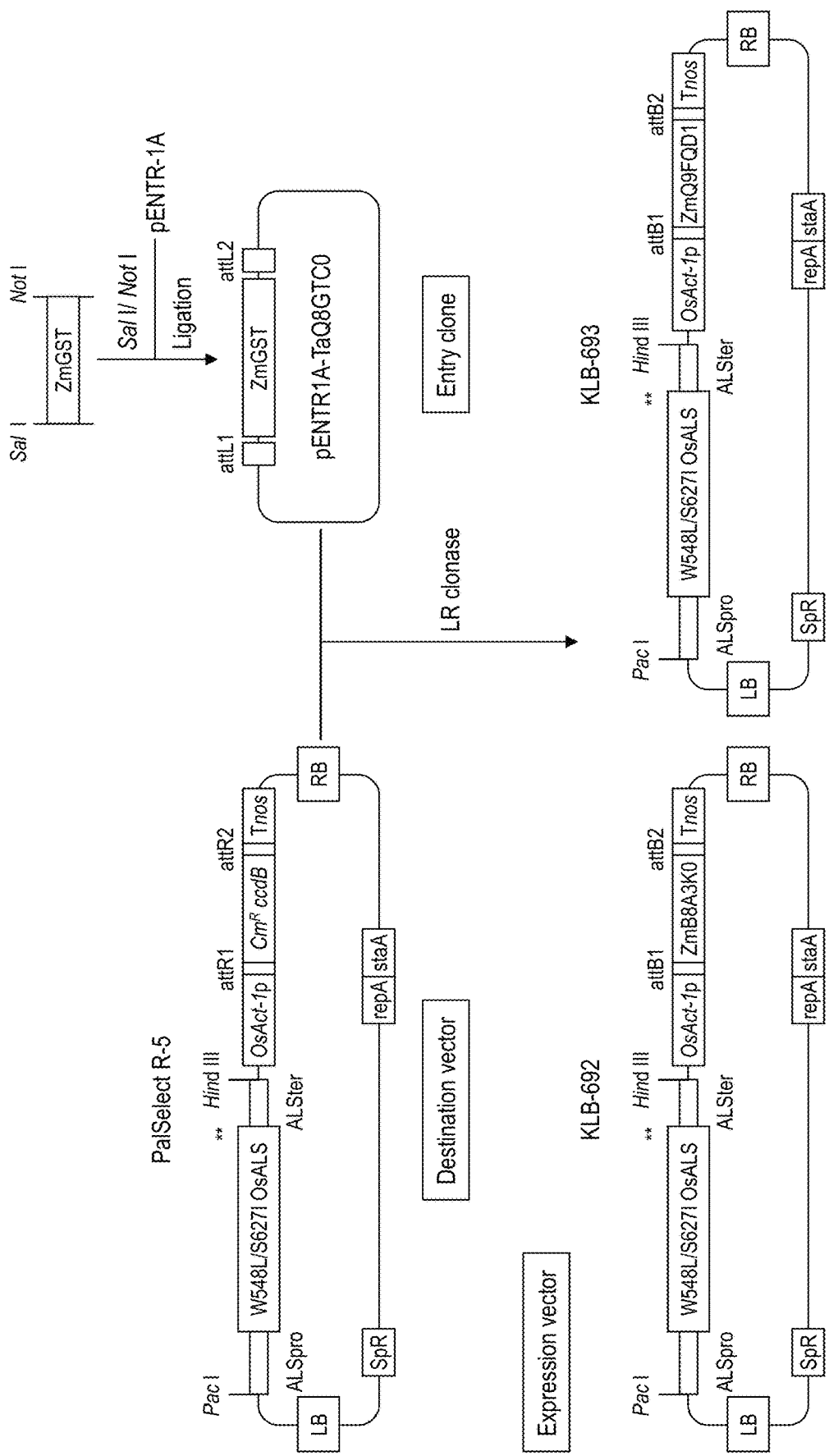
[Fig. 21]

[Fig. 22]
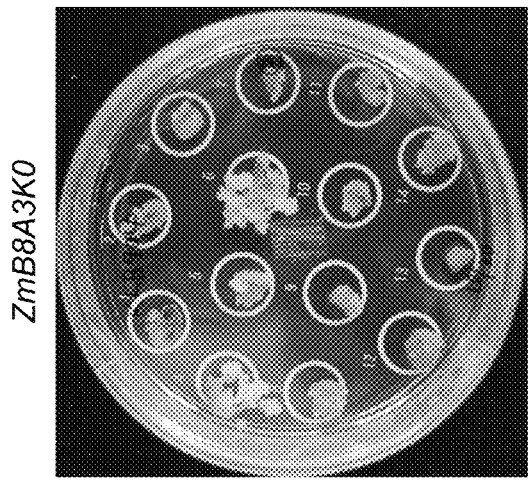
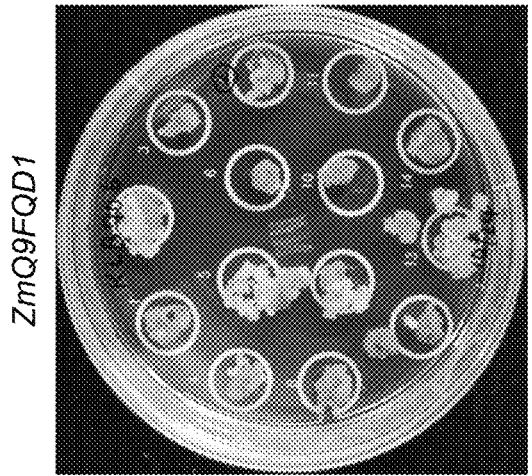
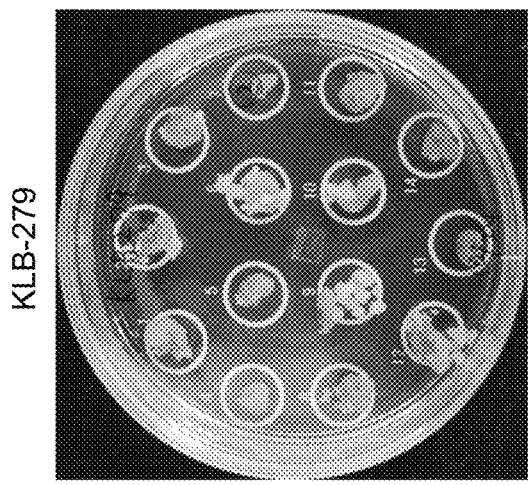

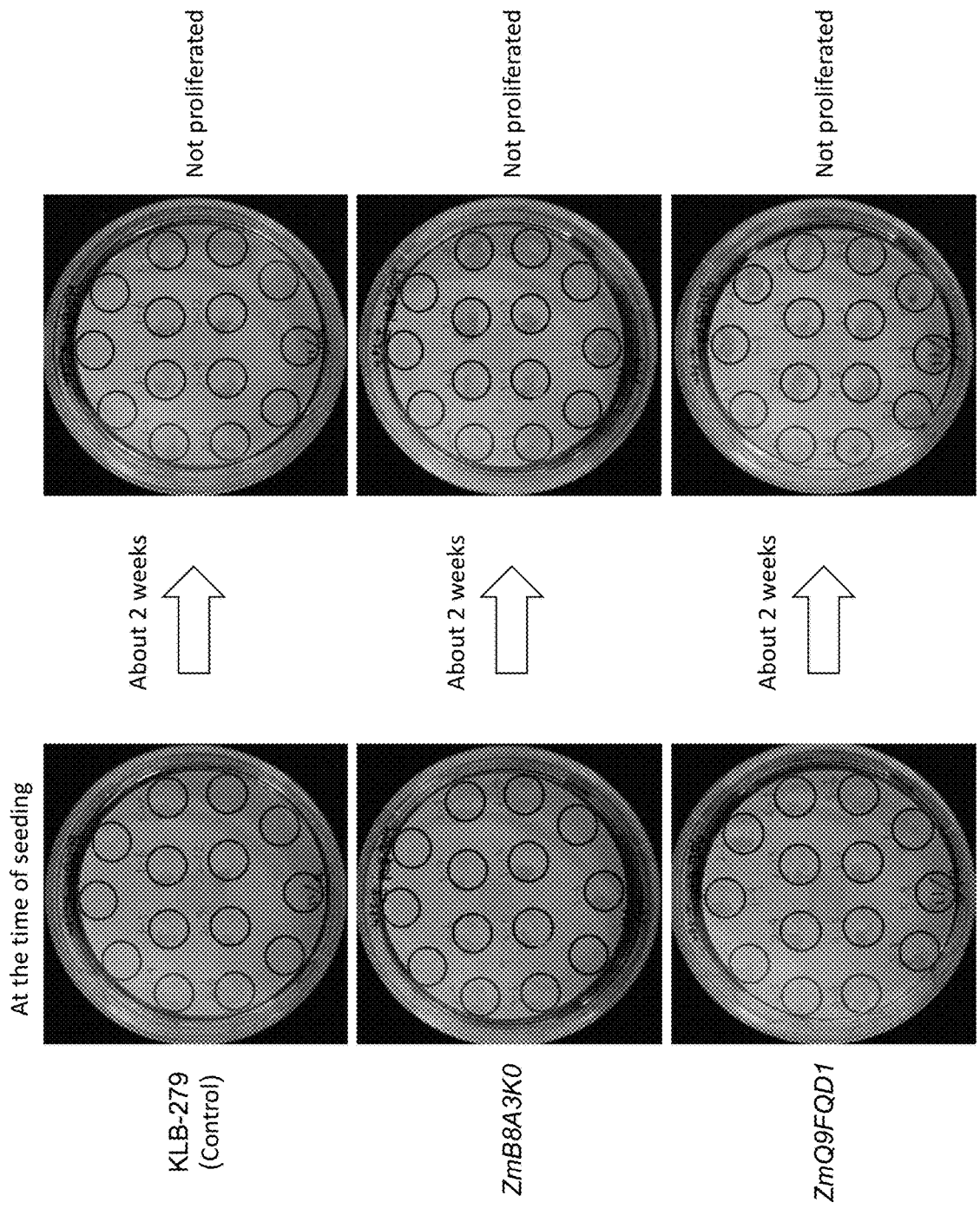
[Fig. 23]

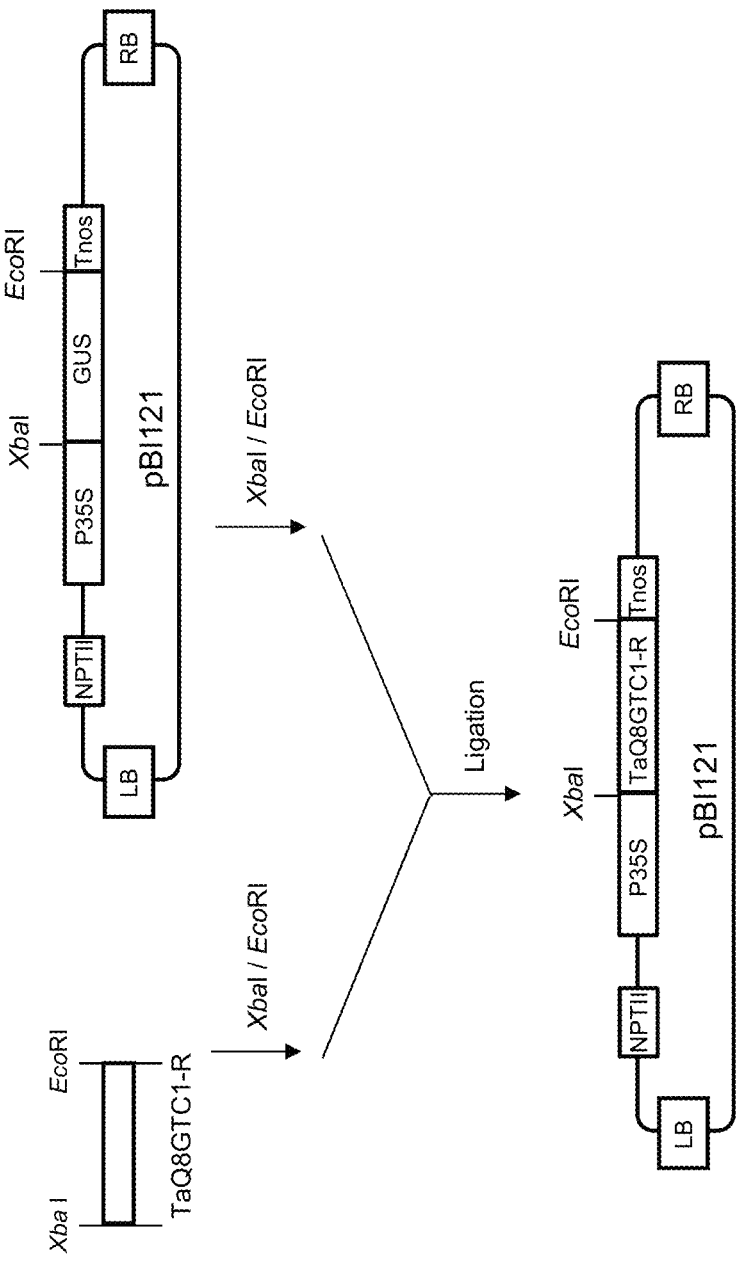
[Fig. 24]

[Fig. 25]

```
TaG8GTC1-R    1:ATGGGCGGCGCCGGCGTGAAGGTGACGGGTGGGCGATGTCGCCGTTCGTGGCGCGCGTTGCTGTGCCTGGAGGAGGC   80
TaQ8GTC1      1:ATGGGCGGCGCCGGCGTGAAGGTGACGGGTGGGCGATGTCGCCGTTCGTGGCGCGCGCTGCTGTGCCTGGAGGAGGC   80
                ****************************************************** **********************

TaG8GTC1-R   81:CGGCGTGGAGTACGAGCTCGTCCGCCATGAGCCGGAGCCGCCACCGCCAGCCGGACTTCCTCGCCAGGAACCCCT  160
TaQ8GTC1     81:CGGCGTGGAGTACGAGCTCGTCGTCCGCCATGAGCCGGAGCCGCCACCGCCAGCCCACTTCCTCGCCCGGAACCCCT  160
                ********************** ****************************** ********** **********

TaG8GTC1-R  161:TCGGCCAGGTCCCCGTTCTCGGAGGACGGCGACCTCACCATCTTCGAATCGCGCGCCGTCGGCGAGGCACGTGCTGCGCAAG  240
TaQ8GTC1    161:TCGGCCAGGTCCCCGTTCTCGGAGGACGGCGACCTCACCATCTTCGAGTCGCGCGCCGTCGGCGAGGCACGTGCTGCGCAAG  240
                *********************************************** *****************************

TaG8GTC1-R  241:CACAAGGCCGGAGCTGCTGGGCTCGCGCCGGAGTCGGCGGCGAAGGTGACGTGTGGCTGGAGGTGGAGGCCACCA  320
TaQ8GTC1    241:CACAAAACCGGAGCTGCTGGGCTCGCGCCGGAGTCGGCGGCGAATGGTGACGTGTGGCTGGAGGTGGAGGCCACCA  320
                ***** ************************************** ****************************

TaG8GTC1-R  321:GCACCAGACCCCGGCGGGCACCCTCCACCCGTTCCTCACCCGTTCCTCCGGCTGCGAGGCGACCAGACCGCCA  400
TaQ8GTC1    321:GCACCAGACCCCGGCGGGCACCCTCCACCCGTTCCTCACCCGTTCCTCCGGCTGCGCAGCGACCAGCCGCCA  400
                ******************************************************* ****** *****

TaG8GTC1-R  401:TCGACGAGAACGCGGCAAAGCTGACGAAGGCTGTTCGACGTGTACGAGGGCGCGCTGTCGGCGTCGAGGTACCTCGCCGGG  480
TaQ8GTC1    401:TCGACGAGAACGCGGCAAAGCTGACGAAGACTGTTCGACGTGTACGAGGGCGCGCTGTCGGCGTCGAGGTACCTTCCCGGG  480
                ***************************** ****************************************** ****

TaG8GTC1-R  481:GACTCCTCAGCCTCGCCACCTCAGCCACCTTCATGGACCACCTTCCCGTCTACTTCATGGACACCGAGTACGCGTCGCTGGTGGT  560
TaQ8GTC1    481:GAGGTGGCAGCCTCGCCACCTCAGCCACCTTCATGGACCACCTTCCCGTTTACTTCATGGACACCGAGTACGCGTCGCTGGTGGA  560
                ** * ******************************************* *************************** *

TaG8GTC1-R  561:GGAGCGCCCCGCACGTGAAGGCGTGGTGGGAGGAGCGCAAGGCCCAGCGCGGCGGCGAAGAGGGTGACGGAGTTCATGCCGC  640
TaQ8GTC1    561:GGAGCGCCCCGCACGTGAAGGCGTGGTGGGAGGAGCCAAGGCCCAGCCCGGCGGCGAAGAGGGTGACGGAGTTCATGCCGC  640
                *********************************** ********** ******************************

TaG8GTC1-R  641:CAAAACTTCGGGTTCGGAAAGAAGGCAGAGAGAAGTGA  675
TaQ8GTC1    641:CAAAACTTCGGGTTCGGAAAGAAGGCAGAGAGAAGTGA  675
                **************************************
```

[Fig. 26]

```
TaQ8GTC1-R    1:MAAPAVKV[H]GWAMSPFVARALLCIEEAGVEYELVPMSREAGDHRQPDFLARNPFGQVPVL  60
TaQ8GTC1      1:MAAPAVKV[Y]GWAMSPFVARALLCIEEAGVEYELVPMSREAGDHRQPDFLARNPFGQVPVL  60
                ********  ***************************************************

TaQ8GTC1-R   61:EDGDLTIFESRAVARHVLRKHKPELLGSGSPESAA[K]VDVWLEVEAHQHTPAGTIVMQCI 120
TaQ8GTC1     61:EDGDLTIFESRAVARHVLRKHKPELLGSGSPESAA[M]VDVWLEVEAHQHTPAGTIVMQCI 120
                ***********************************  ************************

TaQ8GTC1-R  121:LTPFLGQ[E]RDQ[T]AIDENAAKLT[K]LFDVYEARLSASRYLAG[DSL]SLADLSHFP[I]MRYFMDT 180
TaQ8GTC1    121:LTPFLGQ[Q]RDQ[A]AIDENAAKLT[N]LFDVYEARLSASRYLAG[EAV]SLADLSHFP[E]MRYFMDT 180
                *******  ***  **********   ******************    ********   *******

TaQ8GTC1-R  181:EYASLV[V]ERPHVK[V]WWEE[L]KA[R]PAAKRVTEFMPPNFGFGKKAEK 224
TaQ8GTC1    181:EYASLV[M]ERPHVK[A]WWEE[F]KA[S]PAAKRVTEFMPPNFGFGKKAEK 224
                ******  ******  ****  **  ********************
```

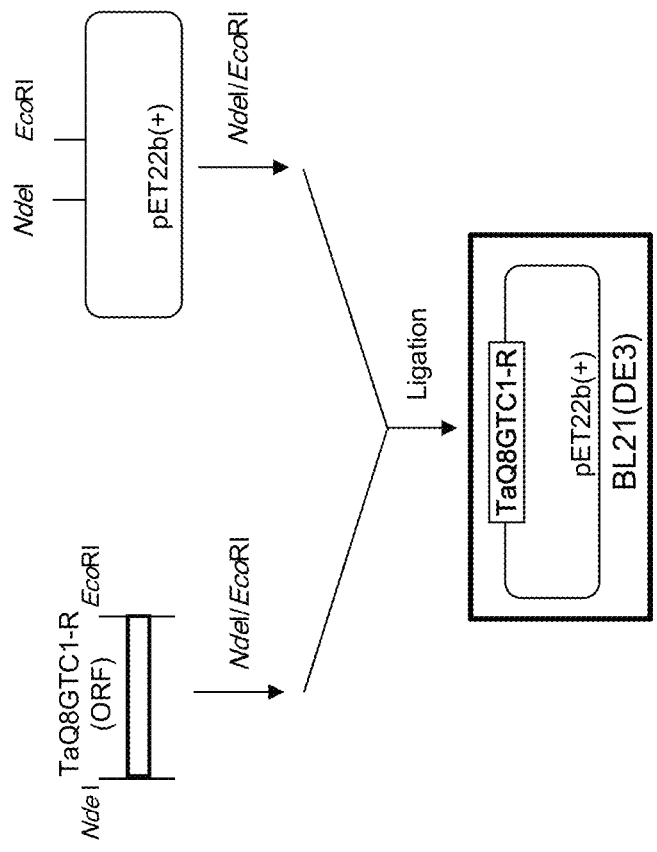
[Fig. 27]

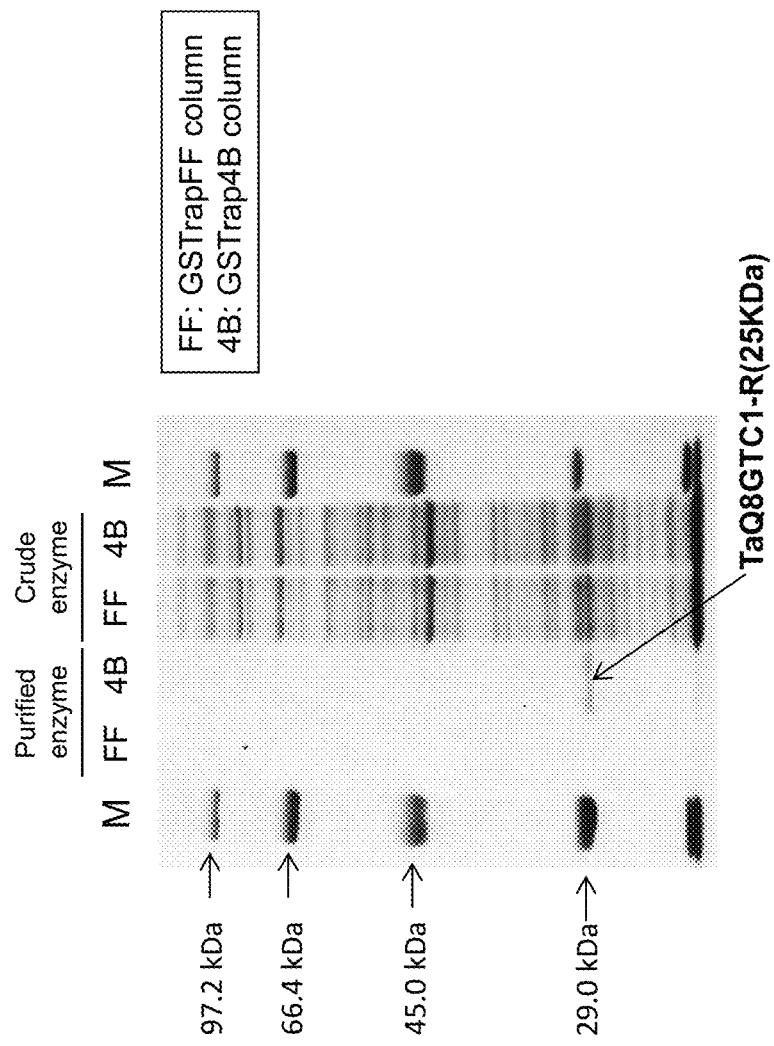
[Fig. 28]

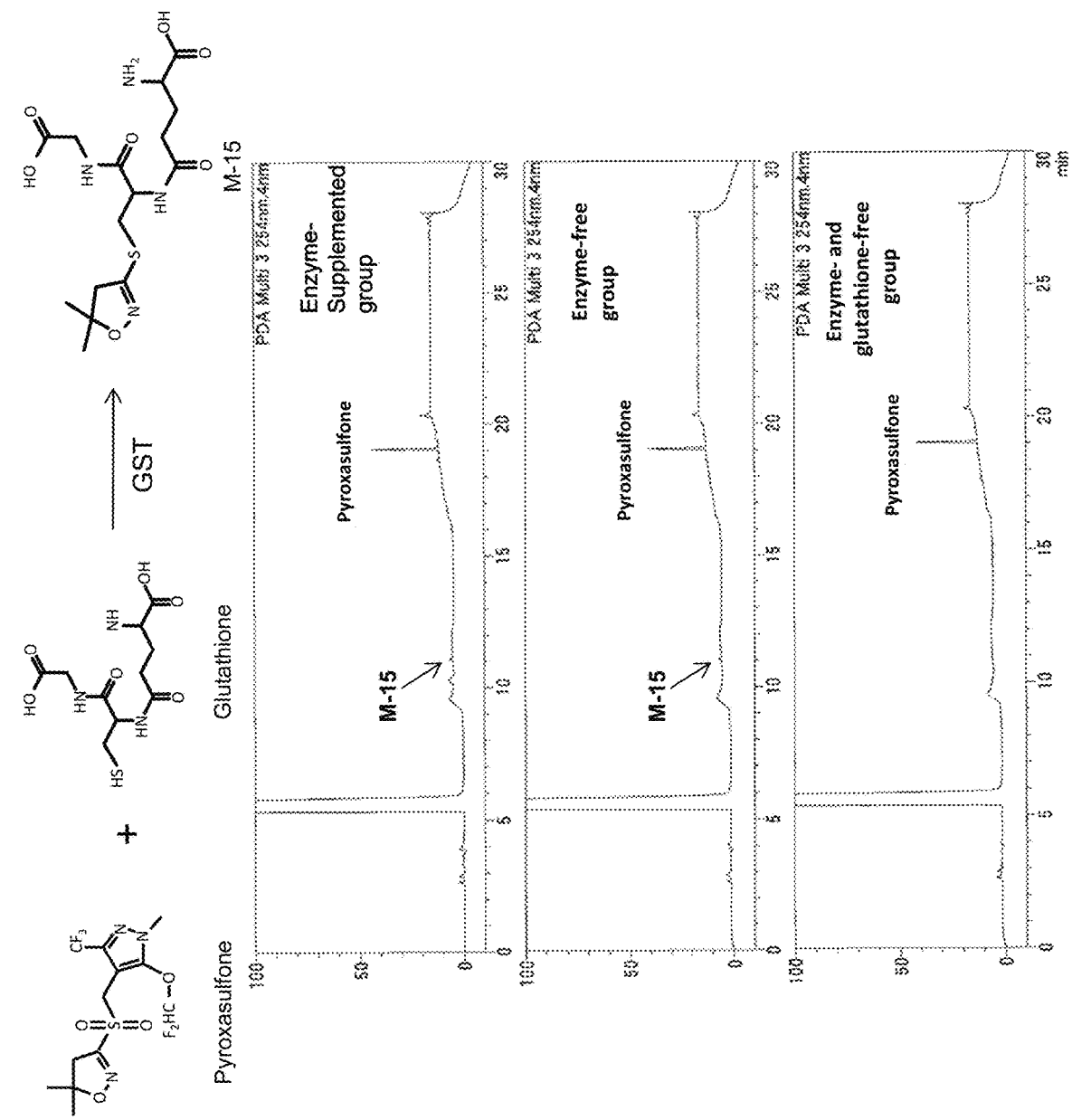
[Fig. 29]

[Fig. 30]

Putative substrate recognition site 1

```
AtGSTF2    1:---MAGIKVFGHPASIATRRVLIALHEKNLDFELIVHVELKDGEHKKEPPLSRNPFGQVPAFEDGDLKLFESRAITQYIAHR  78
PttGSTF1   1:--MATPVTINGPPLSTAVSRVLATLIEKDVPFHLVPIDLSKGEQKKPEYLKIQPFGQVPAFKDESITLFESRAICRYICDK  79
ZmGSTF1    1:--MAPMKLYGAVMSWNLIRCATALEEAGSDYEIVPINFATAEHKSPEHLVRNPFGQVRNPFFGQVPALQDGDLYLFESRAICKYAARK  78
TaGSTF1    1:--MAPVKIYGATLSWNVTRCVAALEEAGVQYEIVPINFGTGEHKSPDHLARNPFGQVPALQDGDLYVFESRAICKYACRK  78
TaGSTF2-R  1:MAAPAVKVHGWAMSPFVARALLCLEEAGVEYELVPMSREAGDHRQPDFLARNPFGQVPVLEDGDLTIFESRAVARHVLRK  80
TaGSTF3    1:--MAPAVKVYGWAVSPFVARPLLCLEEAGVEYELVSMSRAAGDHRQPDFLARNPFGQVPVLEDGDLTLFESRAIARHVLRK  79
TaGSTF4    1:---MEPMKVYGWAVSPWMARVLVSLEEEAGDYELVPMSRNGGDHRRPEHLARNPFGEIPVLEYGGLTLYQSRAIARHILRK  78
TaGSTF5    1:---MAPIKIYGMMLSANVTRVTTLLNELGLEFDFVDVDLRTGAHKHPDFKLNPFGQIPALQDGDEVVFESRAINRYIATK  78
TaGSTF6    1:---MAPVKVFGPAMSTNVARVLVCLEEVGAEYEVVDIDFKAMEHKSPEHLVRNPFFGQIPAFQDGDLLLFESRAIARYVLRK  78
```

Putative substrate recognition site 2

```
AtGSTF2    79:YENQGTNLLQTDSKNISQYAIMAIGMQVEDHQFDPVASKLAFEQIFKSIYGLTTDEAVVAEEEAKLAKVLDVYEARLKEF 158
PttGSTF1   80:YADKGNRSLYGTDILSK---ANIDQWVETDGQTFGPPSGDIVHDLLFSSV--PVDEALIKKNVDKLAKVLIDIYEQKLGQT 157
ZmGSTF1    79:----NKPELLREGNLEEA--AMVDVWIEVEANQYTAALNPILFQVLISPMLGTTDQKVVDENLEKLKKVLEVYEARLTKC 153
TaGSTF1    79:----NKPELLIKEGDIKES--AMVDVWLEVEAHQYTAALSPILFECLIHPMLGATDQKVIDDNLVKIKNVLAVYEAHLSKS 153
TaGSTF2-R  81:--HKPELLGSGSPESA--AKVDVWLEVEAHQHQTPAGTIVMQCILTPFLGCERDQTAIDENAAKLTKLFDVYEARLSAS 155
TaGSTF3    80:--HKPELLGCGSPEAE--AMVDVWLEVEAHQYNPAASAIVVQCIILPLLGGARDQAVVDENVAKLKKVLEVYEARLSAS 154
TaGSTF4    79:--HKPGLLGAGSLEES--AMVDVWVDVDAHHLEPVLKPIVWNCIINPFVGRDVDQGLIVDESVEKLKKLLEVYEARLSSN 153
TaGSTF5    79:--YGASLLPT-----PS--AKLEAWLEVESHHFYPPARTIVYELVIKPMLGAPTDAAEVDKNAADLAKLLDVYEAHLAAG 149
TaGSTF6    79:YKKNEVDLLREGDLKEA--AMVDVWTEVDAHTYNPAISPILYECSSTAHARLPTNQTVVDESLEKLIKNVLEVYEARLSKH 116
```

```
AtGSTF2   159:--KYLAGETFTLTDLHHIPAIQYLLGTPTKK-LFTERPRVNEWVAEITKRPASEKVQ-------------------  215
PttGSTF1  158:--RFLAGDEEFSFADLSHLPNGDYLVNSTDKGYLFTSRKNVNRWWTEISNRESWKKVLEMRKNA-----------  215
ZmGSTF1   154:--KYLAGDFLSLADLNHVSVTLCLFATPYAS--VLDAYPHVKAWWSGLMERPSVQKVAALMKPSA----------  214
TaGSTF1   154:--KYLAGDFLSLADLNHVSVTLCLAATPYAS--LFDAYPHVKAWWTDLLARPSVQKVAALMKP-----------  212
TaGSTF2-R 156:--RYLAGDSLSLADLSHFPLMRYFMDTEYAS--LVVERPHVKVWWEELKARPAAKRVTEFMPPNFGFGKKAEK   224
TaGSTF3   155:--RYLAGDDISLADLSHFPFTRYFMETEYAP--LVAELPHVNAWWEGLKARPAARKVTELMPPDLGLGKKAE-   222
TaGSTF4   154:--KYLAGDFVSFADLTHFSFMRYFMATEHAV--VLDAYPHVKAWWKALLARPSVKKVIAGMPPDFGFGSGRIP  222
TaGSTF5   150:NKYLAGDAFFLADANHMSYLFMLTKSPKAD--LVASRPHVKAWWEEISARPAWAKTVASIPLPPAV-------  213
TaGSTF6   117:--DYLAGDFVSFADLNHFPYTFYFMATPHAA--LFDSYPHVKAWWERIMARPAVKKLAAQMVPKKP-------  218
```

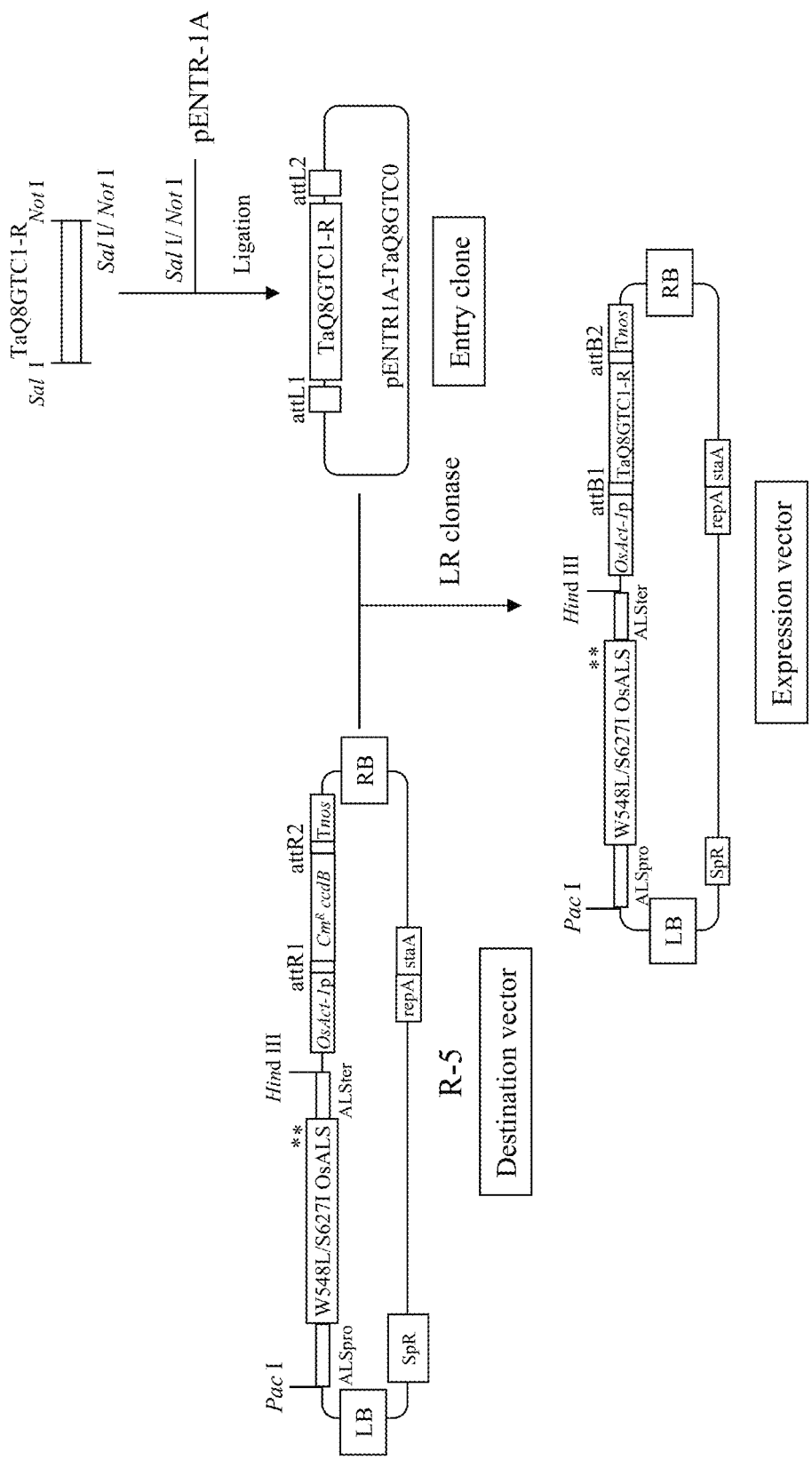
[Fig. 31]

[Fig. 32]
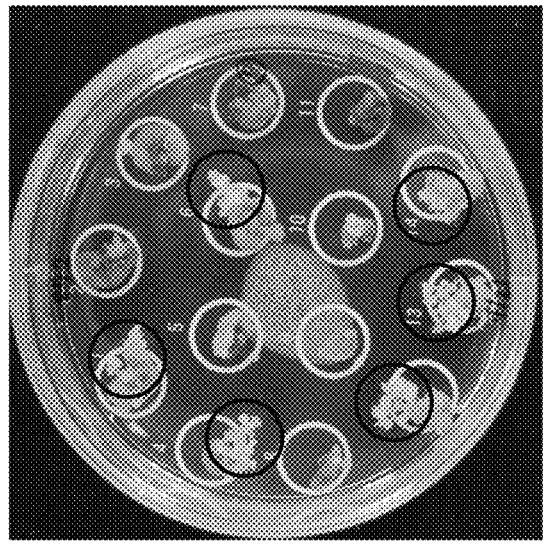
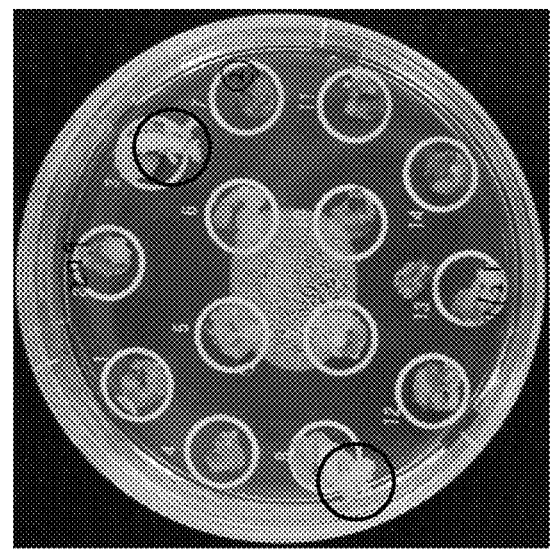

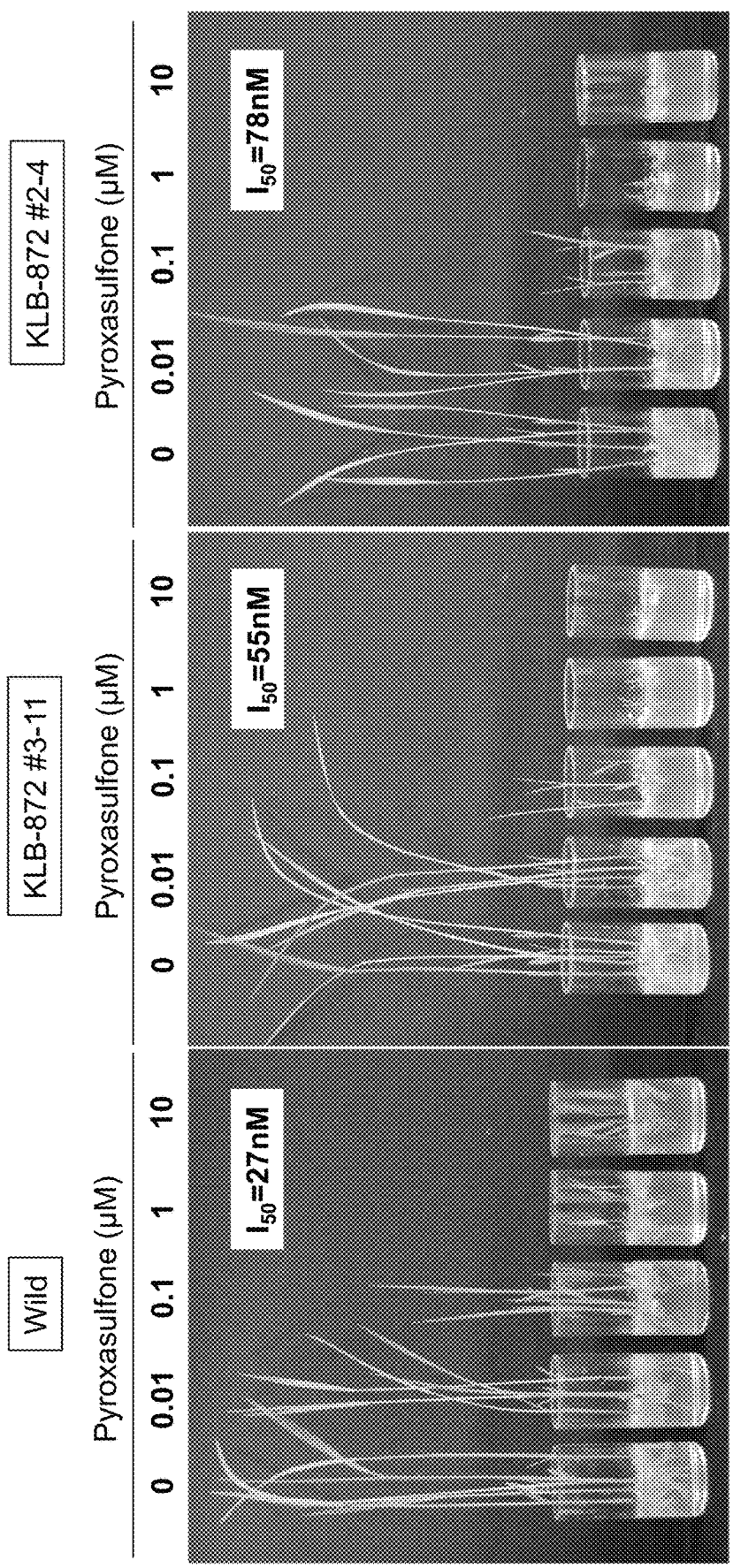
[Fig. 33]

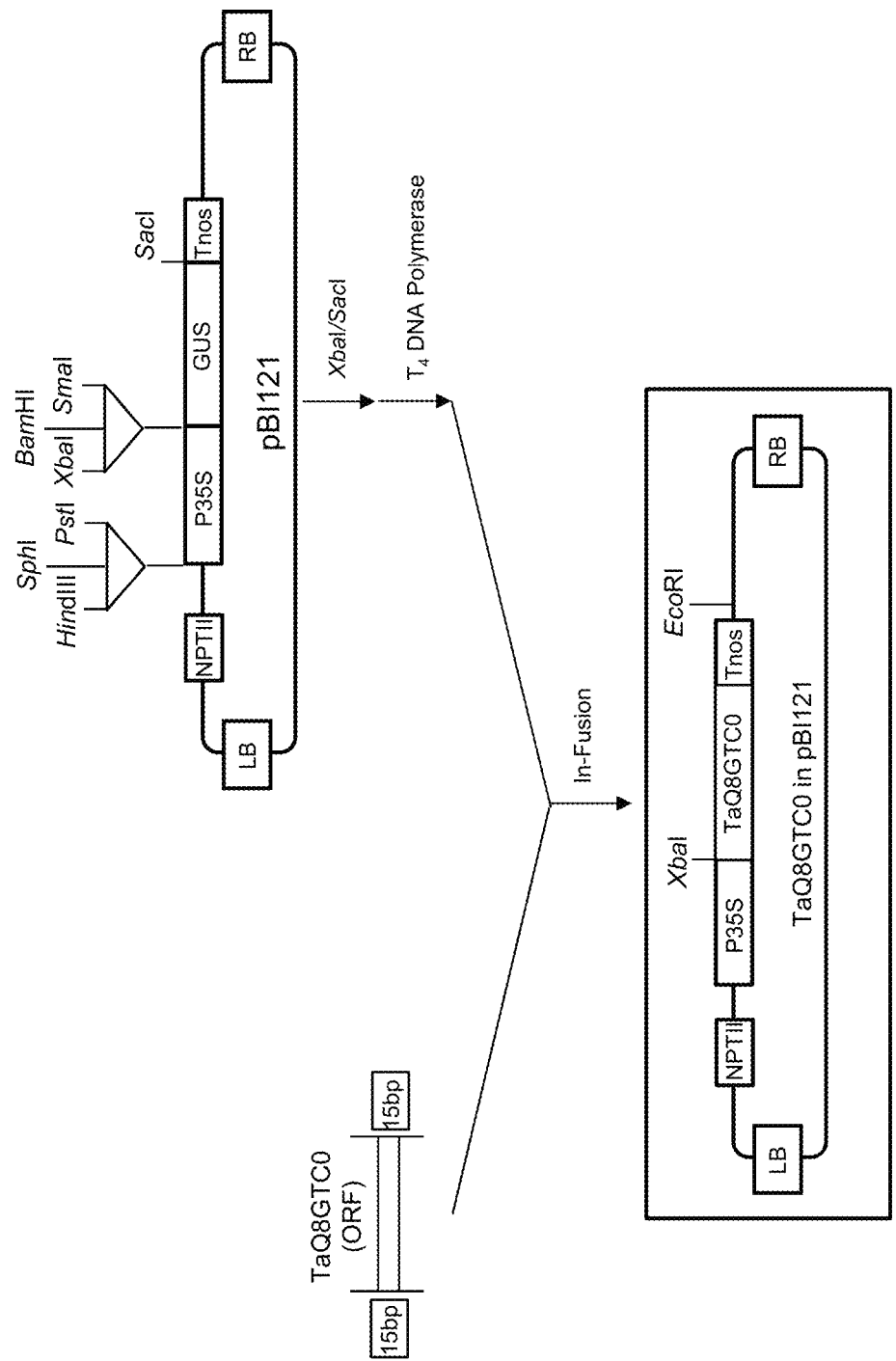
[Fig. 34]

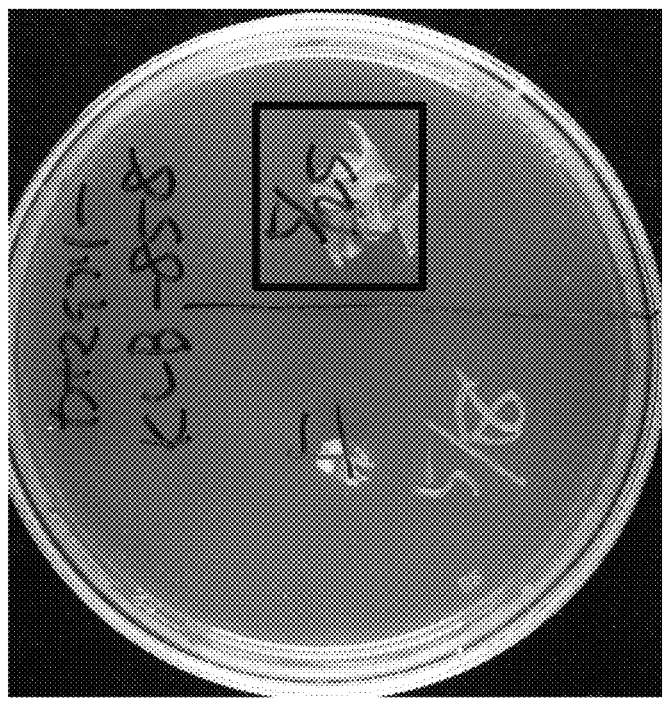
[Fig. 35]

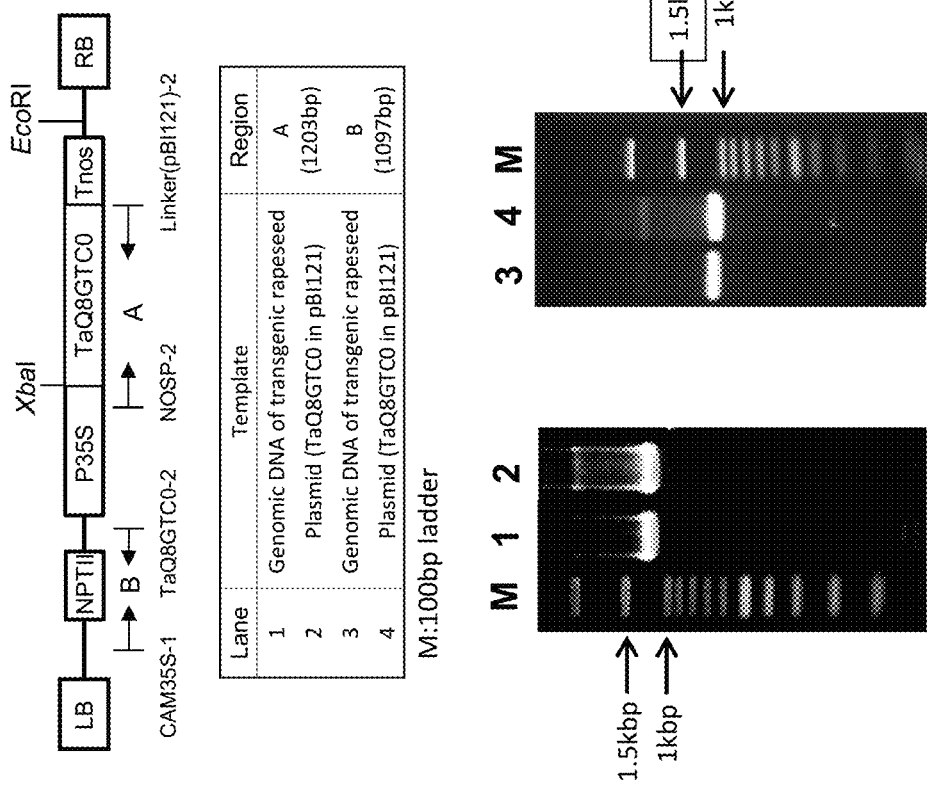
[Fig. 36]

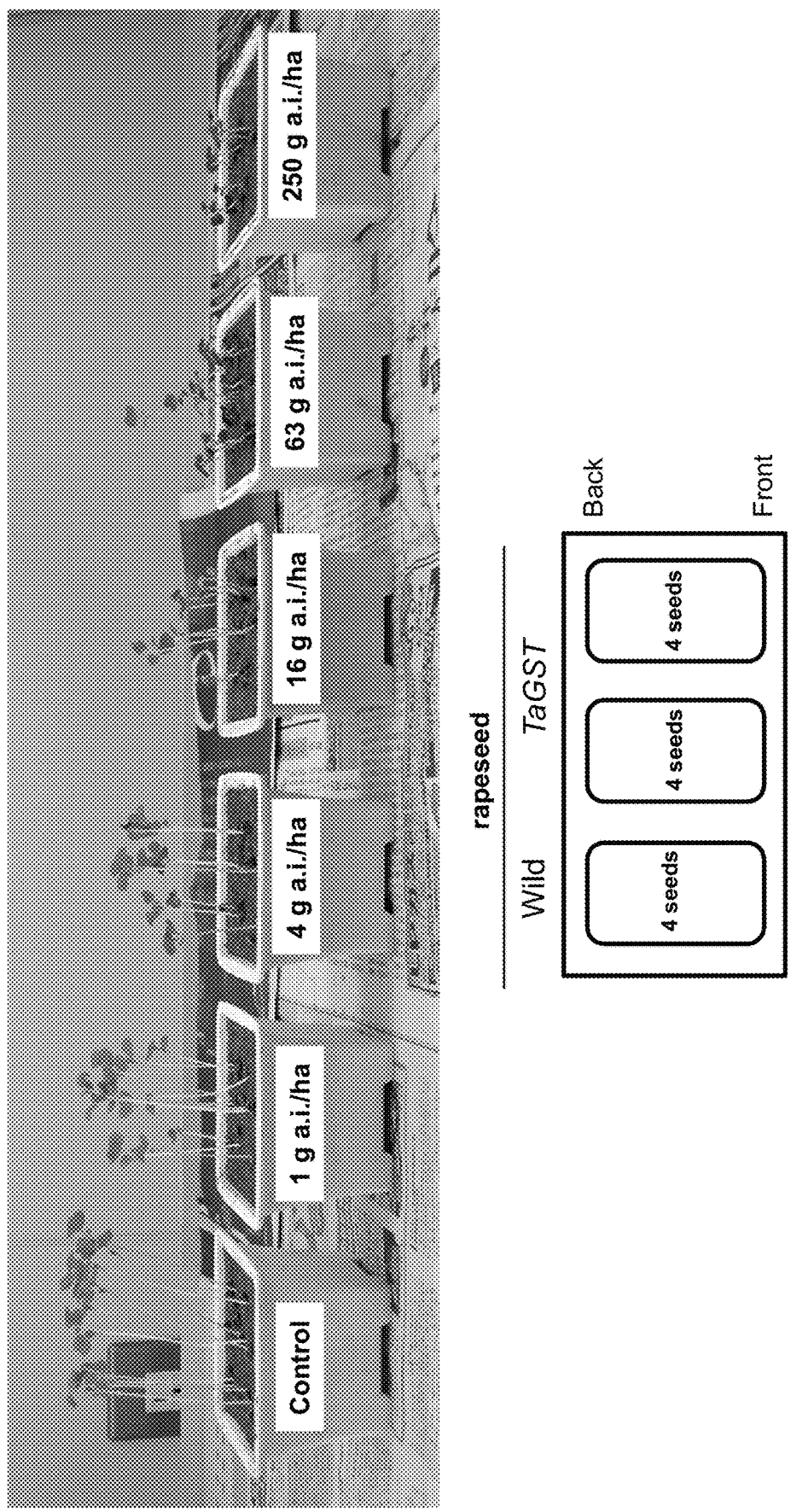
[Fig. 37]

[Fig. 38]
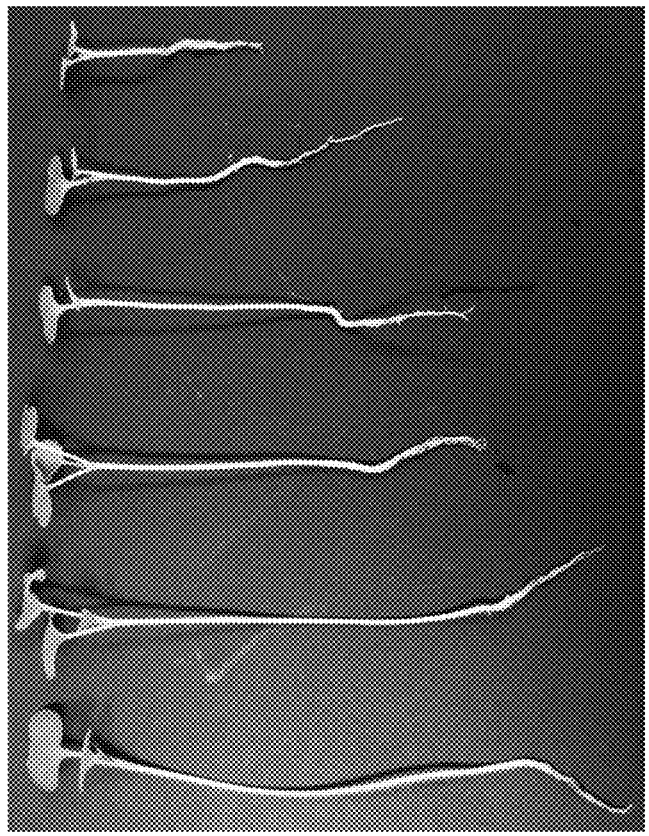
TaGST
| Pyroxasulfone dose (g a.i./ha) | Plant height (mm) | Inhibition (%) |
|---|---|---|
| 0 (Control) | 106±6.01 | - |
| 1 | 91.8±12.6 | 14.1±11 |
| 4 | 72.2±8.36 | 32.2±7.9 |
| 16 | 55.1±5.38 | 48.2±5.1 |
| 63 | 44.0±8.21 | 58.6±7.7 |
| 250 | 37.5±4.93 | 64.8±4.6 |
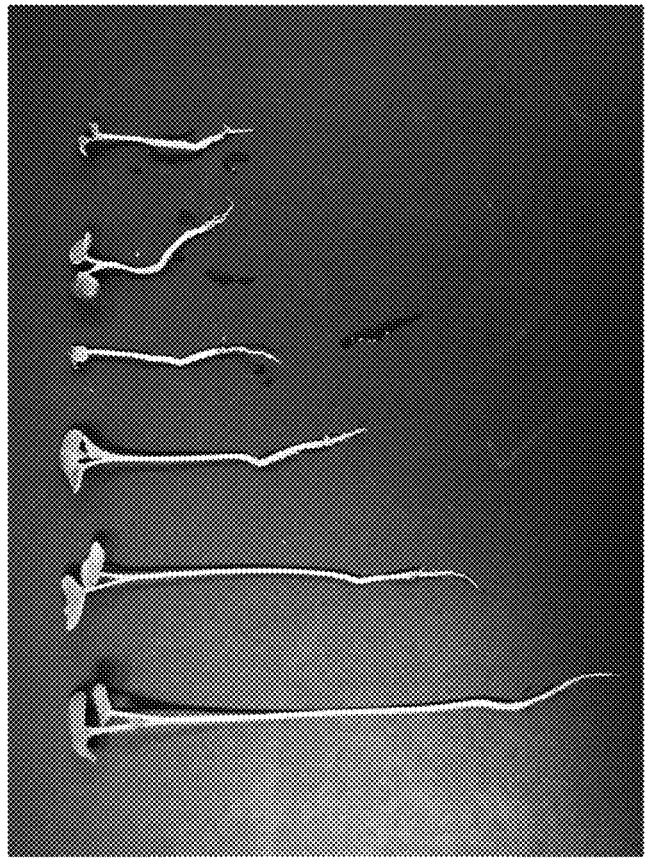
Wild
| Pyroxasulfone dose (g a.i./ha) | Plant height (mm) | Inhibition (%) |
|---|---|---|
| 0 (Control) | 95.9±8.63 | - |
| 1 | 81.3±10.2 | 15.3±11 |
| 4 | 59.8±11.1 | 37.6±12 |
| 16 | 36.5±3.78 | 61.9±3.9 |
| 63 | 36.4±3.46 | 62.1±3.6 |
| 250 | 33.7±5.28 | 64.8±5.5 |

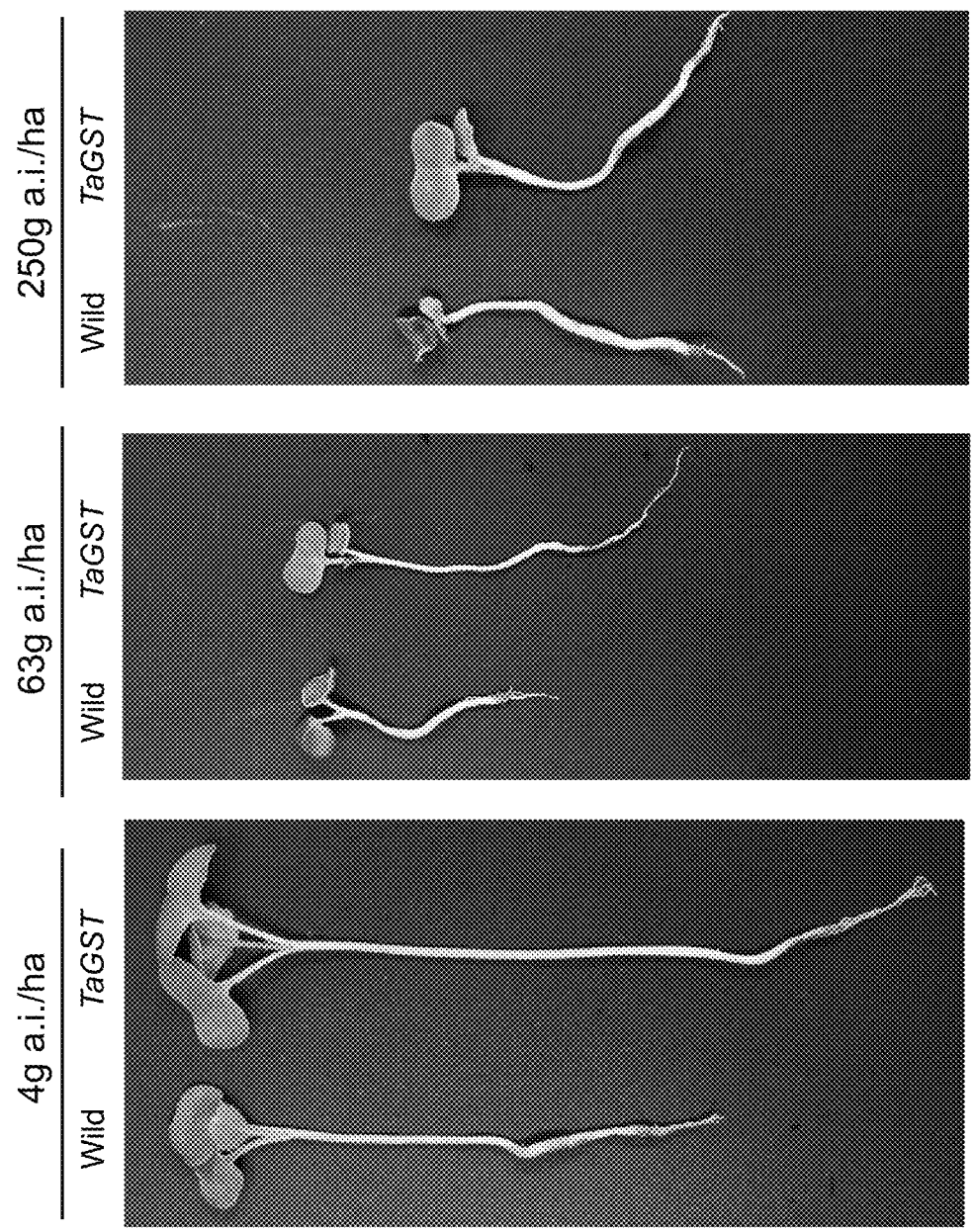
[Fig. 39]

[Fig. 40]
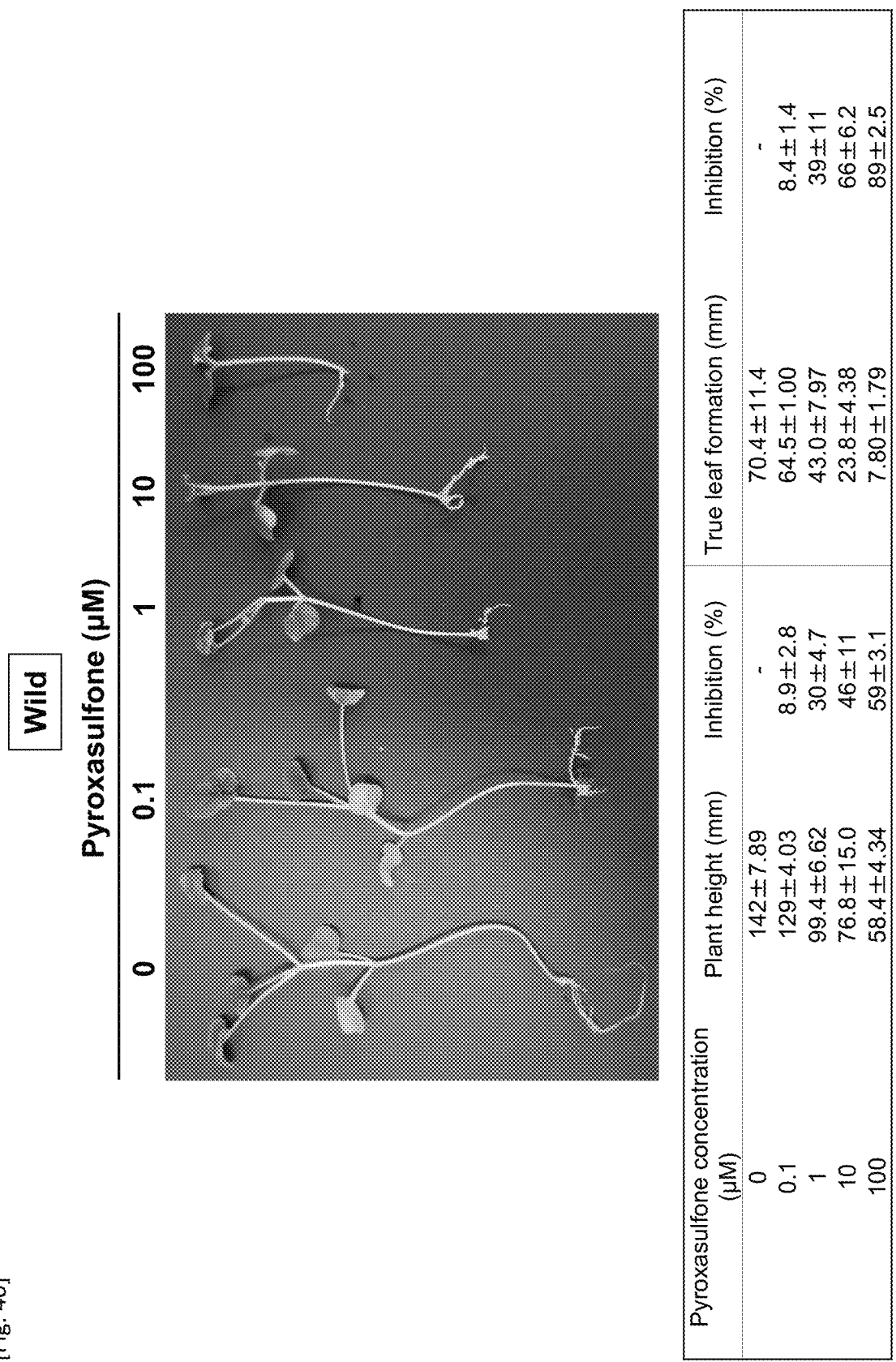
| Pyroxasulfone concentration (μM) | Plant height (mm) | Inhibition (%) | True leaf formation (mm) | Inhibition (%) |
|---|---|---|---|---|
| 0 | 142±7.89 | - | 70.4±11.4 | - |
| 0.1 | 129±4.03 | 8.9±2.8 | 64.5±1.00 | 8.4±1.4 |
| 1 | 99.4±6.62 | 30±4.7 | 43.0±7.97 | 39±11 |
| 10 | 76.8±15.0 | 46±11 | 23.8±4.38 | 66±6.2 |
| 100 | 58.4±4.34 | 59±3.1 | 7.80±1.79 | 89±2.5 |

[Fig. 41]
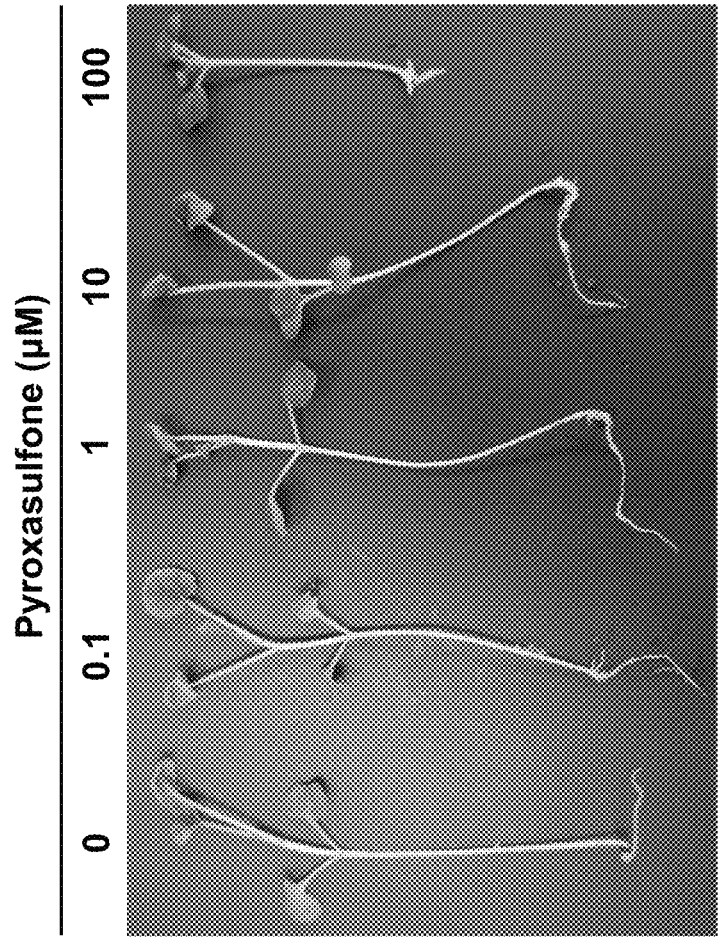
| Pyroxasulfone concentration (μM) | Plant height (mm) | Inhibition (%) | True leaf formation (mm) | Inhibition (%) |
|---|---|---|---|---|
| 0 | 120±2.83 | - | 46.8±6.53 | - |
| 0.1 | 146±10.8 | 0±0 | 71.3±10.2 | 0±0 |
| 1 | 112±18.9 | 10±8.1 | 47.4±9.91 | 6.6±7.6 |
| 10 | 111±7.06 | 7.8±5.9 | 48.6±3.36 | 1.2±2.7 |
| 100 | 59.5±3.70 | 50±3.0 | 11.3±2.99 | 76±6.4 |

[Fig. 42]
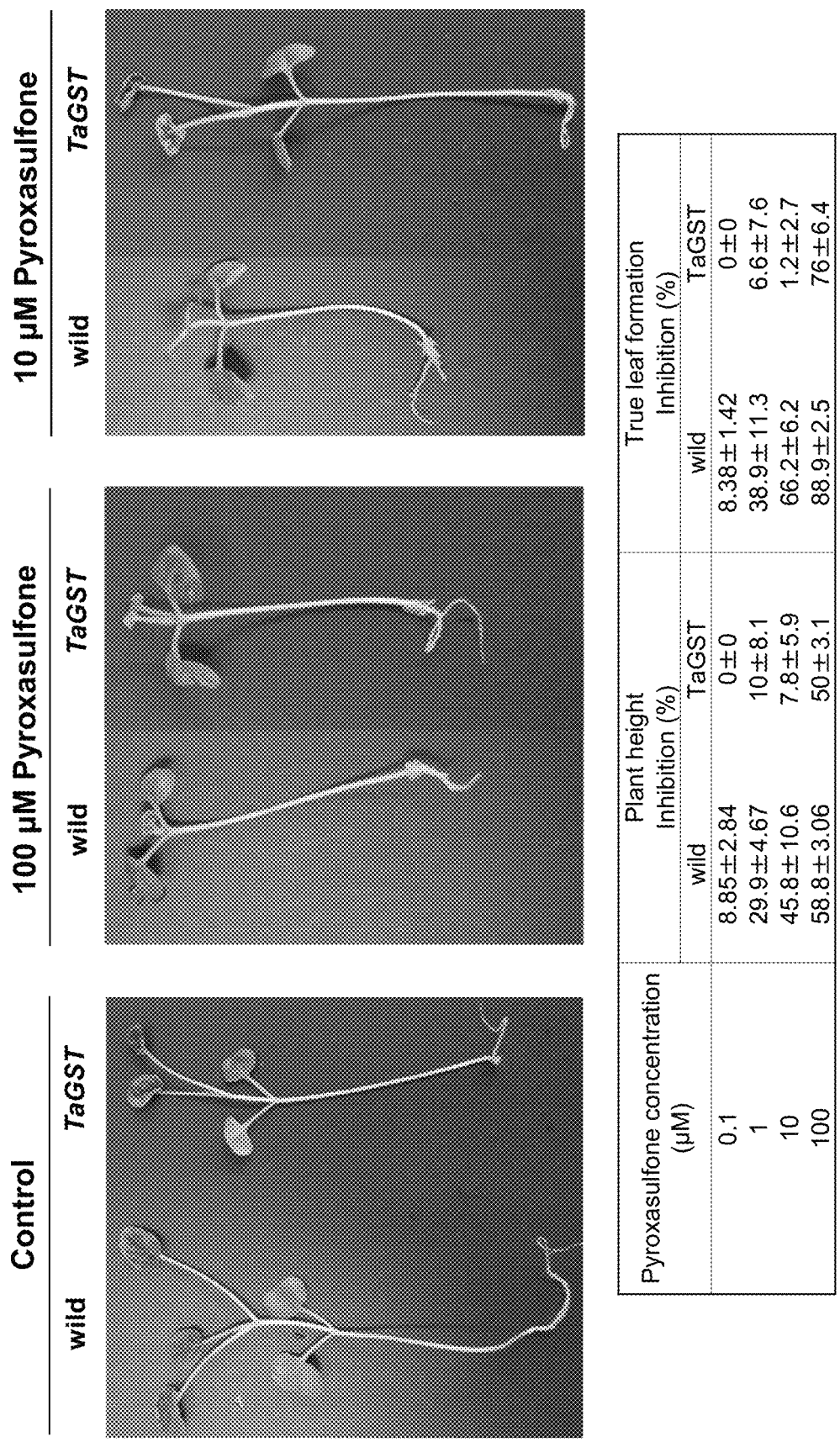

[Fig. 43]
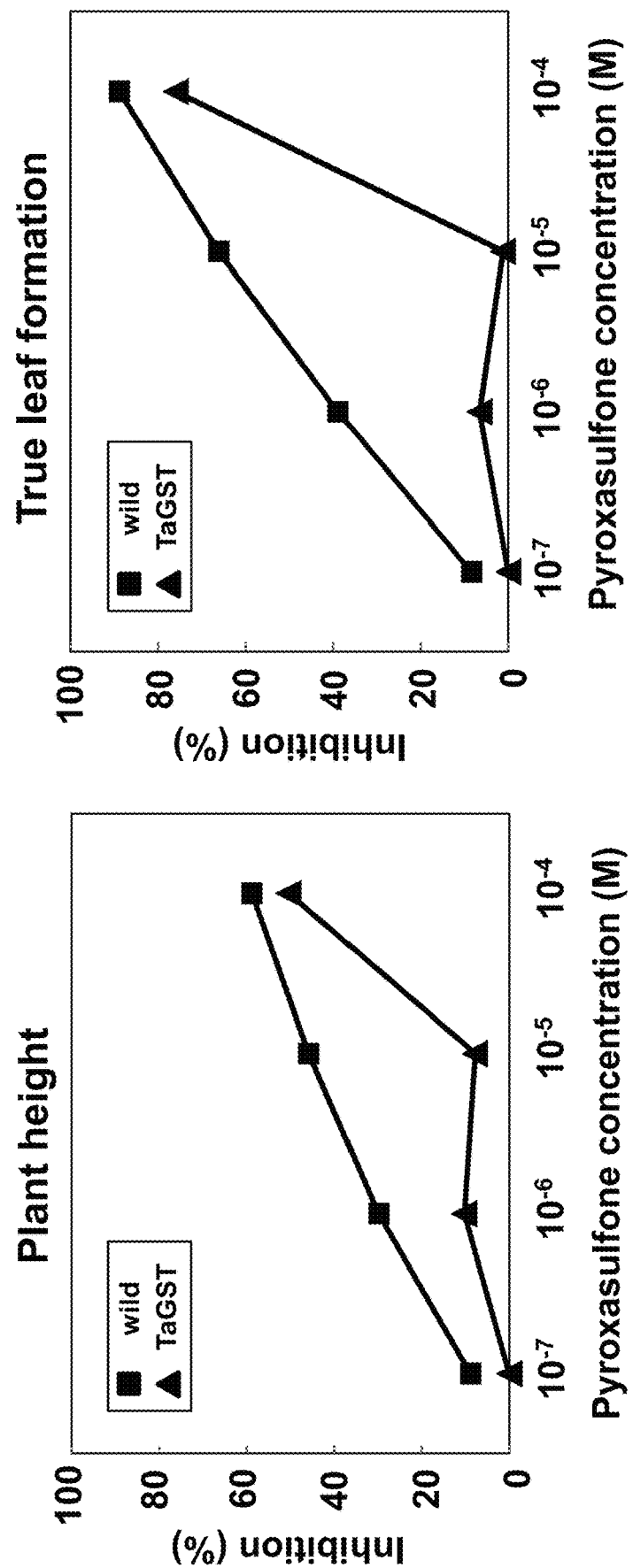

[Fig. 44]
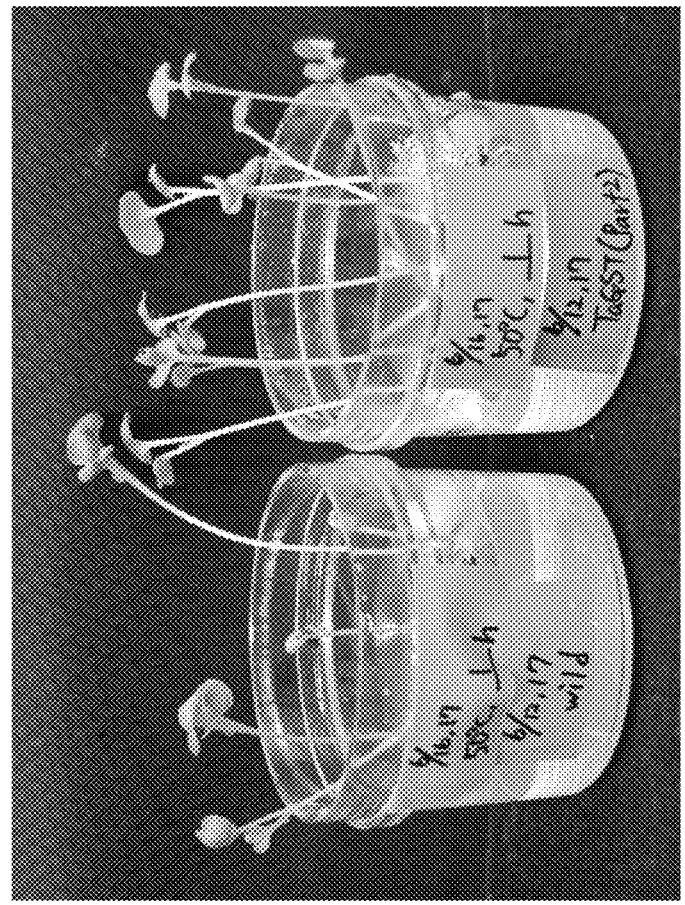

TRANSGENIC PLANT HAVING HERBICIDE RESISTANCE

BACKGROUND OF THE INVENTION

The present invention relates to a transgenic plant that is resistant to isoxazoline derivatives, such as pyroxasulfone and fenoxasulfone.

BACKGROUND ART

A compound having the isoxazoline moiety (i.e., an isoxazoline derivative) is known to have the herbicidal activity. The "isoxazoline moiety" is also referred to as an "isooxazoline moiety." As isoxazoline derivatives, compounds having excellent herbicidal effects and selectivity between crops and weeds have been developed (e.g., pyroxasulfone), as described in Non-Patent Document 1. Pyroxasulfone is a herbicide binding to, as an active site, a very-long-chain fatty acid elongase (VLCFAE) that catalyzes biosynthesis of a very-long-chain fatty acid as a primary component of a sphingolipid in a wax layer or cell membrane of a plant cuticle.

Pyroxasulfone is known to be a herbicide for upland crops that exerts satisfactory herbicidal effects on existing resistant weeds, as well as Gramineae weeds and broadleaf weeds (Non-Patent Document 1). Specifically, pyroxasulfone is safe for crops such as wheat. Meanwhile, rapeseed, barley, rice, and the like are known to have high degrees of sensitivity to pyroxasulfone (Non-Patent Documents 1 and 2). Thus, pesticide registration for pyroxasulfone has not been made for use as a herbicide against rapeseed, barley, rice, and other plants.

Regarding pyroxasulfone, drug metabolism catalyzed by glutathione-S-transferase (GST) may be associated with the resistance in wheat (i.e., wheat selectivity) (Non-Patent Document 3). In general, many reports have been made concerning the metabolism and the detoxification of pesticides caused by glutathione conjugation (Non-Patent Documents 4 to 7). In particular, the metabolism and the detoxification caused by glutathione conjugation are known to be associated with the selectivity between crops and weeds of chloroacetamide compounds as VLCFAE-inhibiting herbicides, as with the case of pyroxasulfone (Non-Patent Documents 8 to 10).

It is known that a plurality of GST molecular species exist in a plant. Non-Patent Document 11 discloses that a maize-derived GST (GSTI, ZmM16901) exerts a high-level conjugation activity on chloroacetamide-based alachlor but it does not exert conjugation activity on the metolachlor, which is very similar to alachlor in terms of the structure. In addition, Non-Patent Document 12 discloses that ZmGST8 (ZmQ9FQD1) having the highest degree of homology to ZmGSTI (amino acid sequence homology: approximately 56%) does not exert conjugation activity on the alachlor. As described above, GST exhibits a high degree of substrate specificity. Accordingly, it is very difficult to identify the molecular species of GST that metabolizes a particular drug even if GST that recognizes a compound similar to the drug described above as a substrate is known.

While plant-derived GST is known to directly reduce oxidative stress (Non-Patent Document 13) and impart resistance to various types of stresses imposed by, for example, salt, dehydration, temperature, or herbicides (Non-Patent Document 14), there have been no reports concerning genes that would simultaneously impart resistance to herbicides and resistance to high temperatures. Also, there is a report concerning resistance to high temperatures imposed on plants via introduction of both GST and GPX (glutathione peroxidase) (Non-Patent Document 15), no reports have been made concerning resistance to high temperatures imposed by GST alone.

PRIOR ART DOCUMENTS

Non-Patent Documents

Non-Patent Document 1: Y. Tanetani et al., Pestic. Biochem. Physiol., 95, 47-55, 2009
Non-Patent Document 2: Y. Tanetani et al., J. Pestic. Sci., 36, 221-228, 2011
Non-Patent Document 3: Y. Tanetani et al., J. Pestic. Sci., 38, 152-156, 2013
Non-Patent Document 4: E. Boyland et al., Adv. Enzymol. Relat. Areas. Mol. Biol., 32, 173-219, 1969
Non-Patent Document 5: B. Mannervik Adv. Enzymol. Relat. Areas. Mol. Biol., 57, 357-417, 1985
Non-Patent Document 6: P. J. Hatton et al., Pestic. Sci., 46, 267-275, 1996
Non-Patent Document 7: D. P. Dixon et al., Genome Biol., 3, 1-10, 2002
Non-Patent Document 8: G. L. Lamoureux et al., J. Agric. Food Chem., 19, 346-350, 1971
Non-Patent Document 9: J. R. C. Leavitt et al., J. Agric. Food. Chem., 27, 533-536, 1979
Non-Patent Document 10: T. Mozer et al., Biochemistry 22, 1068-1072, 1983
Non-Patent Document 11: M. Karavangeli et al., Biomolecular Engineering 22, 121-128, 2005
Non-Patent Document 12: I. Cummins et al., Plant Mol. Biol., 52, 591-603, 2003
Non-Patent Document 13: I. Cummins et al., Plant J., 18, 285-292, 1999
Non-Patent Document 14: R Edwars & D P Dixson, Methods Enzymol., 401, 169-186, 2005
Non-Patent Document 15: V P Roxas et al., Plant Cell Physiol., 41, 1229-1234, 2000

Patent Documents

Patent Document 1: U.S. Pat. No. 6,730,828

DISCLOSURE OF THE INVENTION

Summary of the Invention

It is an object of the present invention to identify a glutathione-S-transferase exhibiting the activities to metabolize and detoxify an isoxazoline derivative, such as pyroxasulfone, thereby providing a transgenic plant having resistance to an isoxazoline derivative with the use of such glutathione-S-transferase, and it is another object to provide a method of the use of an isoxazoline derivative as a herbicide for a plant expressing the glutathione-S-transferase.

Means for Attaining the Objects

The present inventors have conducted concentrated studies in order to attain the above objects. As a result, they succeeded in identifying glutathione-S-transferase existing in wheat that exhibits activities for metabolizing and detoxifying an isoxazoline derivative, such as pyroxasulfone. In addition, they discovered that substrate specificity of the glutathione-S-transferase to an isoxazoline derivative would be very high and, surprisingly, a transgenic plant into which such glutathione-S-transferase (GST) had been introduced would acquire excellent stress resistance. This has led to the completion of the present invention.

The present invention is as follows.

(1) A method for cultivating a transgenic plant comprising cultivating a transgenic plant into which a nucleic acid encoding a protein (a) or (b) below has been introduced in the presence of an isoxazoline derivative:

(a) a protein comprising the amino acid sequence as shown in SEQ ID NO: 2; or (b) a protein comprising an amino acid sequence having 80% or higher identity to the amino acid sequence as shown in SEQ ID NO: 2 and having the activity of glutathione-S-transferase.

(2) The method for cultivation according to (1), wherein the isoxazoline derivative is pyroxasulfone and/or fenoxasulfone.

(3) The method for cultivation according to (1), wherein the transgenic plant is derived from a plant, which is susceptible to the isoxazoline derivative.

(4) The method for cultivation according to (3), wherein the plant having sensitivity to an isoxazoline derivative is a plant of the Gramineae.

(5) The method for cultivation according to (4), wherein the plant of the Gramineae is rice.

(6) The method for cultivation according to (3), wherein the plant having sensitivity to an isoxazoline derivative is a plant of the Brassicaceae, the Leguminosae, the Umbelliferae, the Amaranthaceae, the Labiatae, the Chenopodiaceae, the Rosaceae, the Compositae, the Solanaceae, or the Malvaceae.

(7) The method for cultivation according to (6), wherein the plant of the Brassicaceae is rapeseed (*Brassica napus*) or *Arabidopsis thaliana*.

(8) A method for imparting isoxazoline-derivative resistance comprising introducing a nucleic acid encoding a protein (a) or (b) below into a plant having sensitivity to an isoxazoline derivative:

(a) a protein comprising the amino acid sequence as shown in SEQ ID NO: 2; or (b) a protein comprising an amino acid sequence having 80% or higher identity to the amino acid sequence as shown in SEQ ID NO: 2 and having the activity of glutathione-S-transferase.

(9) The method for imparting resistance according to (8), wherein the isoxazoline derivative is pyroxasulfone and/or fenoxasulfone.

(10) The method for imparting resistance according to (8), wherein the plant having sensitivity to an isoxazoline derivative is a plant of the Gramineae.

(11) The method for imparting resistance according to (10), wherein the plant of the Gramineae is rice.

(12) The method for imparting resistance according to (8), wherein the plant having sensitivity to an isoxazoline derivative is a plant of the Brassicaceae, the Leguminosae, the Umbelliferae, the Amaranthaceae, the Labiatae, the Chenopodiaceae, the Rosaceae, the Compositae, the Solanaceae, or the Malvaceae.

(13) The method for imparting resistance according to (12), wherein the plant of the Brassicaceae is rapeseed (*Brassica napus*) or *Arabidopsis thaliana*.

(14) A method for imparting environmental stress resistance comprising introducing a nucleic acid encoding a protein (a) or (b) below into a plant:

(a) a protein comprising the amino acid sequence as shown in SEQ ID NO: 2; or (b) a protein comprising an amino acid sequence having 80% or higher identity to the amino acid sequence as shown in SEQ ID NO: 2 and having the activity of glutathione-S-transferase.

(15) The method for imparting resistance according to (14), wherein the environmental stress is high temperature stress.

(16) The method for imparting resistance according to (14), wherein the plant has sensitivity to an isoxazoline derivative.

(17) The method for imparting resistance according to (16), wherein the isoxazoline derivative is pyroxasulfone and/or fenoxasulfone.

(18) The method for imparting resistance according to (14), wherein the plant is a plant of the Gramineae.

(19) The method for imparting resistance according to (18), wherein the plant of the Gramineae is rice.

(20) The method for imparting resistance according to (14), wherein the plant is a plant of the Brassicaceae, the Leguminosae, the Umbelliferae, the Amaranthaceae, the Labiatae, the Chenopodiaceae, the Rosaceae, the Compositae, the Solanaceae, or the Malvaceae.

(21) The method for imparting resistance according to (20), wherein the plant of the Brassicaceae is rapeseed (*Brassica napus*) or *Arabidopsis thaliana*.

(22) A transgenic plant into which a nucleic acid encoding a protein (a) or (b) below has been introduced:

(a) a protein comprising the amino acid sequence as shown in SEQ ID NO: 2; or (b) a protein comprising an amino acid sequence having 80% or higher identity to the amino acid sequence as shown in SEQ ID NO: 2 and having the activity of glutathione-S-transferase.

(23) The transgenic plant according to (22), which has resistance to an isoxazoline derivative and/or resistance to environmental stress.

(24) The transgenic plant according to (22), which results from introduction of the nucleic acid into a plant having sensitivity to an isoxazoline derivative.

(25) The transgenic plant according to (23) or (24), wherein the isoxazoline derivative is pyroxasulfone and/or fenoxasulfone.

(26) The transgenic plant according to (23), wherein the environmental stress is high temperature stress.

(27) The transgenic plant according to (24), wherein the plant having sensitivity to an isoxazoline derivative is a plant of the Gramineae.

(28) The transgenic plant according to (27), wherein the plant of the Gramineae is rice.

(29) The transgenic plant according to (24), wherein the plant having sensitivity to an isoxazoline derivative is a plant of the Brassicaceae, the Leguminosae, the Umbelliferae, the Amaranthaceae, the Labiatae, the Chenopodiaceae, the Rosaceae, the Compositae, the Solanaceae, or the Malvaceae.

(30) The transgenic plant according to (29), wherein the plant of the Brassicaceae is rapeseed (*Brassica napus*) or *Arabidopsis thaliana*.

This description contains part or all of the contents as disclosed in the description and/or drawings of Japanese Patent Application No. 2016-132689, based on which the present application claims priority.

Effects of the Invention

The present invention can provide a transgenic plant that has acquired resistance to isoxazoline derivatives, such as pyroxasulfone and fenoxasulfone, and/or resistance to environmental stress, such as high temperature stress. In other words, the present invention can impart a plant having sensitivity to such isoxazoline derivatives with resistance to the isoxazoline derivatives and can impart a plant with environmental stress resistance.

Since the transgenic plant according to the present invention can grow in the presence of the isoxazoline derivatives, such transgenic plant can be stably cultivated and produced with the use of isoxazoline derivatives.

BRIEF DESCRIPTION OF THE DRAWINGS

FIG. 1 schematically shows a structure of the TaQ8GTC0 protein expressing construct for *E. coli*.

FIG. 2 shows a photograph of electrophoresis conducted to confirm the TaQ8GTC0 protein.

FIG. 3 shows chemical formulae representing the VLCFAE-inhibiting herbicides used in the glutathione conjugation activity test.

FIG. 4 shows characteristic diagrams showing the conjugation reaction between pyroxasulfone and glutathione and the HPLC chromatograms when pyroxasulfone is used as the VLCFAE-inhibiting herbicide.

FIG. 5 schematically shows a structure of the vector comprising the TaQ8GTC0 gene for rice transformation.

FIG. 6 shows photographs showing the proliferation of cultured rice cells comprising the TaQ8GTC0 gene introduced therein on selective medium.

FIG. 7-1 shows characteristic diagrams showing the growth of the lineage #3-13 and the wild-type rice on the medium containing VLCFAE-inhibiting herbicide.

FIG. 7-2 shows characteristic diagrams showing the growth of the lineage #3-13 and the wild-type rice on the medium containing VLCFAE-inhibiting herbicide.

FIG. 7-3 shows characteristic diagrams showing the growth of the lineage #3-13 and the wild-type rice on the medium containing VLCFAE-inhibiting herbicide.

FIG. 7-4 shows characteristic diagrams showing the growth of the lineage #3-13 and the wild-type rice on the medium containing VLCFAE-inhibiting herbicide.

FIG. 7-5 shows characteristic diagrams showing the growth of the lineage #3-13 and the wild-type rice on the medium containing VLCFAE-inhibiting herbicide.

FIG. 7-6 shows characteristic diagrams showing the growth of the lineage #3-13 and the wild-type rice on the medium containing VLCFAE-inhibiting herbicide.

FIG. 8 schematically shows a structure of the vector comprising the TaQ8GTC0 gene for *Arabidopsis thaliana* transformation.

FIG. 9 shows photographs showing the conditions of cultivated seeds obtained from *Arabidopsis thaliana* plants into which the TaQ8GTC0 gene had been introduced.

FIG. 10 shows a photograph of electrophoresis conducted to confirm the TaQ8GTC0 gene introduced into *Arabidopsis thaliana*.

FIG. 11 shows characteristic diagrams showing the results of the pyroxasulfone sensitivity test conducted for the wild-type *Arabidopsis thaliana* plant (Columbia-0).

FIG. 12 shows characteristic diagrams showing the results of the pyroxasulfone sensitivity test conducted for the *Arabidopsis thaliana* plant comprising the TaQ8GTC0 gene introduced therein.

FIG. 13 shows characteristic diagrams showing the results of sensitivity of the *Arabidopsis thaliana* plant comprising the TaQ8GTC0 gene introduced therein to the VLCFAE-inhibiting herbicide.

FIG. 14 shows characteristic diagrams showing the results of sensitivity of the *Arabidopsis thaliana* plant comprising the TaQ8GTC0 gene introduced therein to the VLCFAE-inhibiting herbicide.

FIG. 15 shows characteristic diagrams showing the results of the high temperature stress resistance test conducted for the rice plant comprising the TaQ8GTC0 gene introduced therein.

FIG. 16 shows a phylogenetic tree including TaQ8GTC0 and GST having high homology to the TaQ8GTC0.

FIG. 17 schematically shows a structure of a rice transformation vector to express various types of GSTs.

FIG. 18 shows characteristic diagrams showing the fatty acid contents in two lines of cultured rice cells comprising the plant GST genes introduced therein and the control cultured rice cells treated with pyroxasulfone and the control cultured rice cells untreated with pyroxasulfone.

FIG. 19 shows characteristic diagrams showing the fatty acid contents in three types of cultured rice cells comprising the plant GST genes introduced therein and the control cultured rice cells treated with pyroxasulfone and the control cultured rice cells untreated with pyroxasulfone.

FIG. 20 shows characteristic diagrams showing the fatty acid contents in two types of cultured rice cells comprising the plant GST genes introduced therein and the control cultured rice cells treated with pyroxasulfone.

FIG. 21 schematically shows a structure of a rice transformation vector expressing the maize GST gene.

FIG. 22 shows photographs of cultured rice cells comprising the maize GST gene introduced therein.

FIG. 23 shows photographs of the results concerning pyroxasulfone resistance of the cultured rice cells comprising the maize GST gene introduced therein.

FIG. 24 schematically shows cloning of a TaQ8GTC1-R gene.

FIG. 25 shows the comparison of nucleotide sequences between TaQ8GTC1-R gene determined in this experiment (upper line, SEQ ID NO: 31) and TaQ8GTC1 gene on the database (lower line, SEQ ID NO: 33).

FIG. 26 shows the comparison of amino acid sequences between TaQ8GTC1-R determined in this experiment (upper line, SEQ ID NO: 32) and TaQ8GTC1 gene on the database (lower line, SEQ ID NO: 34).

FIG. 27 schematically shows a structure of a TaQ8GTC1-R protein expressing construct for *E. coli*.

FIG. 28 shows a photograph of the electrophoresis conducted to confirm the TaQ8GTC1-R protein.

FIG. 29 shows characteristic diagrams showing the conjugation reaction between pyroxasulfone and glutathione and the HPLC chromatograms when pyroxasulfone is used as the VLCFAE-inhibiting herbicide.

FIG. 30 shows the comparison of the amino acid sequences among plant GSTs. The first line shows AtGSTF2 (SEQ ID NO: 37); the second line shows PttGSTF1 (SEQ ID NO: 38); the third line shows ZmGSTF1 (SEQ ID NO: 39); the fourth line shows TaGSTF1 (SEQ ID NO: 40); the fifth line shows TaGSTF2-R (SEQ ID NO: 32); the sixth line shows TaGSTF3 (SEQ ID NO: 2); the seventh lien shows TaGSTF4 (SEQ ID NO: 41); the eighth line shows TaGSTF5 (SEQ ID NO: 42); and the ninth line shows TaGSTF6 (SEQ ID NO: 43).

FIG. 31 schematically shows a structure of a rice transformation vector of the TaQ8GTC1-R gene.

FIG. 32 shows photographs of the proliferation of cultured rice cells comprising the TaQ8GTC1-R gene introduced therein on selective medium.

FIG. 33 shows characteristic diagrams showing the growth of the rice comprising the TaQ8GTC1-R gene introduced therein on the medium containing pyroxasulfone.

FIG. 34 schematically shows a structure the vector comprising the TaQ8GTC1-R gene for rapeseed transformation.

FIG. 35 shows photographs showing the growth of transgenic rapeseed plants comprising the TaQ8GTC0 gene introduced therein on the medium.

FIG. 36 shows a photograph of electrophoresis conducted to confirm the introduction of TaQ8GTC0 gene into rapeseed plant by PCR.

FIG. 37 shows photographs of the sensitivity of wild-type rapeseed plants (variety: Westar) and rapeseed plants comprising TaQ8GTC0 gene introduced therein to pyroxasulfone applied pre-emergence.

FIG. 38 shows photographs of the sensitivity of wild-type rapeseed plants (variety: Westar) and rapeseed plants comprising TaQ8GTC0 gene introduced therein to pyroxasulfone applied pre-emergence.

FIG. 39 shows photographs of the sensitivity of wild-type rapeseed plants (variety: Westar) and rapeseed plants comprising TaQ8GTC0 gene introduced therein to pyroxasulfone applied pre-emergence.

FIG. 40 shows photographs of the growth of wild-type rapeseed plants (variety: Westar) on the agar medium.

FIG. 41 shows photographs of the growth of rapeseed plants comprising TaQ8GTC0 gene introduced therein on the agar medium.

FIG. 42 shows photographs of the growth of wild-type rapeseed plants (variety: Westar) and rapeseed plants comprising TaQ8GTC0 gene introduced therein on the agar medium FIG. 43 shows characteristic diagrams of the growth inhibition of wild-type rapeseed plants (variety: Westar) and rapeseed plants comprising TaQ8GTC0 gene introduced therein on the agar medium.

FIG. 44 shows characteristic diagrams of the high temperature resistance of wild-type rapeseed plants (variety: Westar) and rapeseed plants comprising TaQ8GTC0 gene introduced therein on the agar medium.

DETAILED DESCRIPTION OF THE INVENTION

Hereafter, the present invention is described in detail.
[Glutathione-S-Transferase of the Present Invention]

The glutathione-S-transferase of the present invention (hereafter, it is occasionally abbreviated as "GST") can be defined as a protein (a) or (b) below:

(a) a protein comprising the amino acid sequence as shown in SEQ ID NO: 2; or (b) a protein comprising an amino acid sequence having 80% or higher identity to the amino acid sequence as shown in SEQ ID NO: 2 and having the activity of glutathione-S-transferase.

The protein comprising the amino acid sequence as shown in SEQ ID NO: 2 is referred to as "GST F3" among GSTs derived from wheat (*Triticum aestivum*), which is identified under Accession Code: Q8GTC0. The amino acid sequence as shown in SEQ ID NO: 2 is identified along with the CDS sequence (SEQ ID NO: 1) under Accession Number: AJ440792_1.

GST that can be used in the present invention is not limited to the protein comprising the amino acid sequence as shown in SEQ ID NO: 2. As described in (b) above, it may be a protein comprising an amino acid sequence having 80% or higher, preferably 85% or higher, more preferably 90% or higher, further preferably 95% or higher, and most preferably 97% or higher identity to the amino acid sequence as shown in SEQ ID NO: 2 and having the activity of glutathione-S-transferase.

The degree of amino acid sequence identity can be determined using the BLASTN or BLASTX Program equipped with the BLAST algorithm (at default settings). The degree of sequence identity is determined by subjecting a pair of amino acid sequences to pairwise alignment analysis, identifying completely identical amino acid residues, and calculating the percentage of all the amino acid residues subjected to comparison accounted for by such completely identical amino acid residues.

GST that can be used in the present invention is not limited to the protein comprising the amino acid sequence as shown in SEQ ID NO: 2. It may be a protein comprising an amino acid sequence derived from the amino acid sequence as shown in SEQ ID NO: 2 by substitution, deletion, insertion, or addition of one or several amino acids and having the activity of glutathione-S-transferase. The term "several" used herein refers to, for example, 2 to 30, preferably 2 to 20, more preferably 2 to 15, further preferably 2 to 10, and still further preferably 2 to 5.

Further, GST that can be used in the present invention may be a protein encoded by DNA hybridizing under stringent conditions to the full-length sequence or a partial sequence of a complementary strand of DNA comprising the nucleotide sequence as shown in SEQ ID NO: 1 and having the activity of glutathione-S-transferase. Under "stringent conditions," so-called specific hybrids are formed, but non-specific hybrids are not formed. Such conditions can be adequately determined with reference to, for example, Molecular Cloning: A Laboratory Manual (Third Edition). Specifically, the degree of stringency can be determined in accordance with the temperature and the salt concentration of a solution used for Southern hybridization and the temperature and the salt concentration of a solution used for the step of washing in Southern hybridization. Under stringent conditions, more specifically, the sodium concentration is 25 to 500 mM and preferably 25 to 300 mM, and the temperature is 42° C. to 68° C. and preferably 42° C. to 65° C., for example. Further specifically, the sodium concentration is 5×SSC (83 mM NaCl, 83 mM sodium citrate), and the temperature is 42° C.

In particular, GST that can be used in the present invention has the activity of glutathione conjugation to the isoxazoline derivative described in detail below. Specifically, GST that can be used in the present invention has the activity for binding the isoxazoline derivative to glutathione.

When GST that can be used in the present invention is expressed in a plant, more specifically, it is capable of accelerating glutathione conjugation to the isoxazoline derivative and lowering the inhibition of a very-long-chain fatty acid elongase caused by the isoxazoline derivative. When GST that can be used in the present invention is expressed in a plant, accordingly, it can impart the plant with resistance to the isoxazoline derivative.

In other word, the activity of glutathione-S-transferase is an activity of glutathione conjugation to the isoxazoline derivative or an activity for binding glutathione to the isoxazoline derivative.

As described above, a protein comprising an amino acid sequence other than the amino acid sequence as shown in SEQ ID NO: 2 can be GST having an activity for lowering the inhibition of a very-long-chain fatty acid elongase caused by the isoxazoline derivative in addition to the activity of glutathione-S-transferase described above. In addition, it can be GST that can impart a plant with resistance to the isoxazoline derivative.

[Transgenic Plants]

The transgenic plant of the present invention is produced via introduction of a gene encoding the GST described above into a given plant (a plant body or a plant cell) in an expressible manner. The transgenic plant of the present invention acquires resistance to isoxazoline derivatives described in detail below and resistance to environmental stress through expression of the GST-encoding gene described above.

When a plant acquires resistance to an isoxazoline derivative, sensitivity of the plant to an isoxazoline derivative becomes lower after the introduction of the GST to a statistically significant level, compared with sensitivity of the plant to an isoxazoline derivative before introduction of the GST. When a plant acquires resistance to an isoxazoline derivative, in other words, inhibitory effects on the plant imposed by an isoxazoline derivative becomes lower after the introduction of the GST to a statistically significant level, compared with the inhibitory effects on the plant before introduction of the GST. Inhibitory effects imposed by an isoxazoline derivative can be evaluated using an indicator, such as so-called the concentration required for 50% inhibition ($IC_{50}$).

When a plant acquires resistance to environmental stress, sensitivity of the plant to environmental stress becomes lower after the introduction of the GST to a statistically significant level, compared with sensitivity of the plant to the same environmental stress before introduction of the GST. When a plant acquires resistance to environmental stress, in other words, the growth rate of the plant becomes faster after the introduction of the GST to a statistically significant level, compared with the growth rate of the plant before introduction of the GST, when plants are cultured with the application of a given level of environmental stress. The plant growth rate can be evaluated using an indicator, such as a plant height or a root weight.

Examples of environmental stress include, but are not particularly limited to, high temperature stress, high salt concentration stress, dehydration stress, and low-temperature stress. Among such various types of environmental stress, the transgenic plant of the present invention is excellent in terms of resistance to high temperature stress.

Targets plants to which the GST is to be introduced are not particularly limited. A plant can acquire resistance to environmental stress, such as resistance to high temperature stress, through introduction of the GST thereinto. It is particularly preferable that a target plant into which the GST is to be introduced be a plant having sensitivity to an isoxazoline derivative described in detail below. By introducing the GST into a plant having sensitivity to an isoxazoline derivative, the resulting plant can acquire resistance to an isoxazoline derivative.

The term "a plant having sensitivity to an isoxazoline derivative" used herein refers to a plant, the growth of which is inhibited when an isoxazoline derivative is used as a herbicide at an optimum concentration. When $IC_{50}$ for pyroxasulfone as an isoxazoline derivative is 200 nM or lower, preferably 100 nM or lower, and more preferably 50 nM, for example, a plant of interest can have sensitivity to pyroxasulfone.

Specific examples of plants having sensitivity to an isoxazoline derivative include: plants of the Gramineae, such as rice, barley, sorghum, oat, durum wheat, and maize; plants of the Brassicaceae, such as Brassica (*Brassica rapa*), rapeseed (*Brassica napus*), cabbage, Canola, kale, white mustard, turnip, and *Arabidopsis thaliana*; plants of the Leguminosae, such as alfalfa, bush bean, soybean, adzuki bean, mung bean, and *Trifolium repens*; plants of the Umbelliferae, such as *Anethum graveolens*, fennel, and parsley; plants of the Amaranthaceae, such as spinach and beet; plants of the Labiatae, such as basil; plants of the Chenopodiaceae, such as Swiss chard; plants of the Rosaceae, such as plum; plants of the Compositae, such as lettuce; plants of the Solanaceae, such as tomato; and plants of the Malvaceae, such as cotton, although examples are not particularly limited thereto.

The GST described above is introduced into any of the plants specifically exemplified above. Thus, resistance to an isoxazoline derivative can be imparted to the plants, and resistance to environmental stress can be enhanced.

The conjugation activity of the GST described above to an isoxazoline derivative is particularly high among VLCFAE-inhibiting herbicides, and such activity is higher than the conjugation activity to metolachlor reported in the literature (I. Cummins et al., Plant Mol. Biol., 52, 591-603, 2003) to a statistically significant level. Thus, transgenic plants comprising the GST introduced therein can be cultivated with the use of isoxazoline derivatives as herbicides among VLCFAE-inhibiting herbicides.

Also, transgenic plants comprising the GST introduced therein are excellent in terms of resistance to environmental stress. Thus, such transgenic plants can be cultivated under the environment in which plant growth had been impaired by environmental stress in the past. In particular, the transgenic plants comprising the GST introduced therein are excellent in terms of resistance to high temperature stress among various types of environmental stress. Thus, transgenic plants comprising the GST introduced therein can be cultivated in areas or in seasons that had not been suitable for plant growth due to high temperature in the past.

A method for producing a transgenic plant of the present invention is not particularly limited. In summary, a nucleic acid encoding the GST described above may be incorporated into an expression vector, and the resulting expression vector may then be introduced into a plant. Thus, a transgenic plant expressing the GST of interest can be produced.

An expression vector is constructed to contain a promoter that enables expression within plants and a nucleic acid encoding the GST described above. As a vector serving as a base for the expression vector, various conventionally known vectors can be used. For example, plasmids, phages, cosmids, or the like can be used and such vectors can be appropriately selected depending on plant cells into which they are introduced and introduction methods. Specific examples of such vectors include pBR322, pBR325, pUC19, pUC119, pBluescript, pBluescriptSK, and pBI vectors. When a method for introduction of a vector into a plant uses *Agrobacterium*, in particular, a pBI binary vector is preferably used. Specific examples of such pBI binary vector include pBIG, pBIN19, pBI101, and pBI121.

A promoter to be used herein is not particularly limited, as long as it enables expression of a nucleic acid encoding the GST described above in a plant. Any known promoter can be appropriately used. Use of a constitutive expression promoter that can express a downstream gene constitutively in a plant is particularly preferable. Examples of such promoter include a cauliflower mosaic virus 35S promoter (CaMV35S), various actin gene promoters, various ubiquitin gene promoters, a nopaline synthase gene promoter, a tobacco PR1a gene promoter, a tomato ribulose 1,5-bisphosphate carboxylase/oxidase small subunit gene promoter, and a napin gene promoter. Of these, a cauliflower mosaic virus 35S promoter, an actin gene promoter, or a ubiquitin gene promoter can be more preferably used. The use of each of the above promoters enables strong expression of any gene when it is introduced into plant cells.

Also, a promoter having functions of causing site-specific expression in a plant can be used herein. As such a promoter, any conventionally known promoter can be used. The use of such a promoter enables site-specific expression of the GST.

An expression vector may further contain other DNA segments, in addition to a promoter and the nucleic acid encoding the GST. Such other DNA segments are not particularly limited, and examples thereof include a terminator, a selection marker, an enhancer, and a nucleotide sequence for enhancing translation efficiency. Also, the above expression vector may further have a T-DNA region. A T-DNA region can enhance efficiency for gene introduction particularly when the above recombinant expression vector is introduced into a plant using *Agrobacterium*.

A transcription terminator is not particularly limited, as long as it functions as a transcription termination site, and any known transcription terminator may be used. For example, specifically, a transcription termination region (Nos terminator) of a nopaline synthase gene, a transcription termination region (CaMV35S terminator) of cauliflower mosaic virus 35S, or the like can be preferably used. Of these, the Nos terminator can be more preferably used. In the case of the above expression vector, a phenomenon such that an unnecessarily long transcript is synthesized can be prevented by arranging a transcription terminator at an appropriate position after it is introduced into plant cells.

As a transformant selection marker, a drug resistance gene can be used, for example. Specific examples of such drug resistance gene include drug resistance genes against hygromycin, bleomycin, kanamycin, gentamicin, chloramphenicol, and the like. Transformed plants can be easily selected by selecting plants that can grow in medium containing the above antibiotics. In addition, a mutant acetolactate synthase gene that imparts resistance to a given drug can be used as a transformant selection marker.

A method for constructing an expression vector is not particularly limited. To an appropriately selected vector serving as a base, the above promoter, the nucleic acid encoding the GST, and if necessary, the above other DNA segments may be introduced in a predetermined order. For example, the nucleic acid encoding the GST and a promoter (and, if necessary, a transcription terminator or the like) are linked to construct an expression cassette and the cassette may then be introduced into a vector. In construction of an expression cassette, for example, cleavage sites of DNA segments are prepared to have protruding ends complementary to each other, and a reaction with a ligation enzyme is then performed. Thus, the order of the DNA segments can be specified. When an expression cassette contains a terminator, in addition, DNA segments may be arranged in the following order from upstream: a promoter, the nucleic acid encoding the GST, and a terminator. Also, reagents for construction of an expression vector (that is, types of restriction enzymes, ligation enzymes, and the like) are not particularly limited, and commercially available reagents can be appropriately selected and used.

Also, a method for replicating (a method for producing) the above expression vector is not particularly limited and conventionally known replication methods can be used herein. In general, such expression vector may be replicated within *Escherichia coli* as a host. At this time, preferred types of *Escherichia coli* may be selected depending on the types of vector.

The above-described expression vector is introduced into a target plant by a general transformation method. A method for introducing an expression vector into plant cells (transformation method) is not particularly limited. Conventionally known appropriate introduction methods can be used depending on plant cells. Specifically, a method using *Agrobacterium* or a method that involves direct introduction into plant cells can be used, for example. As a method for directly introducing an expression vector into plant cells, microinjection, electroporation, a polyethylene glycol method, a particle gun method, protoplast fusion, a calcium phosphate method, or the like can be employed.

When a method for directly introducing DNA into plant cells is employed, also, DNA that can be used herein contains transcriptional units required for the expression of a target gene, such as a promoter and a transcription terminator, and a nucleic acid encoding the GST. Vector functions are not essential. Moreover, a DNA that contains a GST-coding region alone but does not contain a transcriptional unit may be used herein, as long as it is integrated into a host's transcriptional unit and is capable of expressing the target GST.

Examples of plant cells into which the above expression vector or an expression cassette that do not contain an expression vector but contains a nucleic acid encoding the target GST is to be introduced include cells of each tissue of plant organs, such as flowers, leaves, and roots, calluses, and suspension-cultured cells. At this time, an appropriate expression vector may be constructed according to the types of plant to be produced or a versatile expression vector may be constructed in advance and then introduced into plant cells.

Tumor tissues, shoots, and hairy roots obtained as a result of transformation can be directly used in cell culture, tissue culture, or organ culture. Also, a plant hormone, such as auxin, cytokinin, gibberellin, abscisic acid, ethylene, or brassinoride, is administered thereto at an adequate concentration with the use of a conventional plant tissue culture method, and a plant body can be reproduced therefrom.

A reproduction method that is employed herein comprises transferring callus-form transformed cells to a medium having a different hormone at a different concentration, culturing the transformed cells to form adventitious embryos, and obtaining an entire plant body. Examples of the medium to be used herein include an LS medium and an MS medium.

The transgenic plant of the present invention encompasses a progeny plant that is obtained by introducing an expression vector comprising a nucleic acid encoding the GST into a host cell to obtain a transformed plant cell, reproducing a transformed plant body from the transformed plant cell, obtaining a plant seed from the transformed plant body, and producing a plant body from the plant seed. To obtain plant seeds from a transformed plant body, for example, the transformed plant body is collected from a rooting medium, the collected transformed plant body is transferred to a pot containing water-containing soil therein, allowing the transformed plant body to grow at constant temperature, so as to form flowers, and forming seeds in the end. A plant body is produced from seeds by, for example, isolating seeds upon maturation thereof formed on a transformed plant body, seeding the seeds in water-containing soil, and growing the seeds at constant temperature under illumination. The plant thus produced expresses the GST, and it thus exhibits resistance to an isoxazoline derivative and resistance to environmental stress.

[Isoxazoline Derivative]

In the present invention, the term "isoxazoline derivative" refers to a compound having an isoxazoline moiety and a salt thereof. The herbicidal activity of an isoxazoline derivative is reported in, for example, JP H08-225548 A, JP H09-328477 A, and JP H09-328483 A. Specifically, isoxazoline derivatives that have already been reported can be used as herbicides.

JP Patent No. 4,465,133 discloses isoxazoline derivatives and, in particular, compounds exhibiting herbicidal effects and selectivity between crops and weeds. Isoxazoline derivatives disclosed in JP Patent No. 4,465,133 include pyroxasulfone (compound name: 3-[5-(difluoromethoxy)-1-methyl-3-(trifluoromethyl)pyrazol-4-ylmethylsulfonyl]-4,5-dihydro-5,5-dimethyl-1,2-oxazole).

More specifically, JP Patent No. 4,465,133 discloses isoxazoline derivatives (1) to (17) below.

(1) An isoxazoline derivative represented by General Formula [I] or a pharmacologically acceptable salt thereof:

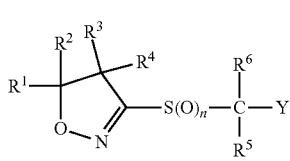

wherein $R^1$ and $R^2$, which may be the same or different, each represent a hydrogen atom, a C1 to C10 alkyl group, a C3 to C8 cycloalkyl group, or a C3 to C8 cycloalkyl C1 to C3 alkyl group, or $R^1$ and $R^2$ may be bound to each other to form a C3 to C7 spiro ring together with the carbon atoms to which they bind;

$R^3$ and $R^4$, which may be the same or different, each represent a hydrogen atom, a C1 to C10 alkyl group, or a C3 to C8 cycloalkyl group, or $R^3$ and $R^4$ may be bound to each other to form a C3 to C7 spiro ring together with the carbon atoms to which they bind, or $R^1$, $R^2$, $R^3$, and $R^4$ may form a 5- to 8-membered ring together with the carbon atoms to which they bind;

$R^5$ and $R^6$, which may be the same or different, each represent a hydrogen atom or a C1 to C10 alkyl group;

Y represents a 5- to 6-membered aromatic heterocyclic group or condensed aromatic heterocyclic group having any hetero atoms selected from among a nitrogen atom, an oxygen atom, and a sulfur atom, the heterocyclic group may be substituted with the same or different 0 to 6 groups selected from among the substituent group α described below, two alkyl groups, two alkoxy groups, an alkyl group and an alkoxy group, an alkyl group and an alkylthio group, an alkyl group and an alkylsulfonyl group, an alkyl group and a monoalkylamino group, or an alkyl group and a dialkylamino group adjacent to each other may together form a 5- to 8-membered ring, which may be substituted with 1 to 4 halogen atoms, or when the hetero atom of the heterocyclic group is a nitrogen atom, the hetero atom of the heterocyclic group may be oxidized to become N-oxide; and n is an integer of 0 to 2.

In the substituent groups described below, "an optionally substituted phenyl group, an optionally substituted phenoxy group, an optionally substituted phenylthio group, an optionally substituted aromatic heterocyclic group, an optionally substituted aromatic heterocyclic oxy group, an optionally substituted aromatic heterocyclic thio group, an optionally substituted phenylsulfinyl group, an optionally substituted phenylsulfonyl group, an optionally substituted aromatic heterocyclic sulfonyl group, an optionally substituted phenylsulfonyloxy group, an optionally substituted benzylcarbonyl group, an optionally substituted benzoyl group, an optionally substituted benzyloxycarbonyl group, an optionally substituted phenoxycarbonyl group, an optionally substituted benzyloxycarbonyloxy group, or an optionally substituted benzoyloxy group" may be substituted with a halogen atom, a C1 to C10 alkyl group, a C1 to C4 haloalkyl group, a C1 to C10 alkoxyalkyl group, a C1 to C10 alkoxy group, a C1 to C10 alkylthio group, a C1 to C10 alkylsulfonyl group, an acyl group, a C1 to C10 alkoxycarbonyl group, a cyano group, a carbamoyl group (the nitrogen atom thereof may be substituted with the same or different C1 to C10 alkyl group), a nitro group, or an amino group (the nitrogen atom thereof may be substituted with the same or different C1 to C10 alkyl group, C1 to C6 acyl group, C1 to C4 haloalkylcarbonyl group, C1 to C10 alkylsulfonyl group, or C1 to C4 haloalkylsulfonyl group).

"Substituent Group α"

A hydroxyl group, a thiol group, a halogen atom, a C1 to C10 alkyl group, a C1 to C10 alkyl group mono-substituted with a group selected from among the substituent group β, a C1 to C4 haloalkyl group, a C3 to C8 cycloalkyl group, a C1 to C10 alkoxy group, a C1 to C10 alkoxy group mono-substituted with a group selected from among the substituent group γ, a C1 to C4 haloalkoxy group, a C3 to C8 cycloalkyloxy group, a C3 to C8 cycloalkyl C1 to C3 alkyloxy group, a C1 to C10 alkylthio group, a C1 to C10 alkylthio group mono-substituted with a group selected from among the substituent group γ, a C1 to C4 haloalkyl thio group, a C2 to C6 alkenyl group, a C2 to C6 alkenyloxy group, a C2 to C6 alkynyl group, a C2 to C6 alkynyloxy group, a C1 to C10 alkylsulfinyl group, a C1 to C10 alkylsulfinyl group mono-substituted with a group selected from among the substituent group γ, a C1 to C10 alkylsulfonyl group, a C1 to C10 alkylsulfonyl group mono-substituted with a group selected from among the substituent group γ, a C1 to C4 haloalkylsulfinyl group, a C1 to C10 alkylsulfonyloxy group mono-substituted with a group selected from among the substituent group γ, a C1 to C4 haloalkylsulfonyl group, a C1 to C10 alkylsulfonyloxy group, a C1 to C4 haloalkylsulfonyloxy group, an optionally substituted phenyl group, an optionally substituted phenoxy group, an optionally substituted phenylthio group, an optionally substituted aromatic heterocyclic group, an optionally substituted aromatic heterocyclic oxy group, an optionally substituted aromatic heterocyclic thio group, an optionally substituted phenylsulfinyl group, an optionally substituted phenylsulfonyl group, an optionally substituted aromatic heterocyclic sulfonyl group, an optionally substituted phenylsulfonyloxy group, an acyl group, a C1 to C4 haloalkylcarbonyl group, an optionally substituted benzylcarbonyl group, an optionally substituted benzoyl group, a carboxyl group, a C1 to C10 alkoxycarbonyl group, an optionally substituted benzyloxycarbonyl group, an optionally substituted phenoxycarbonyl groups, a cyano group, a carbamoyl group (the nitrogen atom thereof may be substituted with the same or different C1 to C10 alkyl group or optionally substituted phenyl group), a C1 to C6 acyloxy group, a C1 to C4 haloalkylcarbonyloxy group, an optionally substituted benzyloxycarbonyloxy group, an optionally substituted benzoyloxy group, a nitro group, and an amino group (the nitrogen atom thereof may be substituted with the same or different C1 to C10 alkyl group, an optionally substituted phenyl group, a C1 to C6 acyl group, a C1 to C4 haloalkylcarbonyl group, an optionally substituted benzylcarbonyl group, an optionally substituted benzoyl group, a C1 to C10 alkylsulfonyl group, a C1 to C4 haloalkylsulfonyl group, an optionally substituted benzylsulfonyl group, or an optionally substituted phenylsulfonyl group).

"Substituent Group β"

A hydroxyl group, a C3 to C8 cycloalkyl group, which may be substituted with a halogen atom or alkyl group), a C1 to C10 alkoxy group, a C1 to C10 alkylthio group, a C1 to C10 alkylsulfonyl group, a C1 to C10 alkoxycarbonyl group, a C2 to C6 haloalkenyl group, an amino group (the nitrogen atom thereof may be substituted with the same or different C1 to C10 alkyl group, C1 to C6 acyl group, C1 to C4 haloalkylcarbonyl group, C1 to C10 alkylsulfonyl group, or C1 to C4 haloalkylsulfonyl group), a carbamoyl group (the nitrogen atom thereof may be substituted with the same or different C1 to C10 alkyl group), a C1 to C6 acyl group, a C1 to C4 haloalkylcarbonyl group, a C1 to C10 alkoxyimino group, a cyano group, an optionally substituted phenyl group, and an optionally substituted phenoxy group.

"Substituent Group γ"

A C1 to C10 alkoxycarbonyl group, an optionally substituted phenyl group, an optionally substituted aromatic heterocyclic group, a cyano group, and a carbamoyl group (the nitrogen atom thereof may be substituted with the same or different C1 to C10 alkyl group).

(2) The isoxazoline derivative according to (1), wherein the substituent group α on the heterocycle, which may be substituted with the same or different 0 to 6 groups, includes a hydroxyl group, a halogen atom, a C1 to C10 alkyl group, a C1 to C10 alkyl group mono-substituted with a group selected from among the substituent group β, a C1 to C4 haloalkyl group, a C3 to C8 cycloalkyl group, a C1 to C10 alkoxy group, a C1 to C10 alkoxy group mono-substituted with a group selected from among the substituent group γ, a C1 to C4 haloalkoxy group, a C3 to C8 cycloalkyloxy group, a C3 to C8 cycloalkyl C1 to C3 alkyloxy group, a C1 to C10 alkylthio group, a C1 to C10 alkylthio group mono-substituted with a group selected from among the substituent group γ, a C1 to C4 haloalkyl thio group, a C2 to C6 alkenyl group, a C2 to C6 alkenyloxy group, a C2 to C6 alkynyl group, a C2 to C6 alkynyloxy group, a C1 to C10 alkylsulfonyl group, a C1 to C4 haloalkylsulfonyl group, an optionally substituted phenyl group, an optionally substituted phenoxy group, an optionally substituted phenylthio group, an optionally substituted aromatic heterocyclic group, an optionally substituted aromatic heterocyclic oxy group, an optionally substituted aromatic heterocyclic thio group, an optionally substituted phenylsulfonyl group, an optionally substituted aromatic heterocyclic sulfonyl group, a C1 to C6 acyl group, a C1 to C4 haloalkylcarbonyl group, an optionally substituted benzylcarbonyl group, an optionally substituted benzoyl group, a carboxyl group, a C1 to C10 alkoxycarbonyl group, a cyano group, a carbamoyl group (the nitrogen atom thereof may be substituted with the same or different C1 to C10 alkyl group or an optionally substituted phenyl group), a nitro group, an amino group (the nitrogen atom thereof may be substituted with the same or different C1 to C10 alkyl group, an optionally substituted phenyl group, a C1 to C6 acyl group, a C1 to C4 haloalkylcarbonyl group, an optionally substituted benzylcarbonyl group, an optionally substituted benzoyl group, a C1 to C10 alkylsulfonyl group, a C1 to C4 haloalkylsulfonyl group, an optionally substituted benzylsulfonyl group, or an optionally substituted phenylsulfonyl group), two alkyl groups, two alkoxy groups, an alkyl group and an alkoxy group, an alkyl group and an alkylthio group, an alkyl group and an alkylsulfonyl group, an alkyl group and a monoalkylamino group, or an alkyl group and a dialkylamino group adjacent to each other may together form a 5- to 8-membered ring, which may be substituted with 1 to 4 halogen atoms.

(3) The isoxazoline derivative according to (2), wherein the substituent group α on the heterocycle, which may be substituted with the same or different 0 to 6 groups, includes a halogen atom, a C1 to C10 alkyl group, a C1 to C4 haloalkyl group, a C1 to C10 alkoxy C1 to C3 alkyl group, a C3 to C8 cycloalkyl group, which may be substituted with a halogen atom or alkyl group, a C1 to C10 alkoxy group, a C1 to C4 haloalkoxy group, a C3 to C8 cycloalkyl C1 to C3 alkyloxy group, an optionally substituted phenoxy group, a C1 to C10 alkylthio group, a C1 to C10 alkylsulfonyl group, an acyl group, a C1 to C4 haloalkylcarbonyl group, a C1 to C10 alkoxycarbonyl group, a cyano group, or a carbamoyl group (the nitrogen atom thereof may be substituted with the same or different C1 to C10 alkyl group).

(4) The isoxazoline derivative according to any of (1), (2) or (3), wherein $R^1$ and $R^2$, which may be the same or different, each represent a methyl group or an ethyl group; and $R^3$, $R^4$, $R^5$, and $R^6$ each represent a hydrogen atom.

(5) The isoxazoline derivative according to any of (1), (2), (3) or (4), wherein Y represents a 5- or 6-membered aromatic heterocyclic group having any hetero atom selected from among a nitrogen atom, an oxygen atom, and a sulfur atom.

(6) The isoxazoline derivative according to (5), wherein Y represents a thienyl group, a pyrazolyl group, an isoxazolyl group, an isothiazolyl group, a pyridyl group, or a pyrimidinyl group.

(7) The isoxazoline derivative according to (6), wherein Y represents a thiophen-3-yl group, a pyrazol-4-yl group, a pyrazol-5-yl group, an isoxazol-4-yl group, an isothiazol-4-yl group, a pyridine-3-yl group, or a pyrimidin-5-yl group.

(8) The isoxazoline derivative according to (7), wherein Y represents a thiophen-3-yl group and the thiophene ring is definitely substituted at the 2- and 4-positions with the substituent group α.

(9) The isoxazoline derivative according to (7), wherein Y represents a pyrazol-4-yl group and the pyrazole ring is definitely substituted at the 3- and 5-positions with the substituent group α and at the 1-position with a hydrogen atom, a C1 to C10 alkyl group, a C1 to C10 alkyl group mono-substituted with a group selected from among the substituent group β, a C1 to C4 haloalkyl group, a C3 to C8 cycloalkyl group, a C2 to C6 alkenyl group, a C2 to C6 alkynyl group, a C1 to C10 alkylsulfinyl group, a C1 to C10 alkylsulfonyl group, a C1 to C10 alkylsulfonyl group mono-substituted with a group selected from among the substituent group γ, a C1 to C4 haloalkylsulfonyl group, an optionally substituted phenyl group, an optionally substituted aromatic heterocyclic group, an optionally substituted phenylsulfonyl group, an optionally substituted aromatic heterocyclic sulfonyl group, an acyl group, a C1 to C4 haloalkylcarbonyl group, an optionally substituted benzylcarbonyl group, an optionally substituted benzoyl group, a C1 to C10 alkoxycarbonyl group, an optionally substituted benzyloxycarbonyl group, an optionally substituted phenoxycarbonyl group, a carbamoyl group (the nitrogen atom thereof may be substituted with the same or different C1 to C10 alkyl group or an optionally substituted phenyl group), and an amino group (the nitrogen atom thereof may be substituted with the same or different C1 to C10 alkyl group, an optionally substituted phenyl group, an acyl group, a C1 to C4 haloalkylcarbonyl group, an optionally substituted benzylcarbonyl group, an optionally substituted benzoyl group, a C1 to C10 alkylsulfonyl group, a C1 to C4 haloalkylsulfonyl group, an optionally substituted benzylsulfonyl group, or an optionally substituted phenylsulfonyl group).

(10) The isoxazoline derivative according to (7), wherein Y represents a pyrazol-5-yl group and the pyrazole ring is definitely substituted at the 4-position with the substituent group α and at the 1-position with a hydrogen atom, a C1 to C10 alkyl group, a C1 to C10 alkyl group mono-substituted with a group selected from among the substituent group β, a C1 to C4 haloalkyl group, a C3 to C8 cycloalkyl group, a C2 to C6 alkenyl group, a C2 to C6 alkynyl group, a C1 to C10 alkylsulfinyl group, a C1 to C10 alkylsulfonyl group, a C1 to C10 alkylsulfonyl group mono-substituted with a group selected from among the substituent group γ, a C1 to C4 haloalkylsulfonyl group, an optionally substituted phenyl group, an optionally substituted aromatic heterocyclic group, an optionally substituted phenylsulfonyl group, an optionally substituted aromatic heterocyclic sulfonyl group, an acyl group, a C1 to C4 haloalkylcarbonyl group, an optionally substituted benzylcarbonyl group, an optionally substituted benzoyl group, a C1 to C10 alkoxycarbonyl group, an optionally substituted benzyloxycarbonyl group, an optionally substituted phenoxycarbonyl group, a carbamoyl group (the nitrogen atom thereof may be substituted with the same or different C1 to C10 alkyl group or an optionally substituted phenyl group), and an amino group (the nitrogen atom thereof may be substituted with the same or different C1 to C10 alkyl group, an optionally substituted phenyl group, an acyl group, a C1 to C4 haloalkylcarbonyl group, an optionally substituted benzylcarbonyl group, an optionally substituted benzoyl group, a C1 to C10 alkylsulfonyl group, a C1 to C4 haloalkylsulfonyl group, an optionally substituted benzylsulfonyl group, or an optionally substituted phenylsulfonyl group).

(11) The isoxazoline derivative according to (7), wherein Y represents an isoxazol-4-yl group and the isoxazole ring is definitely substituted at the 3- and 5-positions with the substituent group α.

(12) The isoxazoline derivative according to (7), wherein Y represents an isothiazol-4-yl group and the isothiazole ring is definitely substituted at the 3- and 5-positions with the substituent group α.

(13) The isoxazoline derivative according to (7), wherein Y represents a pyridin-3-yl group and the pyridine ring is definitely substituted at the 2- and 4-positions with the substituent group α.

(14) The isoxazoline derivative according to (7), wherein Y represents a pyrimidin-5-yl group and the pyrimidine ring is definitely substituted at the 4- and 6-positions with the substituent group α.

(15) The isoxazoline derivative according to any of (1) to (14), wherein n is an integer of 2.

(16) The isoxazoline derivative according to any of (1) to (14), wherein n is an integer of 1.

(17) The isoxazoline derivative according to any of (1) to (14), wherein n is an integer of 0.

In addition, JP Patent No. 4,299,483 discloses isoxazoline derivatives and, in particular, compounds exhibiting herbicidal effects and selectivity between crops and weeds. Isoxazoline derivatives disclosed in JP Patent No. 4,299,483 include fenoxasulfone (compound name: 3-[(2,5-dichloro-4-ethoxybenzyl)sulfonyl]-4,5-dihydro-5,5-dimethyl-1,2-oxazole).

More specifically, JP Patent No. 4,299,483 discloses isoxazoline derivatives (18) to (20) described below and salts thereof.

(18) An isoxazoline derivative represented by General Formula [I] or a salt thereof:

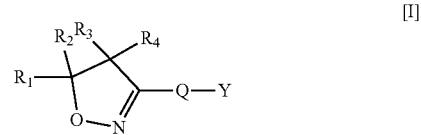

wherein

Q is a group represented by —S(O)n-(CR$_5$R$_6$)m- (wherein n is an integer of 0 to 2, m is an integer of 1 to 3, and R$_5$ and R$_6$ each independently represent a hydrogen atom, a cyano group, an alkoxycarbonyl group, or a C1 to C6 alkyl group);

R$_1$ and R$_2$ represent a hydrogen atom, a C3 to C8 cycloalkyl group, a C1 to C6 alkoxy group, a C1 to C6 alkylcarbonyl group, a C1 to C6 alkylthio group, a C1 to C6 alkylsulfinyl group, a C1 to C6 alkylsulfonyl group, a C1 to C6 alkylamino group, a di(C1 to C6 alkyl)amino group, a cyano group, a C1 to C6 alkoxycarbonyl group, a C1 to C6 alkylaminocarbonyl group, a di(C1 to C6 alkyl)aminocarbonyl group, a (C1 to C6 alkylthio)carbonyl group, a carboxyl group, which may be substituted with 1 to 5 halogen atoms, a C1 to C6 alkyl group, or a C1 to C6 alkoxy group, a benzyloxy group, which may be substituted with 1 to 5 halogen atoms, a C1 to C6 alkyl group, or a C1 to C6 alkoxy group, a phenoxy group, which may be substituted with 1 to 5 halogen atoms, a C1 to C6 alkyl group, or a C1 to C6 alkoxy group), or a phenyl group, which may be substituted with 1 to 5 halogen atoms, a C1 to C6 alkyl group, or a C1 to C6 alkoxy group; a C1 to C8 alkyl group, a C3 to C8 cycloalkyl group; a C1 to C6 alkoxycarbonyl group; a C1 to C6 alkylaminocarbonyl group; a di(C1 to C6 alkyl)aminocarbonyl group; a (C1 to C6 alkylthio)carbonyl group; a carboxyl group; or a phenyl group, which may be substituted with 1 to 5 halogen atoms, a C1 to C6 alkyl group, or a C1 to C6 alkoxy group; or R$_1$ and R$_2$ may form a C3 to C7 spiro ring together with the carbon atom to which they bind, provided that R$_1$ and R$_2$ do not simultaneously represent hydrogen atoms;

R$_3$ and R$_4$ each represent a hydrogen atom; a C1 to C8 alkyl group, which may be substituted with the same or different 1 to 3 halogen atoms, a C3 to C8 cycloalkyl group, or a C1 to C6 alkoxy group; or a C3 to C8 cycloalkyl group, and R$_3$ and R$_4$ may form a C3 to C7 spiro ring together with the carbon atom to which they bind, or R$_1$, R$_2$, R$_3$, and R$_4$ may form a 5- to 8-membered ring together with the carbon atoms to which they bind;

Y represents a hydrogen atom; a C1 to C6 alkoxycarbonyl group; a C2 to C6 alkenyl group; a C1 to C10 alkyl group, which may be substituted with the same or different 1 to 3 halogen atoms, a C1 to C6 alkoxy group, a C2 to C6 alkenyloxy group, a C2 to C6 alkynyloxy group, a benzyloxy group, which may be substituted with 1 to 5 halogen atoms, a C1 to C6 alkyl group, or a C1 to C6 alkoxy group, a C1 to C6 alkoxycarbonyl group, a carboxyl group, a hydroxyl group, or a formyl group; or a phenyl group substituted with the same or different 1 to 5 R$_7$s; and R$_7$ represents a hydrogen atom; a C1 to C6 alkyl group, which may be substituted with the same or different 1 to 3 halogen atoms, a C1 to C6 alkoxy group, a hydroxyl group, a C1 to C6 alkylthio group, a C1 to C6 alkylsulfinyl group, a C1 to C6 alkylsulfonyl group, a C1 to C6 alkylamino group, a di(C1 to C6)alkylamino group, a cyano group, or a phenoxy group, which may be substituted with 1 to 5 halogen atoms, a C1 to C6 alkyl group, or a C1 to C6 alkoxy group; a C1 to C6 alkoxy group, which may be substituted with the same or different 1 to 3 halogen atoms, a C1 to C6 alkoxy group, a C2 to C6 alkenyl group, a C2 to C6 alkynyl group, a C1 to C6 alkoxycarbonyl group, a C1 to C6 alkylcarbonyl group, or a C3 to C8 cycloalkyl group; a C2 to C6 alkenyl group; a C3 to C8 cycloalkyloxy group; a C1 to C6 alkylthio group, which may be substituted with the same or different 1 to 3 halogen atoms, or a C1 to C6 alkoxy group; a C1 to C6 alkylsulfinyl group, which may be substituted with the same or different 1 to 3 halogen atoms or a C1 to C6 alkoxy group; a C1 to C6 alkylsulfonyl group, which may be substituted with the same or different 1 to 3 halogen atoms or a C1 to C6 alkoxy group; a benzyloxy group, which may be substituted with 1 to 5 of halogen atoms, C1 to C6 alkyl groups, or a C1 to C6 alkoxy group; an amino group, which may be substituted with a C1 to C6 alkyl group, a C1 to C6 alkylsulfonyl group, a C1 to C6 alkylcarbonyl (C1 to C6 alkyl) group, or a C1 to C6 alkylsulfonyl (C1 to C6 alkyl) group; a di(C1 to C6 alkyl) amino group; a halogen atom; a cyano group; a nitro group; a C1 to C6 alkoxycarbonyl group; a C3 to C8 cycloalkyl oxycarbonyl group; a carboxyl group; a C2 to C6 alkenyloxycarbonyl group; a C2 to C6 alkynyloxycarbonyl group; a benzyloxycarbonyl group, which may be substituted with 1 to 5 of halogen atoms, C1 to C6 alkyl groups, or C1 to C6 alkoxy groups; a phenoxycarbonyl group, which may be substituted with 1 to 5 of halogen atoms, C1 to C6 alkyl groups, or C1 to C6 alkoxy groups; or a C1 to C6 alkylcarbonyl oxy group.

(19) The isoxazoline derivative represented by General Formula [I] in (18) above or a salt thereof,
wherein,
Q is a group represented by —S(O)n-($CR_5R_6$)m- (wherein n is an integer of 0 to 2, m is 1, and $R_5$ and $R_6$ each represent a hydrogen atom);

$R_1$ and $R_2$ each represent a hydrogen atom; a C1 to C8 alkyl group, which may be substituted with a C3 to C8 cycloalkyl group or a C1 to C6 alkoxy group; or a C3 to C8 cycloalkyl group, or $R_1$ and $R_2$ may form a C3 to C7 spiro ring together with the carbon atom to which they bind, provided that $R_1$ and $R_2$ do not simultaneously represent hydrogen atoms;

$R_3$ and $R_4$ each represent a hydrogen atom or a C1 to C8 alkyl group, which may be substituted with the same or different 1 to 3 halogen atoms, a C3 to C8 cycloalkyl group, or a C1 to C6 alkoxy group, $R_3$ and $R_4$ may form a C3 to C7 spiro ring together with the carbon atom to which they bind, or $R_1$, $R_2$, $R_3$, and $R_4$ may form a 5- to 8-membered ring together with the carbon atoms to which they bind;

Y represents a phenyl group substituted with the same or different 1 to 5 $R_7$s; and $R_7$ represents a hydrogen atom; a C1 to C6 alkyl group, which may be substituted with the same or different 1 to 3 halogen atoms, a C1 to C6 alkoxy group, a hydroxyl group, a C1 to C6 alkylthio group, a C1 to C6 alkylsulfinyl group, a C1 to C6 alkylsulfonyl group, a C1 to C6 alkylamino group, a di(C1 to C6)alkylamino group, a cyano group, or a phenoxy group, which may be substituted with 1 to 5 of halogen atoms, C1 to C6 alkyl groups, or C1 to C6 alkoxy groups; a C1 to C6 alkoxy group, which may be substituted with the same or different 1 to 3 halogen atoms, a C1 to C6 alkoxy group, a C2 to C6 alkenyl group, a C2 to C6 alkynyl group, a C1 to C6 alkoxycarbonyl group, a C1 to C6 alkylcarbonyl groups, or a C3 to C8 cycloalkyl group; a C3 to C8 cycloalkyloxy group; or a halogen atom.

(20) The isoxazoline derivative represented by General Formula [I] in (18) above or a salt thereof,
wherein
Q is a group represented by —S(O)n-($CR_5R_6$)m- (wherein n is an integer of 0 to 2, m is 1, and $R_5$ and $R_6$ each represent a hydrogen atom);

$R_1$ and $R_2$ each represent a C1 to C8 alkyl group;

$R_3$ and $R_4$ each represent a hydrogen atom;

Y represents a phenyl group substituted with the same or different 1 to 5 $R_7$s; and $R_7$ represents a hydrogen atom; a C1 to C6 alkyl group, which may be substituted with the same or different 1 to 3 halogen atoms or C1 to C6 alkoxy groups; a C1 to C6 alkoxy group, which may be substituted with the same or different 1 to 3 halogen atoms or a C1 to C6 alkoxy group; or a halogen atom.

The GST described above has the activity for conjugating to the isoxazoline derivatives that have already been reported. Accordingly, it can be said that transgenic plants comprising the GST introduced therein have resistance to the isoxazoline derivatives that have already been reported.

In particular, the GST as described above is excellent in terms of the conjugation activity to the isoxazoline derivatives disclosed in JP Patent No. 4,465,133 (i.e., the isoxazoline derivatives (1) to (17) described above) and the isoxazoline derivatives disclosed in JP Patent No. 4,299,483 (i.e., the isoxazoline derivatives (18) to (20) described above). Accordingly, transgenic plants comprising the GST introduced therein have further enhanced resistance to the isoxazoline derivatives disclosed in JP Patent No. 4,465,133 and to the isoxazoline derivatives disclosed in JP Patent No. 4,299,483.

In addition, the GST as described above is excellent in terms of the conjugation activity to pyroxasulfone and fenoxasulfone. Accordingly, transgenic plants comprising the GST introduced therein have further enhanced resistance to pyroxasulfone and fenoxasulfone.

When the isoxazoline derivatives described above are used for herbicides, the growth of various weeds except for the transgenic plants comprising the GST introduced therein can be controlled. Examples of such weeds include, but are not particularly limited to, Gramineae weeds (e.g., *Echinochloa crus-galli* (L.) Beauv. var. *crus-galli*, *Digitaria ciliaris* (Retz.) Koeler, *Setaria viridis* (L.) Beauv., *Poa annua* L., *Sorghum halepense* (L.) Pers., *Alopecurus aequalis* Sobol. var. *amurensis* (Komar.) *Ohwi*, and wild oats), broadleaf weeds (e.g., *Polygonum lapathifolium* L. *nodosum* (Pers.) Kitam., *Amaranthus viridis* L., *Chenopodium album* L., *Stellaria media* (L.) Villars, *Abutilon avicennae*, *Sida spinosa*, *cassia obtusifolia*, *Ambrosia artemisiifolia* L. var. *elatior* (L.) Desc., and morning glory), and perennial or annual cyperaceous weeds (e.g., *Cyperus rotundus* L., *Cyperus esculentus*, *Kyllinga brevifolia* Rottb. subsp. *leiolepis* (Fraxch. et Savat.) T. *koyama*, *Cyperus microiria* Steud., and *Cyperus iria* L.). When the isoxazoline derivatives are used as herbicides in paddy fields, in addition, annual weeds (e.g., *Echinochloa oryzicola* Vasing., *Cyperus difformis* L., *Monochoria vaginalis* (Burm. f.) Presl. var. *plantaginea* (Roxb.) Solms-Laub., and *Lindernia pyxidara* L.) and perennial weeds (e.g., *Cyperus serotinus* Rottb., *Eleocharis kuroguwai Ohwi*, and *Scirpus juncoides* Roxb. subsp. *hotarui* (*Ohwi*) T.

Koyama) can be controlled at a low dose over a long period of time from the pre-emergence stage to the growth stage.

EXAMPLES

Hereafter, the present invention is described in greater detail with reference to the examples, although the technical scope of the present invention is not limited to the examples provided below.

Example 1

In Example 1, the GST identified under Accession Code: Q8GTC0 (referred to as "TaQ8GTC0" herein) among GSTs in wheat plants was analyzed in terms of the activity of glutathione conjugation to VLCFAE-inhibiting herbicides.
<Construction of a Construct of the TaQ8GTC0 Protein Expressed in *E. coli*>
FIG. 1 shows a constitution of a construct of the TaQ8GTC0 protein expressed in *E. coli*. At the outset, cDNA was synthesized via reverse transcription from RNA prepared from the shoots of wheat (Nohrin No. 61) as a template. The cDNA obtained was used as a template to perform PCR with the use of a set of primers (TaQ8GTC0-H (SEQ ID NO: 3) and TaQ8GTC0-D (SEQ ID NO: 4)). Thus, a fragment of the TaQ8GTC0 gene comprising the NdeI recognition site at the 5' terminus and the BamHI recognition site at the 3' terminus was obtained.

Subsequently, the TaQ8GTC0 gene fragment was digested with NdeI and BamHI, the digested TaQ8GTC0 gene fragment was designated as an insert, and pET22b (+) that was also treated with NdeI and BamHI was designated as a vector. Ligation reaction was carried out with the use of the insert and the vector. With the use of a reaction solution after the ligation reaction, a vector contained in the reaction solution was introduced into the *E. coli* JM109 strain. Thereafter, plasmids were prepared from colonies in which introduction of the target plasmids had been confirmed via colony PCR. Through sequence analysis, PCR-induced errors in the nucleotide sequence of the TaQ8GTC0 gene existing between the NdeI cleavage site and the BamHI cleavage site was not detected. The plasmid was introduced into the *E. coli* BL21 (DE3) strain, so as to generate transformed *E. coli* to express TaQ8GTC0 protein (KLB-606).
<Preparation of the TaQ8GTC0 Protein>
The TaQ8GTC0 protein was expressed using the *E. coli* BL21 (DE3) strain (KLB-606). The single colony was inoculated into an LB liquid medium containing 50 ppm ampicillin, cultured overnight with shaking in a test tube, and the resulting solution was used as a preculture solution. The preculture solution (2.5 ml) was added to 250 ml of an LB liquid medium containing 50 ppm ampicillin (a 1-liter erlenmeyer flask) and culture was conducted at 37° C. and 200 rpm until the $OD_{600}$ value reached 0.5 to 0.6. Subsequently, the resultant was cooled on ice for 5 minutes, IPTG was added thereto to a final concentration of 1 mM, and the TaQ8GTC0 protein was induced to express at 27° C. and 200 rpm for 21 hours. Thereafter, the strains were collected via centrifugation at 4° C. and 6000×g for 10 minutes and then stored at −80° C. To the cryopreserved cells (for 0.5-liter culture), 30 ml of PBS buffer (0.14 M NaCl, 2.7 mM KCl, 10 mM $Na_2HPO_4$, 1.8 mM $KH_2PO_4$, pH 7.3) was added, the resultant was ultrasonically treated (TAITEC VP-305, Microchip, Output: 3, constant for 15 seconds, 7 or 8 times), and centrifugation was carried out at 4° C. and 15,000×g for 20 minutes to obtain a supernatant. The crude enzyme solution was loaded in a GSTrap 4B (bed volume: 1 ml) equilibrated with PBS buffer at a flow rate of 1 ml/min, the glutathione affinity column was washed with 20 ml or more PBS buffer, and 2 ml of an elution buffer (50 mM Tris-HCl, 10 mM reduced glutathione, pH 8.0) was injected into the column, so as to elute the TaQ8GTC0 protein (FIG. 2). The protein solution was substituted with PBS buffer via ultrafiltration using Nanosep (10 K) and the resultant was stored at −80° C. Protein concentration was measured by the Bradford method in accordance with the instructions of TaKaRa Bradford Protein Assay Kit (Takara). In FIG. 2, "M" indicates a molecular marker. The results shown in FIG. 2 were attained by applying 8.0 µg of the total protein to the crude enzyme lane and the pass-through fraction lane, respectively. The crude enzyme is the supernatant obtained by ultrasonically treating the cells, followed by centrifugation, and the pass-through fraction is a solution sampled during loading the crude enzyme solution into the affinity column.
<Analysis of the Activity of Glutathione Conjugation to VLCFAE-Inhibiting Herbicide>
All the VLCFAE-inhibiting herbicides used in this example were added to the reaction mixture as acetone solutions. Conjugation reactions to the VLCFAE-inhibiting herbicides were performed in a reaction mixture (total amount: 200 µl) containing 50 µl of 100 mM potassium phosphate buffer (pH 6.8), 10 µl of 1 mM VLCFAE-inhibiting herbicide, 20 µl of 10 mM reduced glutathione (pH 7.0), 6 µl of the TaQ8GTC0 protein (378 ng in total, PBS buffer solution) and 114 µl of PBS buffer, the reaction was conducted at 30° C. for 15 minutes, the reaction product was filtered through a 0.2-m filter, and 50 µl of the filtered solution was injected into HPLC. HPLC analysis conditions were as described below.
Apparatus: Agilent 1100 series
Column: CAPCELL PAK C18 AQ 4.6 mm (i.d.)×250 mm (SHISEIDO)
Mobile phase: acetonitrile/distilled water=5/95 (hold for 5 min)→(4 min)→40/60 (hold for 4 min)→(4 min)→90/10 (hold for 8 min)→(1 min)→5/95 (hold for 4 min) (each solvent containing 0.5% acetic acid)
Temperature: 35° C.
Flow rate: 1.0 ml/min
Detection: 254 nm
<Results and Discussion>
FIG. 3 shows VLCFAE-inhibiting herbicides used in the test for glutathione conjugation activity of the TaQ8GTC0 protein. When the activity of glutathione conjugation to VLCFAE-inhibiting herbicides was analyzed, the amount of glutathione conjugates (GS conjugates) produced was determined based on the amount of VLCFAE-inhibiting herbicides decreased in the reaction solution. Table 1 shows glutathione conjugation activity of the TaQ8GTC0 protein to various VLCFAE-inhibiting herbicides.

TABLE 1

| Herbicide | Type | Enzyme activity (µmol/mg protein/15 min)[a] |
|---|---|---|
| Pyroxasulfone | Isoxazoline | 11.7 ± 3.7 |
| Fenoxasulfone | | 19.5 ± 8.4 |
| Metolachlor | Chloroacetanilide | 2.2 ± 0.8 |
| Alachlor | | 1.5 ± 0.1 |
| Flufenacet | Oxyacetamide | n.d.[b] |
| Mefenacet | | n.d. |
| Anilofos | Dithiophosphoric acid | n.d. |
| Piperophos | | n.d. |

TABLE 1-continued

| Herbicide | Type | Enzyme activity (μmol/mg protein/15 min)[a] |
|---|---|---|
| Fentrazamide | Tetrazolinone | 0.93 ± 0.2 |
| Cafenstrole | Triazole | 0.46 ± 0.1 |
| Indanofan | Oxirane | n.d.[b] |

[a]Enzyme activity to pyroxasulfone is expressed as the mean ± the standard deviation of seven independent experiments and those to other herbicides are expressed as the mean ± the standard deviation of four independent experiments.
[b]Not detected.

FIG. 4 shows an example of the conjugation reaction between pyroxasulfone and glutathione and HPLC chromatograms attained with the use of pyroxasulfone as a VLCFAE-inhibiting herbicide. In the HPLC chromatograms shown in FIG. 4, the upper portion shows the results for glutathione conjugation reaction mixture containing the TaQ8GTC0 protein, the middle portion shows the results for glutathione conjugation reaction mixture without the TaQ8GTC0 protein, and the lower portion shows the results for glutathione conjugation reaction mixture without the TaQ8GTC0 protein and glutathione.

As shown in Table 1, the TaQ8GTC0 protein was found to have a specifically high conjugation activity to pyroxasulfone and fenoxasulfone possessing the isoxazoline moiety among VLCFAE-inhibiting herbicides. In contrast, the glutathione conjugation activity of the TaQ8GTC0 protein to other VLCFAE-inhibiting herbicides moiety was found to be significantly low. As shown in FIG. 4, also, the peak of the GS conjugate of pyroxasulfone (M-15) was observed in the reaction mixture containing pyroxasulfone as a substrate. This indicates that 4.81 nmol of GS conjugate of pyroxasulfone was produced out of a total amount of pyroxasulfone (i.e., 10 nmol) added to the reaction mixture.

In Example 1, the conjugation activity to cafenstrole was determined via quantification of the compound released by the glutathione conjugation of this herbicide. In addition, peaks of GS conjugate of other herbicides (i.e., metolachlor, alachlor, flufenacet, mefenacet, phentolazamide, indanofan, anilofos, and piperophos) were unknown. When analyzing the glutathione conjugation activities to these herbicides, accordingly, glutathione conjugation reactions were performed to produce GS conjugate in the modified conditions (i.e., more amount of enzyme was added or the conjugation reaction was conducted for longer time) in the beginning to produce glutathione conjugates (GS conjugates), and the peaks were identified with LC/MS.

Example 2

In Example 2, transgenic rice plants comprising the TaQ8GTC0 gene introduced therein were prepared, and sensitivity of the transgenic rice plants to VLCFAE-inhibiting herbicides was tested.
<Production of Transgenic Rice Plants>

In Example 2, a vector comprising the TaQ8GTC0 gene for rice transformation (R-5-TaQ8GTC0) was prepared, as shown in FIG. 5.

Specifically, cDNA was first synthesized via reverse transcription from RNA prepared from the shoots of wheat (Nohrin No. 61) as a template. The cDNA obtained was used as a template to perform PCR with the use of a set of primers (TaQ8GTC0-M (SEQ ID NO: 5) and TaQ8GTC0-N (SEQ ID NO: 6)). Thus, a fragment of the TaQ8GTC0 gene comprising the SalI recognition site at the 5' terminus and the NotI recognition site at the 3' terminus was obtained.

Subsequently, the TaQ8GTC0 gene fragment was digested with SalI and NotI, the treated TaQ8GTC0 gene was designated as an insert, and pENTR-1A (Thermo Fisher Scientific Inc.) that was also digested with SalI and NotI was designated as a vector. Ligation reaction was carried out with the use of the insert and the vector. The thus produced entry clone (pENTR1A-TaQ8GTC0) was introduced into the E. coli JM109 strain via transformation. Thereafter, plasmids were prepared from colonies in which introduction of the target plasmids had been confirmed via colony PCR. Through sequence analysis, PCR-induced errors in the nucleotide sequence of the TaQ8GTC0 gene existing between the SalI cleavage site and the NotI cleavage site was not detected.

Subsequently, the produced entry clone (pENTR1A-TaQ8GTC0) (KLB-649) was used in the LR reaction with the destination vector (PalSelect R-5, Inplanta Innovations Inc.), and the resulting expression vector (a rice transformation vector comprising the TaQ8GTC0 gene inserted into the attB sequence of PalSelect R-5) was introduced into the E. coli HST02 strain via transformation. Thereafter, plasmids were prepared from colonies in which introduction of the target plasmids had been confirmed via colony PCR. The nucleotide sequence of the TaQ8GTC0 gene inserted in the attB sequence was confirmed to be correct via sequence analysis (KLB-650).
<Introduction of the TaQ8GTC0 Gene into Rice Plant Via Transformation>

The produced rice transformation vector (PalSelect R-5-TaQ8GTC0) was introduced into Agrobacterium (EHA105) via electroporation (KLB-654). Subsequently, the TaQ8GTC0 gene was introduced into cultured rice cells via the Agrobacterium method (S. Toki Plant Mol. Biol. Rep., 15 16-21, 1997), and selection was then carried out with the use of bispyribac sodium (BS).

The cultured rice cells comprising the TaQ8GTC0 gene introduced therein were selected with the use of 0.25 μM bispyribac sodium (BS) for 1 month after the TaQ8GTC0 gene was introduced into rice plants via transformation. As a result, cultured transgenic rice cells were also observed in the selection medium as with the case of KLB-279 (a positive control comprising the GFP gene introduced instead of the TaQ8GTC0 gene) (FIG. 6). The cultured transgenic rice cells were transferred to a regenaration medium without BS and the resulting plants were cultivated successively in isolated green houses. Ear emergence was observed in all plants 2 months, on average, after the initiation of culture in isolated green houses and progeny seeds (T1) were collected from the plants.
<Pyroxasulfone Resistance of Rice Plants Comprising the TaQ8GTC0 Gene Introduced Therein>

Pyroxasulfone resistance of 18 rice plants was examined via the plant growth in a gellan gum medium containing pyroxasulfone.

Hoagland's mix and 3 g of gellan gum were suspended in 1 liter of distilled water and thoroughly dissolved therein by heating in a microwave. A fraction of the resultant (15 ml) was injected into a tubular bottle before it was cooled (30 ml was injected into the plate). The herbicide was simultaneously added at the time of injection of the gellan gum medium into the tubular bottle or plate, followed by thorough mixing. Rice hulls were soaked in a 50-fold diluted sodium hypochlorite solution (antiformin) (Wako) for approximately 20 minutes and then thoroughly washed with water. Sterilized seeds were soaked in distilled water and allowed to stand at 27° C. for germination (for approximately 2 days). Germinating seeds were softly planted in the gellan gum medium (plate) containing 0.25 μM BS. These samples, together with a beaker filled with distilled water, were placed in a transparent case, which was then covered with a clear plastic wrap. These samples were grown at 27° C. under fluorescent light illumination (14 hours of a light period and 10 hours of a dark period) for 2 days. Thereafter, rice seeds that were determined to have BS resistance with the use of root elongation as the indicator were transferred to gellan gum media containing pyroxasulfone (tubal bottles) at the final concentrations of $10^{-8}$, $10^{-7}$, $10^{-6}$, and $10^{-5}$M, respectively. Subsequently, these samples, together with a beaker filled with distilled water, were placed in a transparent case, which was then covered with a clear plastic wrap. These samples were grown at 27° C. under fluorescent light illumination (14 hours of a light period and 10 hours of a dark period) for 4 to 5 days, and the plant heights were then measured. Inhibition of shoot growth was determined by comparison to control plants grown in the absence of pyroxasulfone and the concentration for required 50% inhibition ($IC_{50}$) was determined by the Probit method.

Table 2 shows the results of the pyroxasulfone resistance of the rice plants comprising the TaQ8GTC0 gene introduced therein.

TABLE 2

| Lineage | $I_{50}$ (nM) | Pyroxasulfone resistance[1] |
|---|---|---|
| Wild | 39 | — |
| #1-3 | 1139 | 29 |
| #1-4 | 1306 | 33 |
| #1-7 | 969 | 25 |
| #1-10 | 510 | 13 |
| #2-6 | 968 | 25 |
| #2-9 | 1091 | 28 |
| #3-4 | 1720 | 44 |
| #3-9 | 1007 | 26 |
| #3-12 | 67 | 2 |
| #3-13 | 13751 | 353 |
| #4-1 | 496 | 13 |
| #4-3 | 4315 | 111 |
| #4-7 | 7146 | 183 |
| #4-10 | 2118 | 54 |
| #4-13 | 3852 | 99 |
| #4-14 | 45 | 1 |
| #5-1 | 968 | 25 |
| #5-11 | 983 | 25 |

In Table 2, 1) represents the ratio of the $IC_{50}$ of rice transformed with TaQ8GTC0 gene to the $IC_{50}$ of wild-type rice. As shown in Table 2, 16 lines among 18 lines used in the test were found to have 10 times or higher pyroxasulfone resistance and the lineage #3-13 was found to have the highest degree of resistance; that is, approximately 350 times higher than that of wild-type plants.

<Determination of Minimal Concentration of VLCFAE-Inhibiting Herbicide that Inhibits the Growth of Wild-Type Rice>

Whether or not a rice plant comprising the TaQ8GTC0 gene introduced therein has VLCFAE-inhibiting herbicide resistance was determined on the basis of a difference in sensitivity of rice between transformant and wild-type. Accordingly, the sensitivity of the wild-type rice plant (Nipponbare) to VLCFAE-inhibiting herbicides used in the glutathione conjugation activity test was examined as described below.

The growth inhibition test was carried out using a gellan gum medium. Hoagland's mix and 3 g of gellan gum were suspended in 1 liter of distilled water and thoroughly dissolved therein by heating in a microwave. A fraction of the resultant (15 ml) was poured in a tubular bottle before it was cooled. When the herbicide (an acetone solution) was to be incorporated thereinto, the herbicide was simultaneously added at the time of filling of the gellan gum medium into the tubular bottle, followed by thorough mixing (final acetone concentration: 0.1%). Rice hulls were soaked in a 50-fold diluted sodium hypochlorite solution (antiformin) (Wako) for approximately 20 minutes and then thoroughly rinsed with water. Sterilized seeds were soaked in distilled water and allowed to stand at 27° C. for germination (for approximately 2 days). Germinating seeds were transferred with the sprout side up to a gellan gum medium containing herbicide (the tubular bottle). Subsequently, these samples, together with a beaker filled with distilled water, were placed in a transparent case, which was then covered with a clear plastic wrap. These samples were grown at 27° C. under fluorescent light illumination (14 hours of a light period and 10 hours of a dark period) for 1 week, the plants were sampled, and the plant heights were then measured. Inhibition of shoot growth was determined by comparison to control plant grown in the absence of herbicide and the concentration required for 50% inhibition ($IC_{50}$) was determined by the Probit method.

The sensitivity of the wild-type rice plant (Nipponbare) to VLCFAE-inhibiting herbicides used in the glutathione conjugation activity test was examined. The $I_{50}$ values of the shoot growth of the wild-type rice by VLCFAE-inhibiting herbicides and the minimal concentration for growth inhibition are shown in Table 3.

TABLE 3

| Drug | $I_{50}$ (nM) | Minimal inhibitory concentration (μM) |
|---|---|---|
| Pyroxasulfone | 48 | 0.075 |
| Fenoxasulfone | 54 | 0.05 |
| Flufenacet | 42 | 0.075 |
| Mefenacet | 388 | 0.75 |
| Alachlor | 332 | 0.5 |
| Metolachlor | 636 | 0.75 |
| Anilofos | 377 | 0.5 |
| Piperophos | 1311 | 2.5 |
| Fentrazamide | 46 | 0.5 |
| Indanofan | 61 | 0.25 |
| Cafenstrole | 131 | 0.75 |

<Resistance of Rice Plants Comprising the TaQ8GTC0 Gene Introduced Therein to VLCFAE-Inhibiting Herbicides>

Resistance of rice plants comprising the TaQ8GTC0 gene introduced therein to VLCFAE-inhibiting herbicides was tested in the same manner as with the pyroxasulfone resistance test described above. In this example, as shown in Table 4, resistance to VLCFAE-inhibiting herbicides was tested at 3 different concentration; i.e., the minimal concentration at which the growth of the wild-type rice plants (Nipponbare) would be completely inhibited (×1); the 4-fold concentration of the minimal concentration (×4); and the 16-fold concentration of the minimal concentration (×16).

TABLE 4

| | Test concentration (μM) | | |
|---|---|---|---|
| Drug | ×1[a] | ×4[b] | ×16[c] |
| Pyroxasulfone | 0.075 | 0.30 | 1.2 |
| Fenoxasulfone | 0.05 | 0.20 | 0.8 |
| Flufenacet | 0.075 | 0.30 | 1.2 |
| Mefenacet | 0.75 | 3.0 | 12 |
| Alachlor | 0.5 | 2.0 | 8.0 |

TABLE 4-continued

| Drug | Test concentration (μM) | | |
|---|---|---|---|
| | ×1[a] | ×4[b] | ×16[c] |
| Metolachlor | 0.75 | 3.0 | 12 |
| Anilofos | 0.5 | 2.0 | 8.0 |
| Piperophos | 2.5 | 10 | 40 |
| Fentrazamide | 0.5 | 2.0 | 8.0 |
| Indanofan | 0.25 | 1.0 | 4.0 |
| Cafenstrole | 0.75 | 3.0 | 12 |

In Table 4, a) represents the minimal concentration at which the growth of the wild-type rice plants (Nipponbare) is inhibited; b) represents the concentration 4 times higher than a); and c) represents the concentration 16 times higher than a).

In this example, Nipponbare was used as a control sample and rice plants comprising the TaQ8GTC0 gene introduced therein (the lineage #3-13) exhibiting strong pyroxasulfone resistance were used. FIGS. 7-1 to 7-6 show the results. In FIGS. 7-1 to 7-6, the concentration of 0 μM, the minimal concentration shown in Table 4 (×1), the concentration 4 times higher than the minimal concentration shown in Table 4 (×4), and the concentration 16 times higher than the minimal concentration shown in Table 4 (×16) are shown successively from left to right.

When the rice plants comprising the TaQ8GTC0 gene introduced therein were treated with pyroxasulfone and fenoxasulfone (FIG. 7-1), the growth thereof was not affected at the maximal test concentration (i.e., 16-fold concentration of the minimal concentration), and such plants exhibited strong resistance. When the rice plants comprising the TaQ8GTC0 gene introduced therein were subjected to treatment with 6 types of herbicides (i.e., flufenacet, anilofos, piperophos, cafenstrole, indanofan, and fentrazamide) (FIGS. 7-2 to 7-4), in contrast, the growth thereof was inhibited at the minimal concentration, and the plants did not exhibit resistance to these herbicides. When the plants were treated with 3 types of herbicides (i.e., metolachlor, alachlor, and mefenacet), the growth thereof was not affected at the minimal concentration, but the growth thereof was inhibited at the 4-fold concentration of the minimal concentration (×4). That is, the resistance of the rice plants comprising the TaQ8GTC0 gene introduced therein to these 3 types of herbicides was found to be very low, that is, insufficient for practical use (FIGS. 7-5 and 7-6).

While no data are disclosed, the lineage #4-7 showed the high level of resistance to pyroxasulfone similar to the lineage #3-13 but showed same sensitivity to other herbicides as that of the lineage #3-13.

As described above, rice plants comprising the TaQ8GTC0 gene introduced therein were found to exhibit resistance specifically to isoxazoline herbicides among various types of VLCFAE-inhibiting herbicides. In addition, herbicide resistance of the transgenic rice plants was substantially correlated with the glutathione conjugation activity of the TaQ8GTC0 protein.

Example 3

In Example 3, transgenic *Arabidopsis thaliana* plants comprising the TaQ8GTC0 gene introduced therein were produced and sensitivity of the transgenic *Arabidopsis thaliana* plants to VLCFAE-inhibiting herbicides was tested.

<Production of Transgenic *Arabidopsis thaliana* Plants>

At the outset, as shown in FIG. 8, a vector for *Arabidopsis thaliana* transformation comprising the TaQ8GTC0 gene (A-3-TaQ8GTC0) was produced. Specifically, the entry clone comprising the TaQ8GTC0 gene (ORF) inserted into a site between attL1 and attL2 of pENTR-1A (Thermo Fisher Scientific Inc.) (pENTR1A-TaQ8GTC0, KLB-649) was used in the LR reaction with the destination vector (PalSelect A-3, Inplanta Innovations Inc.) to produce a vector for *Arabidopsis thaliana* transformation. This vector for *Arabidopsis thaliana* transformation was produced by inserting the TaQ8GTC0 gene into the attB sequence of PalSelect A-3. Subsequently, the vector for *Arabidopsis thaliana* transformation was introduced into the *E. coli* HST02 strain via transformation. Thereafter, introduction of the target plasmid was confirmed via colony PCR, plasmids were prepared from the colonies, and the nucleotide sequence of the TaQ8GTC0 gene inserted in the attB sequence was confirmed to be correct via sequence analysis (KLB-707).

<Introduction of the TaQ8GTC0 Gene into *Arabidopsis thaliana* Via Transformation>

The vector for *Arabidopsis thaliana* transformation (PalSelect A-3-TaQ8GTC0) prepared as described above was introduced into *Agrobacterium* (EHA105) via electroporation (KLB-718). Subsequently, the TaQ8GTC0 gene was introduced into *Arabidopsis thaliana* in accordance with the Floral dip method (S. J. Clough et al., Plant J. 16, 735-743, 1998), and selection was then carried out with the use of bispyribac sodium (BS).

<Confirmation of Gene Introduction into Transgenic *Arabidopsis thaliana* Plants>

Genomic DNA was prepared from the transgenic *Arabidopsis thaliana* plants with a simple procedure using of an Ampdirect Plus sample solution (20 mM Tris-HCl (pH 8.0), 5 mM EDTA, 400 mM NaCl, 0.3% SDS, and 200 μg/ml Proteinase K) (Shimadzu Corporation). Gene introduction was confirmed via PCR with the use of the genomic DNA as a template and the KAPA 3G DNA Polymerase (KAPA BIOSYSTEMS) under the conditions described below.

PCR was carried out in a reaction mixture (50 μl in total, 0.4 μl of template, 0.3 μl of 50 μM sense primer (Sequence (TaQ8GTC0)-2: SEQ ID NO: 7), 0.3 μl of 50 μM antisense primer (NOSter-13: SEQ ID NO: 8), 25 μl of KAPA Plant PCR Buffer, 0.4 μl of KAPA 3G DNA Polymerase, and 23.6 μl of sterile water). PCR was carried out via a cycle comprising: initial denaturation at 95° C. for 20 seconds; a cycle of denaturation at 95° C. for 20 seconds, annealing at 58° C. for 15 seconds, and elongation at 72° C. for 30 seconds, which was repeated 40 times; and final elongation at 72° C. for 4 minutes.

With the use of *Agrobacterium* (KLB-718) comprising the vector for *Arabidopsis thaliana* transformation (PalSelect A-3-TaQ8GTC0) introduced therein, the TaQ8GTC0 gene was introduced into *Arabidopsis thaliana* via transformation. Thereafter, seeds (approximately 50,000 seeds in total) were sampled from the transformed *Arabidopsis thaliana* plants and sowed in a selection medium containing 0.1 μM of BS, and the transformants were selected on the basis of the presence or absence of the selection marker (W574L/S653I mutated *Arabidopsis thaliana* ALS). As a result, 30 plants were found to have grown (FIG. 9). The photograph shown in FIG. 9 shows the conditions 14 days after sowing and it shows 3 transformants among 30 transformants grown in the selection medium. Thereafter, 10 transformants were selected therefrom, genomic DNAs extracted from the leaves thereof with a simple procedure were used as templates to perform PCR, and, as a result, introduction of the wheat GST gene was confirmed (FIG. 10). In FIG. 10, lanes 1 to 10 show the results of PCR that was conducted by selecting 10 transformants from among a total of 30 transformants grown in the selection medium and using genomic DNAs extracted therefrom with a simple procedure as templates. In PCR, a region A (563 bp) was amplified with the use of a set of primer sequences (TaQ8GTC0)-2 and Noster-13. In the electrophoresis photograph shown in FIG. 10, the leftmost lane shows a 100-bp DNA ladder.

<Pyroxasulfone Resistance of *Arabidopsis thaliana* Plant Comprising the TaQ8GTC0 Gene Introduced Therein>

A medium was prepared as described below, so as to examine the pyroxasulfone resistance of the *Arabidopsis thaliana* plant comprising the TaQ8GTC0 gene introduced therein. At the outset, the Murashige-Skoog (MS) media (1 bag), thiamin hydrochloride (3 mg), nicotinic acid (5 mg), pyridoxin hydrochloride (0.5 mg), and sucrose (10 g) were added into a 1-liter beaker, a pH was adjusted to 5.7, the volume of the content was adjusted to 1 liter, and 8 g (0.8%) of agar was added. The resultant was autoclaved and cooled to room temperature, and pyroxasulfone (an acetone solution) was added thereto. A 30-ml fraction thereof was fractionated into a No. 2 square plate to prepare an MS medium containing pyroxasulfone at a given concentration.

Pyroxasulfone sensitivity of transgenic *Arabidopsis thaliana* plants was tested with the use of the medium prepared above as described below. A necessary amount of *Arabidopsis thaliana* dry seeds was agitated in 70% ethanol for 2 minutes and in hypochlorous acid containing 0.02% Triton-X-100 for 15 minutes, followed by washing with sterile water 10 times. Subsequently, the seeds were suspended in 1 ml of the autoclaved 0.1% agar solution, the suspension was thoroughly mixed to prepare a homogeneous solution, and a total of 30 seeds were each placed on the medium surface. The resultant was sealed with a surgical tape, allowed to stand at 4° C. for 2 days, and then transferred to 22° C. for germination.

FIG. 11 shows the results of the wild-type *Arabidopsis thaliana* plant (Columbia-0) and FIG. 12 shows the results of the *Arabidopsis thaliana* plant comprising the TaQ8GTC0 gene introduced therein. The photographs shown in FIGS. 11 and 12 were taken after the plants were grown at 22° C. for 14 days.

As shown in FIG. 11, the growth of the wild-type *Arabidopsis thaliana* plant was inhibited to some extent at the pyroxasulfone concentration of 100 nM and the growth thereof was substantially completely inhibited at 1 µM or higher. As shown in FIG. 12, in contrast, the *Arabidopsis thaliana* plant comprising the TaQ8GTC0 gene introduced therein grew at the pyroxasulfone concentration of 1 µM in the same manner as with the Control (without pyroxasulfone). In addition, such plant sufficiently grew at the concentration of 10 µM, although some growth inhibition was observed compared with the concentration of 1 µM. This indicates that such plants have strong pyroxasulfone resistance. All 7 lines of the *Arabidopsis thaliana* plants comprising the TaQ8GTC0 gene introduced therein used in the test in this example exhibited pyroxasulfone resistance, which was at least 10 times stronger than that of the wild-type (Columbia-0). FIG. 12 shows the results of transgenic *Arabidopsis thaliana* plants (KLB-718 1-1-5) exhibiting particularly strong resistance. These results demonstrate that the wheat GST (TaQ8GTC0) functions in *Arabidopsis thaliana* as well and it confer pyroxasulfone resistance to various plants.

<Sensitivity of *Arabidopsis thaliana* Plants to VLCFAE-Inhibiting Herbicides>

In this example, also, sensitivity of the wild-type *Arabidopsis thaliana* plant to VLCFAE-inhibiting herbicides was tested in the same manner as with the case of the test for pyroxasulfone resistance of the *Arabidopsis thaliana* plant comprising the TaQ8GTC0 gene introduced therein.

Table 5 shows the concentrations of VLCFAE-inhibiting herbicides at which the growth of the wild-type *Arabidopsis thaliana* plants is strongly inhibited.

TABLE 5

| Drug | Test concentration (µM) |
|---|---|
| Pyroxasulfone | 1 |
| Fenoxasulfone | 1 |
| Flufenacet | 1 |
| Mefenacet | 100 |
| Alachlor | 100 |
| Metolachlor | 100 |
| Anilofos | 10 |
| Piperophos | 100 |
| Fentrazamide | 10 |
| Indanofan | 100 |
| Cafenstrole | 1 |

On the basis of the concentrations above, sensitivity of the *Arabidopsis thaliana* plant comprising the TaQ8GTC0 gene introduced therein to VLCFAE-inhibiting herbicides was examined. The results are show in FIGS. 13 and 14. The photographs shown in FIGS. 13 and 14 were taken after the plants were grown at 22° C. for 14 days. As is apparent from FIGS. 13 and 14, the *Arabidopsis thaliana* plant comprising the TaQ8GTC0 gene introduced therein (KLB-718 1-1-5 exhibiting the strongest resistance was tested) exhibited strong resistance to isoxazoline-type herbicides, pyroxasulfone and fenoxasulfone (FIG. 13). The growth of the *Arabidopsis thaliana* plant comprising the TaQ8GTC0 gene introduced therein was strongly inhibited by other 9 types of herbicides as with the case of wild-type plants (FIGS. 13 and 14).

These results demonstrate that the *Arabidopsis thaliana* plants comprising the TaQ8GTC0 gene introduced therein exhibit specific resistance to isoxazoline-type herbicides. In addition, herbicide resistance of the *Arabidopsis thaliana* plants comprising the TaQ8GTC0 gene introduced therein was substantially correlated with the activity of the TaQ8GTC0 protein for glutathione conjugation to herbicides.

Example 4

In Example 4, high temperature stress resistance of transgenic rice plants comprising the TaQ8GTC0 gene introduced therein was tested.

At the outset, the seeds obtained from rice plants comprising the TaQ8GTC0 gene introduced therein, which were determined to have BS resistance on the basis of root elongation in the gellan gum medium (plate), were transferred to a plastic cup in the same manner as with the pyroxasulfone resistance test for the rice plants comprising the TaQ8GTC0 gene introduced therein (Nipponbare plants grown in the BS-free gellan gum medium were transferred to the plastic cup). After the plants were grown in an isolated greenhouse for 1 week, the plants were treated at high temperature (50° C.) for 2.5 hours, they were grown in an isolated greenhouse for an additional 1 week, and the plant heights and root weights were measured. In Example 4, the lineages #4-7 and #3-13 among the rice plants comprising the TaQ8GTC0 gene introduced therein produced in Example 2 were used.

Since similar results were attained through the 3 tests, one of the results is shown in FIG. 15. The test results demonstrate that the rice plants comprising the TaQ8GTC0 gene introduced therein are less influenced by high temperature treatment than Nipponbare in terms of the plant height and the root weight and that the rice plants comprising the TaQ8GTC0 gene introduced therein have resistance to high temperature stress.

Comparative Example 1

In Comparative Example 1, the pyroxasulfone metabolizing activity of GSTs derived from other plants having high homology to TaQ8GTC0 associated with resistance to isoxazoline derivatives and resistance to high temperature stress found in Examples 1 to 4 was analyzed.

Specifically, FIG. 16 shows TaQ8GTC0 and a total of 14 plant-derived GSTs exhibiting a high degree of homology to TaQ8GTC0: 11 types of wheat- and maize-derived GST molecular species; and 3 types of rice-derived GST molecular species having the metabolizing activity for metolachlor, which is the same VLCFAE-inhibiting herbicide as pyroxasulfone (I. Cummins et al., Plant Mol. Biol., 52, 591-603, 2003, B. McGonigle et al., Plant Physiol., 124, 1105-1120, 2000, H. Y. Cho et al., Pestic. Biochem. Physiol., 83, 29-36, 2005, H. Y. Cho et al., Pestic. Biochem. Physiol., 86, 110-115, 2006, and H. Y. Cho et al., J. Biochem. Mol. Biol., 40, 511-516, 2007). In this example, cultured rice cells comprising such plant GST genes had been introduced were produced, and pyroxasulfone resistance was examined. In FIG. 16, figures in parentheses demonstrate degrees of homology of wheat GST (TaQ8GTC0) in amino acid sequences.

Specifically, pyroxasulfone metabolic activity of 7 GSTs were analyzed by the quantification of fatty acid content in cultured rice cells treated with pyroxasulfone and those of 2 GSTs were analyzed on the basis of the growth of cultured rice cells on the solid medium containing pyroxasulfone.
<Analysis of Pyroxasulfone Metabolizing Activity Based on Fatty Acid Content in Cultured Rice Cells>

At the outset, a rice transformation vector was produced as shown in FIG. 17. In this example, cDNAs were prepared via reverse transcription from RNAs prepared from the shoots of rice (Nipponbare), wheat (Nohrin No. 61), and maize (Pioneer 32K61). With the use of cDNAs as templates, the GST genes each comprising the XbaI restriction enzyme site at the 5' terminus and the AflII restriction enzyme site at the 3' terminus were amplified via PCR. Thereafter, the 3' terminuses were digested with AflII and blunted with a T4DNA polymerase, and the 5' terminuses were digested with XbaI. Subsequently, KLB-224 comprising the construct of CSP (rice callus-specific promoter: Gene Locus Os10g0207500)::GUS::NOSt introduced into the MCS of PalSelect R-4 (Inplanta Innovations Inc.) was digested with SacI and blunted with T4 DNA polymerase, to obtain a vector fragment.

The GST gene fragments were ligated to the vector fragments and the resulting vectors were introduced into *E. coli* HST-02 strain via transformation. A part of the transformation reaction solution was applied to a 50 ppm spectinomycin-containing LB solid medium, culture was carried out at 37° C. overnight, and PCR was carried out with the use of grown colonies as templates to select colonies into which target vectors had been introduced. The colonies of interest were inoculated into a 50 ppm spectinomycin-containing YM liquid medium, culture was carried out at 37° C. overnight, and plasmids were prepared from the cells.

Subsequently, nucleotide sequences of the full-length sequence of the target gene introduced into the vector were analyzed via sequencing. The nucleotide sequences of the primers used for producing rice transformation vectors comprising the GST genes inserted therein are shown below.

The following set of primers was used for rice-derived OsGSTF5.

```
OsGSTF5-1:
5'-AAAAAATCTAGAAAAGTGCAGGGCAAATTC-3'
(sense: SEQ ID NO: 9)

OsGSTF5-2:
5'-AAAAAACTTAAGCTATGGTATGTTCCCACT-3'
(antisense: SEQ ID NO: 10)
```

The following set of primers was used for rice-derived OsGSTU5.

```
OsGSTU5-1:
5'-AAAAAATCTAGAATCTTCTTCTCCGACGAG-3'
(sense: SEQ ID NO: 11)

OsGSTU5-2:
5'-AAAAAACTTAAGCTACTTGGCGCCAAACTT-3'
(antisense: SEQ ID NO: 12)
```

The following set of primers was used for wheat-derived TaQ8GTB9.

```
TaQ8GTB9 (GSTF4)-1:
5'-AAAAAATCTAGAATGGAGCCTATGAAGGTG-3'
(sense: SEQ ID NO: 13)

TaQ8GTB9 (GSTF4)-2:
5'-AAAAAACTTAAGTCATGGTATTCTCCCGCT-3'
(antisense: SEQ ID NO: 14)
```

The following set of primers was used for maize-derived ZmB6T8R4.

```
ZmB6T8R4 (Corn)-3:
5'-AAAAAATCTAGATCGTTTCGAGGCCGAT-3'
(sense: SEQ ID NO: 15)

ZmB6T8R4 (Corn)-2:
5'-AAAAAACTTAAGTCACTTGGCCCCGAACTT-3'
(antisense: SEQ ID NO: 16)
```

The following set of primers was used for maize-derived ZmQ9ZP61.

```
ZmQ9ZP61 (GST6)-3:
5'-AAAAAATCTAGATACCAGCCACGTCGCTT-3'
(sense: SEQ ID NO: 17)

ZmQ9ZP61 (GST6)-2:
5'-AAAAAACTTAAGTCACTTGGCCCCGAACTT-3'
(antisense: SEQ ID NO: 18)
```

The following set of primers was used for maize-derived ZmM16901.

```
M16901 (GSTI)-3:
5'-AAAAAATCTAGAGTTGGGTCTGGGACAC-3'
(sense: SEQ ID NO: 19)

M16901 (GSTI)-2:
5'-AAAAAACTTAAGTCAAGCAGATGGCTTCAT-3'
(antisense: SEQ ID NO: 20)
```

The following set of primers was used for maize-derived ZmY12862.

```
ZmY12862 (GST5)-1:
5'-AAAAAATCTAGAATGGCCGAGGAGAAGAAG-3'
(sense: SEQ ID NO: 21)

ZmY12862 (GST5)-2:
5'-AAAAAACTTAAGCTACTCGATGCCCAGCCT-3'
(antisense: SEQ ID NO: 22)
```

Specifically, rice transformation vectors (PalSelect R-4-GST) were prepared for 7 genes among a total of 14 genes shown in FIG. 16. Concerning several genes, the sequences inserted into the vectors were different from the sequences on the GenBank database. Such differences are shown in Table 6.

TABLE 6

| GST gene | Difference in nucleotide sequence | Difference in amino acid sequence |
|---|---|---|
| TaQ8GTB9 | C → G, position 84 | Asp(D)→Glu(E) |
|  | T→G, position 178 | Tyr(Y)→Asp(D) |
|  | C→G, position 315 | His(H)→Gln(Q) |
| ZmM16901 | C→A, position 207 | — |
|  | G→T, position 363 | — |
|  | T→C, position 528 | — |
| ZmB6T8R4 | A→G, position 532 | Ile(I)→Val(V) |
|  | G→C, position 565 | Ala(A)→Pro(P) |
|  | G→C, position 603 | — |
|  | C→A, position 604 | Leu(L)→Met(M) |
|  | G→A, position 629 | Gly(G)→Glu(E) |
| ZmY12862 | A→C, position 79 | Met(M)→Leu(L) |
|  | G→A, position 124 | Gly(G)→Arg(R) |
|  | C→A, position 251 | Ala(A)→Glu(E) |
|  | C→G, position 333 | — |
|  | C→T, position 453 | — |

In Table 6, the symbol "-" indicates that there are no differences in amino acid sequences. The sequences OsG-STF5, OsGSTU5, and ZmQ9ZP61 introduced into the vector were completely consistent with the sequences on the database.

<Introduction of GST Gene into Rice Via Transformation>

The rice transformation vectors comprising various GST genes thus prepared (PalSelect R-4-GST) were introduced into *Agrobacterium* (EHA105) via electroporation. Subsequently, the GST genes were introduced into cultured rice cells via the *Agrobacterium* method (S. Toki Plant Mol. Biol. Rep., 15 16-21, 1997), and selection was then carried out with the use of bispyribac sodium (BS).

<Liquid Culture of Transgenic Cultured Rice Cells>

The transgenic cultured rice cells thus prepared were used for liquid culture in the presence of pyroxasulfone. Pyroxasulfone was added to the liquid medium as an acetone solution. The final acetone concentration was 0.1%. When liquid culture was carried out, cultured rice cells transformed with KLB-279 (a plasmid comprising Act1p (rice actin 1 promoter)::sGFP::NOSt incorporated into the MCS of PalSelect R-4) were designated as the control samples. Liquid culture was carried out as described below.

A bag of mixed salts for Murashige-Skoog medium (MS inorganic salts), 1 ml of 10 mg/ml thiamin hydrochloride, 1 ml of 5 mg/ml nicotinic acid, 1 ml of 10 mg/ml pyridoxine hydrochloride, 1 ml of 2 mg/ml glycine, 1 ml of 0.2 mg/ml 2,4-D, 30 g of sucrose, and 1 ml of 50 mg/ml myo-inositol were added into a 1-liter beaker, a pH was adjusted to 5.7, and the volume was precisely adjusted to 1,000 nil with the addition of distilled water, followed by autoclave. After 0.05 ml of pyroxasulfone was added to a 200-ml erlenmeyer flask containing 50 ml of the liquid medium, about 0.5 g of the control cultured rice cells proliferated in a solid medium of the same composition as described above further supplemented with 3 g of gellan gum and 0.25 µM BS or about 0.5 g of the transgenic cultured rice cells prepared as described above were added to the liquid medium, and culture was carried out for 14 to 17 days. After the completion of culture, the liquid medium was removed, and cultured rice cells were recovered.

One month after the transformation, cultured rice cells comprising the GST genes introduced therein were selected with the use of 0.25 µM bispyribac sodium (BS). Subsequently, the fresh cultured rice cells proliferated in the selection medium were mass-cultured in a conical beaker for approximately 1 month and then used for liquid culture in a pyroxasulfone-containing medium. When conducting liquid culture, the concentration was adjusted to $10^{-7}$M or $10^{-6}$M, so that pyroxasulfone would influence the fatty acid content in the cultured rice cells (Y. Tanetani et al., Pestic. Biochem. Physiol., 95, 47-55, 2009). The influence that may be imposed on the fatty acid content if mutated ALS functioned in cultured rice cells was taken into consideration, and the cultured rice cells transformed with KLB-279 (a plasmid comprising Act1p::sGFP::NOSt incorporated into the MCS of PalSelect R-4) were used as control cells.

<Analysis of Pyroxasulfone Metabolizing Activity Based on Fatty Acid Content in Cultured Rice Cells>

Fatty acid was extracted using undecenoic acid (C11:1) as an internal standard. As analytical standards, Supelco FAME mix containing C14:0, C16:0, C16:1, C18:0, C18:1, C18:2, C18:3, C20:0, C22:0, C22:1, and C24:0 and other fatty acid methyl esters (C11:1, C15:0, C20:1, and C26:0) were used, and calibration curves thereof were prepared, followed by quantification. Fatty acid methyl esters were identified based on the gas chromatography (GC) retention times and mass spectra. Quantitative and qualitative analyses were carried out as methyl esters, although fatty acid methyl esters were converted into fatty acids at the time of quantitative analysis.

Water (10 ml), 25 ml of methanol, and 12.5 ml of chloroform were added to 1 g of cultured cells, and cultured cells were grounded using Hiscotron (Microtec Nition). In this case, 0.1 mg of the internal standard (10-undecenoic acid (C11:1)) dissolved in chloroform was added. The solution used for grinding was suction-filtered, the resultant was introduced into a separatory funnel, 40 ml of chloroform and 50 ml of an aqueous solution of saturated ammonium sulfate were added thereto, the mixture was allowed to stand for approximately 30 minutes to thoroughly extract fatty acid and lipid, and fatty acid extraction with chloroform was repeated two more times (three times in total). The recovered chloroform layer was introduced into a separatory funnel, followed by washing with water. Thereafter, the chloroform layer was recovered in an eggplant flask and concentrated with the use of an evaporator. After dryness under a reduced pressure, 6 ml of 25% potassium hydroxide and 9 ml of ethanol were added to the flask, the mixture was heated at 65° C. for 1 hour, the temperature was cooled to room temperature, and the resultant was acidified with the addition of 10% hydrochloric acid (pH: approximately 2). The solution was introduced into a separatory funnel, 50 ml of hexane was added thereto, the mixture was thoroughly agitated, and an organic layer was recovered. After such procedure was repeated 2 times, the organic layer was recovered via dehydration with solid anhydrous magnesium sulfate. The hexane layer was concentrated with the use of an evaporator, the resultant was dissolved in 2 ml of a mixed solvent (toluene:methanol=4:1 (v/v)), several drops of concentrated sulfuric acid were added dropwise to the reaction mixture, and the reaction was allowed to proceed at 80° C. for 1 hour. After the completion of the reaction, the resultant was cooled to room temperature and neutralized with a saturated sodium bicarbonate solution. The organic layer was recovered after such neutralization was confirmed with the use of a pH test paper. The organic layer (200 µl) was applied to an Eppendorf tube with a filter, and 2 µl of the solution after centrifugation was injected into GC. The conditions for GC analysis are described below.

Apparatus: Agilent 6890 Series GC System
Column: Supelco, Omegawax 250 (30-m long, 0.25-mm (i.d.), film thickness: 0.25 µm)
Injection temperature: 250° C.
Initial temperature: 100° C.
Initial time: 5 min
Rate: 4° C./min
Final temperature: 220° C.
Final time: 25 min
Detector: FID
Detector temperature: 250° C.

FIGS. 18 to 20 show the results of analyses concerning fatty acid contents in 7 types of cultured rice cells comprising plant-derived GST genes introduced therein and in control cultured rice cells, which had been cultured in pyroxasulfone-containing liquid media, and in control cultured rice cells, which had not been treated with pyroxasulfone. The data shown in FIGS. 18 to 20 are one independent experiment. In addition, FIGS. 18 to 20 show the fatty acid contents in 2 lineages of cultured rice cells transformed with GST genes, respectively (lineage 1 and lineage 2).

In the cultured rice cells subjected to culture in a pyroxasulfone-containing liquid medium, the content of very-long-chain fatty acid (VLCFA) drastically decreases due to the VLCFAE inhibition of pyroxasulfone while the C15:0 (pentadecanoic acid) content remarkably increased (Y. Tanetani et al., Pestic. Biochem. Physiol., 95, 47-55, 2009). Whether or not the GSTs had the pyroxasulfone metabolizing activity was determined based on the finding described above. As a result, the C15:0 and VLCFA contents in the cultured rice cells into which 7 types of plant GST genes (i.e., TaQ8GTB9, ZmM16901, ZmB6T8R4, ZmQ9ZP61, ZmY12862, OsGSTF5, or OsGSTU5) had been introduced were found to be similar to those in the control cultured rice cells treated with pyroxasulfone. Accordingly, these GSTs were determined to have no pyroxasulfone metabolizing activity. The results of fatty acid contents in the cultured rice cells into which 2 types of OsGST genes (i.e., F5 and U5) had been introduced were obtained in the 10$^{-6}$ M treatment group, and no data were obtained from the control cultured rice cells untreated with pyroxasulfone. On the basis of the VLCFA and C15:0 contents, both such GSTs were determined to have no metabolizing activity.

<Analysis of Pyroxasulfone Metabolizing Activity Based on the Growth of Cultured Rice Cells in Medium>

Subsequently, rice transformation vectors comprising the maize GST gene were produced as shown in FIG. 21. In this example, 2 types of rice transformation vectors comprising the maize GST genes (ZmQ9FQD1 and ZmB8A3K0), respectively, were produced. Since these vectors were produced in accordance with the same procedure, a process for producing a rice transformation vector comprising the ZmQ9FQD1 gene is described below.

cDNA was synthesized via reverse transcription from RNA prepared from the shoots of maize (Pioneer 32K61). With the use of the synthesized cDNA as a template, PCR was carried out using a set of primers ZmQ9FQD1-X and ZmQ9FQD1-Y to obtain a ZmQ9FQD1 gene fragment. Subsequently, the ZmQ9FQD1 gene fragment was digested with SalI and NotI, the treated ZmQ9FQD1 gene fragment was designated as an insert, and pENTR-1A digested with SalI and NotI was designated as a vector. Ligation reaction was carried out with the use of the insert and the vector. The thus prepared entry clone (pENTR1A-ZmQ9FQD1) was introduced into the E. coli JM109 strain. Thereafter, introduction of the target plasmid into the colony was confirmed via colony PCR, and plasmids were prepared from the colonies. The nucleotide sequence of the ZmQ9FQD1 gene inserted was confirmed to be correct via sequence analysis.

Subsequently, the entry clone (pENTR1A-ZmQ9FQD1) was used for the LR reaction with the destination vector PalSelect R-5 (Inplanta Innovations Inc.) to produce an expression vector (PalSelect R-5-ZmQ9FQD1). The resulting expression vector (PalSelect R-5-ZmQ9FQD1) was introduced into the E. coli HST02 strain via transformation. Thereafter, plasmids were prepared from colonies in which introduction of the target plasmids had been confirmed via colony PCR. Through sequence analysis, the nucleotide sequence of the ZmQ9FQD1 gene inserted was confirmed. Since the sequences of 2 genes inserted into PalSelect R-5 were different from the sequences on the database, such differences are shown in Table 7.

TABLE 7

| GST gene | Difference in nucleotide sequence | Difference in amino acid sequence |
|---|---|---|
| ZmQ9FQD1 | T→C, position 189 | — |
|  | G→C, position 381 | Glu(E) →Asp(D) |
|  | T→C, position 476 | Val(V)→Ala(A) |
|  | G→C, position 477 | — |
|  | A→T, position 485 | Asp(D)→Val(V) |
| ZmB8A3K0 | C→T, position 438 | — |
|  | A→G, position 532 | Ile(I)→Val(V) |
|  | G→C, position 567 | — |
|  | T→C, position 573 | — |
|  | G→C, position 603 | — |
|  | C→A, position 604 | Leu(L)→Met(M) |

In Table 7, the symbol "-" indicates that there are no differences in amino acid sequences.

The sets of primers used for PCR are shown below.

```
ZmB8A3K0-X:
5'-AAAAAAGTCGACATGGCGGCGGCGGCGGAG-3'
(sense: SEQ ID NO: 23)

ZmB8A3K0-Y:
5'-AAAAAAGCGGCCGCTCACTTGGCCCCGAACTTG-3'
(antisense: SEQ ID NO: 24)

ZmQ9FQD1-X:
5'-AAAAAAGTCGACATGGCGCCGCCGATGAAG-3'
(sense: SEQ ID NO: 25)

ZmQ9FQD1-Y:
5'-AAAAAAGCGGCCGCCTATGGTATGTTCCCGCTG-3'
(antisense: SEQ ID NO: 26)
```

<Introduction of GST Gene into Rice Via Transformation>

The 2 rice transformation vectors comprising the maize GST genes thus prepared (PalSelect R-5-ZmGST) were introduced into Agrobacterium (EHA105) via electroporation. Subsequently, the TaQ8GTC0 gene was introduced into cultured rice cells via the Agrobacterium method (S. Toki Plant Mol. Biol. Rep., 15 16-21, 1997), and selection was then carried out with the use of bispyribac sodium (BS).

One month after 2 types of maize GST genes were introduced into rice via transformation, cultured rice cells comprising the GST genes introduced therein were selected with the use of 0.25 μM bispyribac sodium (BS). As a result, cultured rice cells transformed with GST genes proliferated in the selection medium as with the case of KLB-279 (i.e., a positive control comprising the GFP gene introduced instead of the TaQ8GTC0 gene), and it was determined that 2 lineages of cultured rice cells comprising the maize GST genes introduced therein were produced (FIG. 22).

<Analysis of Pyroxasulfone Metabolizing Activity Based on the Growth of Cultured Rice Cells in Medium>

The 2 lineages of cultured rice cells comprising the maize GST genes introduced thus prepared and the KLB-279 cultured transgenic rice cells (the control cells) were seeded on N6D medium, and pyroxasulfone resistance was inspected based on the growth of cultured rice cells 2 weeks later. Pyroxasulfone was subjected to the test as an acetone solution, the final acetone concentration to be added to the medium was 1%, and the final drug concentration was $10^{-4}$ M.

The results are shown in FIG. 23. The photographs shown in FIG. 23 show the growth conditions for cultured transgenic rice cells in a medium containing 100 μM ($10^{-4}$M) pyroxasulfone. According to FIG. 23, the 2 lineages of cultured rice cells comprising GST genes introduced therein were merely enlarged as with the case of control cells 2 weeks after seeding. As with the control samples, neither the cultured rice cells comprising the ZmB8A3K0 gene introduced therein nor the cultured rice cells comprising the ZmQ9FQD1 gene introduced therein were proliferated, and neither cells exhibited pyroxasulfone resistance. On the basis of the results attained in this example, accordingly, two types of maize-derived GSTs were determined to have no pyroxasulfone metabolizing activity.

On the basis of the results attained in the comparative example, wheat and maize GSTs exhibiting a high degree of homology to rice GST or TaQ8GTC0 known to be associated with the metabolism of drug having same mode of action as with pyroxasulfone were found to have no pyroxasulfone metabolizing activity. Accordingly, pyroxasulfone metabolizing activity of TaQ8GTC0 as described in Examples 1 to 4 was found to be specific, such that it could not be readily predicted on the basis of known information.

Comparative Example 2

In Comparative Example 2, the glutathione conjugation activity of wheat GST (TaQ8GTC1) having the highest homology to TaQ8GTC0 in amino acid sequence (variety: Hunter; Accession No. AJ440791; homology: 78%) was analyzed.

<Cloning of TaQ8GTC1 Gene (FIG. 24)>

In Comparative Example 2, 6 wheat varieties (i.e., Yumekaori, Hanamanten, Yumeseiki, Nohrin No. 61, Apache, and Gatalina) were prepared. cDNAs synthesized via reverse transcription from RNAs prepared from the shoots of the above 6 wheat varieties were used as templates, and ORFs of the TaQ8GTC1 genes comprising the XbaI recognition site at the 5' terminus and the EcoRI recognition site at the 3' terminus were obtained via PCR. The resulting gene fragments were digested with XbaI and EcoRI, the resulting TaQ8GTC1 gene fragments were designated as inserts, and pBI121 digested with the same restriction enzymes was designated as a vector. Ligation reaction was carried out with the use of the inserts and the vector. The produced vector was introduced into the *E. coli* JM109 strain via transformation. Thereafter, introduction of the target plasmids into the colonies was confirmed via colony PCR, and plasmids were prepared from the colonies. Subsequently, the nucleotide sequences of the target genes inserted into the vector were analyzed via sequencing.

The set of primers used for PCR are shown below.

```
TaQ8GTC1-3:
5'-AAAAAATCTAGAGATCTTCAAGAAGCGGAA-3'
(sense: SEQ ID NO: 27)

TaQ8GTC1-4:
5'-AAAAAAGAATTCTCACTTCTCTGCCTTCTTTCCGA-3'
(antisense: SEQ ID NO: 28)
```

The set of primers used for sequence analysis are shown below.

```
Sequence (TaQ8GTC1)-2:
5'-GACCTCACCATCTTCGAGTC-3'
(sense: SEQ ID NO: 29)

Sequence (TaQ8GTC1)-3:
5'-CTCGTACACGTCGAACAG-3'
(antisense: SEQ ID NO: 30)
```

While the nucleotide sequences of TaQ8GTC1 genes were found to the identical among 6 wheat varieties, such sequence was different from that on the database. Specifically, the nucleotide sequence determined in this experiment was different from that on the database in 25 nucleotides of the ORF of TaQ8GTC1 gene (675 bp). The differences were accompanied with 13 amino acid mutations. Hereafter, the gene of the nucleotide sequence determined in this experiment is referred to as the "TaQ8GTC1-R" gene.

FIG. 25 shows the comparison of nucleotide sequence between TaQ8GTC1-R and TaQ8GTC1, and FIG. 26 shows the comparison of amino acid sequences between TaQ8GTC1-R and TaQ8GTC1. In FIG. 25, 25 nucleotides in the nucleotide sequences that differ between TaQ8GTC1-R (the upper line) and TaQ8GTC1 on the database (the lower line) are surrounded by rectangle. In FIG. 26, the 13 amino acids in the amino acid sequences that were found to differ between TaQ8GTC1-R (the upper line) and TaQ8GTC1 on the database (the lower line) are surrounded by rectangle. In addition, differences between the nucleotide sequence determined in this experiment and the nucleotide sequence registered on the database are summarized in Table 8. In Table 8, the symbol "-" indicates that there are no differences in amino acid sequences even if there are differences in nucleotide sequences.

TABLE 8

| Difference in nucleotide sequence | Difference in amino acid sequence |
| --- | --- |
| T→C, position 25 | Tyr (T)→His (H), position 9 |
| C→T, position 61 | — |
| C→G, position 138 | — |
| C→A, position 151 | — |
| G→A, position 207 | — |
| A→G, position 246 | — |
| T→A, position 287 | Met (M)→Lys (K), position 96 |
| C→G, position 315 | — |
| C→G, position 348 | — |
| C→G, position 382 | Gln (Q)→Glu (E), position 128 |
| C→A, position 394 | Ala (A)→Thr (T), position 132 |
| T→G, position 429 | Asn (N)→Lys (K), position 143 |
| C→G, position 453 | — |
| T→C, position 474 | — |
| G→C, position 483 | Glu (E)→Asp (D), position 161 |

TABLE 8-continued

| Difference in nucleotide sequence | Difference in amino acid sequence |
|---|---|
| G→T, position 484 | |
| G→C, position 486 | Ala (A)→Ser (S), position 162 |
| G→C, position 487 | Val (V)→Leu (L), position 163 |
| G→C, position 498 | — |
| T→C, position 517 | Phe (F)→Leu (L), position 173 |
| A→C, position 525 | — |
| A→T, position 560 | Glu (E)→Val (V), position 187 |
| C→T, position 581 | Ala (A)→Val (V), position 194 |
| T→C, position 595 | Phe (F)→Leu (L), position 199 |
| C→G, position 606 | Ser (S)→Arg (R), position 202 |

The nucleotide sequence determined in this experiment (i.e., the nucleotide sequence of the TaQ8GTC1-R gene) and the amino acid sequence encoded by such nucleotide sequence are shown in SEQ ID NOs: 31 and 32, respectively. The nucleotide sequence of the TaQ8GTC1 gene registered on the database and the amino acid sequence encoded by such nucleotide sequence are shown in SEQ ID NOs: 33 and 34, respectively.

<Construction of a Construct of the TaQ8GTC1-R Protein Expressed in E. coli (FIG. 27)>

With the use of cDNA synthesized via reverse transcription from RNA prepared from the shoots of wheat (Nohrin No. 61) as a template, PCR was carried out with the use of the set of primers TaQ8GTC1-Z and TaQ8GTC1-4 shown below to obtain an ORF of the TaQ8GTC1-R gene comprising the NdeI recognition site at the 5' terminus and the EcoRI recognition site at the 3' terminus. The resulting gene fragment was digested with NdeI and EcoRI, the fragment was designated as an insert, and pET22b(+) digested with the same restriction enzymes was designated as a vector. Ligation reaction was carried out with the use of the insert and the vector, and the produced vector was introduced into the E. coli JM109 strain by transformation.

Thereafter, introduction of the target plasmids into the colonies was confirmed via colony PCR, and plasmids were prepared from the colonies. Through sequence analysis, PCR-induced errors in the nucleotide sequence of the TaQ8GTC1-R gene inserted into a site between the NdeI cleavage site and the EcoRI cleavage site was not detected. The plasmid was introduced into the E. coli BL21 (DE3) strain, so as to generate transformed E. coli to express TaQ8GTC1-R protein (KLB-862). The set of primers used for PCR is shown below.

```
TaQ8GTC1-Z:
5'-AAAAAACATATGGCGGCGCCGGCGGTGAAGGTG-3'
(sense: SEQ ID NO: 35)

TaQ8GTC1-4:
5'-AAAAAAGAATTCTCACTTCTCTGCCTTCTTTCCGA-3'
(antisense: SEQ ID NO: 36)
```

<Preparation of the TaQ8GTC1-R Protein>

Expression of the TaQ8GTC1-R protein was conducted using the E. coli BL21 (DE3) strain (KLB-862). The single colony was inoculated into an LB liquid medium containing 50 ppm ampicillin, cultured overnight with shaking in a test tube, and the resulting solution was used as a preculture solution. The preculture solution (2.5 ml) was added to 250 ml of an LB liquid medium containing 50 ppm ampicillin (a 1-liter erlenmeyer flask) and culture was conducted at 37° C. and 200 rpm until the $OD_{600}$ value reached 0.5 to 0.6. Subsequently, the resultant was cooled on ice for 5 minutes, IPTG (final concentration of 1 mM) was added thereto, and the TaQ8GTC1-R protein was induced to express at 27° C. and 200 rpm for 21 hours. Thereafter, the cells were collected by centrifugation at 4° C. and 6000×g for 10 minutes and then stored at −80° C. To the cryopreserved cells (for 0.5-liter culture), 30 ml of PBS buffer (0.14 M NaCl, 2.7 mM KCl, 10 mM $Na_2HPO_4$, 1.8 mM $KH_2PO_4$, pH 7.3) was added, the resultant was ultrasonically treated (TAITEC VP-305, Microchip, Output: 3, constant for 15 seconds, 7 or 8 times), and centrifugation was carried out at 4° C. and 15,000×g for 20 minutes to obtain a supernatant. The crude enzyme solution was loaded in a GSTrap FF column and a GSTrap 4B column (bed volume: 1 ml) equilibrated with PBS buffer at a flow rate of 1 ml/min, the glutathione affinity columns were washed with 20 ml or more PBS buffer, and 2 ml of an elution buffer (50 mM Tris-HCl, 10 mM reduced glutathione, pH 8.0) was injected into the columns, so as to elute the TaQ8GTC1-R protein (FIG. 28). The protein solution was substituted with PBS buffer by ultrafiltration using Nanosep (10 K) and the resultant was stored at −80° C. Protein concentration was measured by the Bradford method in accordance with the instructions of TaKaRa Bradford Protein Assay Kit (Takara).

<Analysis of the Glutathione Conjugation Activity of the TaQ8GTC1-R Protein>

In this experiment, the glutathione conjugation activity of the purified TaQ8GTC1-R protein was examined when CDNB (2,4-dinitrochlorobenzene) and pyroxasulfone are used as a substrate, respectively.

The glutathione conjugation activity to CDNB was assayed in a reaction mixture (1 ml in total) containing 634 µl of 100 mM potassium phosphate buffer (pH 7.6), 300 µl of 3.3 mM reduced glutathione, 33 µl of a purified enzyme (PBS solution containing 20% glycerol), and 33 µl of 30 mM CDNB (ethanol solution). First, reaction mixture except CDNB was prepared, enzyme reaction was started by the addition of CDNB, and the absorbance at 340 nm was monitored at 30° C. The enzyme activity was calculated using a molar extinction coefficient of glutathione conjugate of CDNB (GS-CDNB) (9.6 $mM^{-1}cm^{-1}$). The amount of GS-CDNB produced in a negative control mixture prepared with the addition of PBS containing 20% glycerol instead of the enzyme (i.e., a non-enzymatic reaction group) was designated as the amount of non-enzymatic production.

The glutathione conjugation activity to pyroxasulfone was measured in a reaction mixture (200 µl in total) containing 50 µl of 100 mM potassium phosphate buffer (pH 6.8), 10 µl of 1 mM pyroxasulfone (acetone solution), 20 µl of 10 mM reduced glutathione (pH 7.0), and 120 µl of the TaQ8GTC1-R protein (PBS solution containing 20% glycerol), the reaction was conducted at 30° C. for 1 hour, the reaction product was filtered through a 0.2-µm filter, and 50 µl of the resulting solution was injected into HPLC. A reaction mixture (prepared with the addition of PBS containing 20% glycerol instead of the TaQ8GTC1-R protein) and another reaction mixture (prepared with the addition of PBS containing 20% glycerol and sterile water instead of the TaQ8GTC1-R protein and glutathione, respectively) were prepared as control reaction mixture. The retention time of pyroxasulfone and that of an M-15 (i.e., glutathione conjugate of pyroxasulfone) were 19.0 minutes and 11.0 minutes, respectively, under the conditions described above.

Apparatus: Agilent 1100 series
Column: CAPCELL PAK C18 AQ 4.6 mm (i.d.)×250 mm (SHISEIDO)
Mobile phase: acetonitrile/water=5/95 (hold for 5 min)→(4 min)→40/60 (hold for 4 min)→(4 min)→90/10 (hold for 8 min)→(1 min)→5/95 (hold for 4 min) (each solvent containing 0.5% acetic acid)
Temperature: 35° C.
Flow rate: 1.0 ml/min
Detection: 254 nm
<Results and Discussion>

At the outset, the glutathione conjugation activity of the TaQ8GTC1-R protein to a standard substrate (i.e., CDNB, 1-chloro-2,4-dinitrobenzene) was examined, so as to determine whether or not the TaQ8GTC1-R protein had the GST activity. The results demonstrate that the activity to CDNB is 2.17 µmol/min/mg protein (n=2) and the purified enzyme has GST activity.

Subsequently, the glutathione conjugation activity of the TaQ8GTC1-R protein to pyroxasulfone was examined. The conjugation activity test was performed in 3 reaction mixture: enzyme reaction mixture (a glutathione conjugate is enzymatically and non-enzymatically generated); reaction mixture without enzyme (a glutathione conjugate is non-enzymatically generated); and reaction mixture without enzyme and glutathione (a parent compound remains). The amount of the protein added to the enzyme reaction mixture was determined to be 500 ng since about 50% of a total of 10 nmol of the added herbicides was converted into glutathione conjugates when the enzyme activity of the about 400 ng of TaQ8GTC0 (see Example 1) was inspected under the same conditions.

As a result of the conjugation activity test of the TaQ8GTC1-R protein, the amounts of glutathione conjugates produced in enzyme reaction mixture and reaction mixture without enzyme were equivalent to each other when pyroxasulfone was a substrate (about 3% of pyroxasulfone added to the reaction mixture was converted into M-15) (FIG. 29). Thus, since there is no significant difference in the amount of glutathione conjugates produced in enzyme reaction mixture and reaction mixture without enzyme, it was indicated that the TaQ8GTC1-R protein did not possess glutathione conjugation activity to pyroxasulfone. As described in Example 1, for example, TaQ8GTC0 having about 80% homology in amino acid sequence to TaQ8GTC1-R was found to exhibit a particularly high glutathione conjugation activity to pyroxasulfone among VLCFAE inhibitors, although the TaQ8GTC1-R protein did not exhibit any enzyme activity.

Since GST having high similarity to TaQ8GTC0 did not have pyroxasulfone-conjugating activity, the conjugation activity of TaQ8GTC0 described in Examples 1 to 3 was considered to be of a highly specific.

Amino acid residues involved in substrate recognition of a plant GST classified into the same Phi class as the TaQ8GTC0 (TaGSTF3) possessing the pyroxasulfone metabolizing activity, which is derived from the wheat-derived GST as described in Examples 1 to 3, were identified by analysis of crystal structure of the complex of GST and substrate (P. Reindeer et al., J. Mol. Biol., 255, 289-309, 1996, T. Neuefeind et al., J. Mol. Biol., 274, 446-453, 1997, H. Pegeot et al., Frontiers in Plant Science 5, 1-15, 2014, and T. Neuefeind et al., J. Mol. Biol., 274, 446-453, 1997). FIG. 30 shows the putative substrate recognition sites in the amino acid sequences of various plant GSTs detected via multiple alignment, and Table 9 summarizes the amino acid residues, which is revealed to form the substrate recognition sites. In FIG. 30, the 2 putative substrate recognition sites are surrounded by rectangle, and the amino acid residues constituting the putative substrate recognition sites are indicated with boldface (with underlines).

The amino acid sequence of AtGSTF2 derived from *Arabidopsis thaliana*, the amino acid sequence of PttGSTF1 derived from poplar, the amino acid sequence of ZmGSTF1 derived from maize, the amino acid sequence of TaGSTF1 derived from wheat, the amino acid sequence of TaGSTF4 derived from wheat, the amino acid sequence of TaGSTF5 derived from wheat, and the amino acid sequence of TaG-STF6 derived from wheat shown in FIG. 30 are shown in SEQ ID NO: 37, SEQ ID NO: 38, SEQ ID NO: 39, SEQ ID NO: 40, SEQ ID NO: 41, SEQ ID NO: 42, and SEQ ID NO: 43, respectively. The amino acid sequence of TaGSTF2-R derived from wheat and the amino acid sequence of TaG-STF3 derived from wheat shown in FIG. 30 are shown in SEQ ID NO: 32 and SEQ ID NO: 2, respectively.

TABLE 9

| Plant GST | Amino acid residues constituting substrate recognition site |
|---|---|
| AtGSTF2 [1] | I12, L35, S115, F119, F123 |
| AtGSTF2 [2] | H8, A10, S11, L35, F119, F123, Y127, Y178 |
| ZmGSTF1 [2] | M10, W12, N13, F35, F114, I118 |
| ZmGSTF1 [3] | M10, W12, F114, I118, M121, L122, |
| PttGSTF1 [4] | L12, T14, L37, H119, F123 |

[1] Structure 6, 1445-1452, 1998
[2] J. Mol. Biol. 255, 289-309, 1996
[3] J. Mol. Biol., 274, 446-453, 1997
[4] Frontiers in Plant Science 5, 1-15, 2014

As shown in FIG. 30 and Table 9, amino acids involved in substrate recognition (corresponding to the amino acid sequence of TaGSTF3 (TaQ8GTC0)) are mainly distributed in the area from positions 5 to 15 (Region 1) and that from positions 115 to 125 (Region 2) of GST. Accordingly, these 2 regions were assumed to be substrate recognition sites of GST and the homology of these regions (Region 1 comprising 10 amino acid residues and Region 2 comprising 12 amino acid residues) to TaGSTF3 (TaQ8GTC0) in amino acid sequence among plant GSTs were investigated.

As a result, the sequence identity of Region 1 was found to be 40%, 80%, 80%, 40%, and 50% between TaGSTF3 (TaQ8GTC0) and TaGSTF1, TaGSTF2-R, TaGSTF4, TaG-STF5, and TaGSTF6, respectively. The sequence identity of Region 2 was found to be 45%, 64%, 55%, 45%, and 18% between TaGSTF3 (TaQ8GTC0) and TaGSTF1, TaGSTF2-R, TaGSTF4, TaGSTF5, and TaGSTF6, respectively. TaG-STF1, TaGSTF2-R, TaGSTF3 (TaQ8GTC0), TaGSTF4, TaGSTF5, and TaGSTF6 are disclosed as wheat-derived GSTs classified in the Phi class (I. Cummins et al., Plant Mol. Biol., 52, 591-603, 2003).

In both Region 1 and Region 2, TaGSTF2-R (TaQ8GTC1-R) was found to have the highest homology to TaQ8GTC0 (TaGSTF3) in amino acid sequence. Since TaGSTF2-R (TaQ8GTC1-R) does not exhibit the pyroxasulfone metabolizing activity, the fact that TaGSTF3 (TaQ8GTC0) possesses the activity to metabolize pyroxasulfone described in Examples 1 to 3 is considered to highly specific.

Comparative Example 3

In Comparative Example 3, transgenic rice plants were produced by introduction of the TaQ8GTC1-R gene cloned in Comparative Example 2, and pyroxasulfone resistance of the transgenic rice plants was analyzed.

<Production of Rice Transformation Vector Comprising the TaQ8GTC1-R Gene (R-5-TaQ8GTC 1-R) (FIG. 31)>

With the use of cDNA synthesized via reverse transcription from RNA prepared from the shoots of wheat (Nohrin No. 61) as a template, PCR was carried out with the use of the set of primers TaQ8GTC1-X and TaQ8GTC1-Y to obtain an ORF of the TaQ8GTC1-R gene. The resulting gene fragment was digested with SalI and NotI, the resulting TaQ8GTC1-R gene fragment was designated as an insert, and pENTR-1A digested with the same restriction enzymes was designated as a vector. Ligation reaction was carried out with the use of the insert and the vector, and the resulting entry clone (pENTR1A-TaQ8GTC1-R) was introduced into the *E. coli* JM109 strain by transformation. Thereafter, introduction of the target plasmids into the colonies was confirmed via colony PCR, and plasmids were prepared from the colonies. The nucleotide sequence of the TaQ8GTC1-R gene inserted into a site between the SalI cleavage site and the NotI cleavage site was confirmed to be correct by sequence analysis.

Subsequently, the entry clone (pENTR1A-TaQ8GTC1-R) was used for the LR reaction with the destination vector PalSelect R-5 (PalSelect pSTARA) to produce an expression vector. The resulting expression vector (a rice transformation vector comprising the TaQ8GTC1-R gene inserted into the attB sequence of R-5) was introduced into the *E. coli* HST02 strain by transformation. Thereafter, plasmids were prepared from colonies in which introduction of the target plasmids had been confirmed by colony PCR. The nucleotide sequence of the TaQ8GTC1-R gene inserted into the attB sequence was confirmed to be correct by sequence analysis. The set of primers used for PCR is shown below.

```
TaQ8GTC1-X:
5'-AAAAAAGTCGACATGGCGGCGCCGGCGGTGAAGG-3'
(sense: SEQ ID NO: 44)

TaQ8GTC1-Y:
5'-AAAAAAGCGGCCGCTCACTTCTCTGCCTTCTT-3'
(antisense: SEQ ID NO: 45)
```

<Introduction of the TaQ8GTC1-R Gene into Rice Plant Via Transformation>

The rice transformation vector comprising the TaQ8GTC1-R gene inserted into PalSelect R-5 (PalSelect R-5-TaQ8GTC1-R) was introduced into *Agrobacterium* (EHA105) via electroporation (KLB-872). Subsequently, the TaQ8GTC1-R gene was introduced into cultured rice cells by the *Agrobacterium* method and selection was then carried out with the use of bispyribac sodium (BS).

The cultured rice cells comprising the TaQ8GTC1-R gene introduced therein were selected with the use of 0.25 µM bispyribac sodium (BS) for 1 month after the TaQ8GTC1-R gene was introduced into rice plants via transformation. As a result, cultured rice cells transformed with TaQ8GTC1-R gene proliferated in the selection medium were observed (FIG. 32). The cultured rice cells were transferred to a regeneration medium without BS and the resulting plants were cultivated in isolated green houses. Ear emergence was observed in all plants for 2 months, on average, after the initiation of culture in isolated green houses and progeny seeds (T1) were collected from the plants.

<Test for Sensitivity of Rice Plants Comprising the TaQ8GTC1-R Gene Introduced Therein to Pyroxasulfone>

Pyroxasulfone resistance of 2 rice plants strains (KLB-872#3-11 and KLB-872#2-4) was examined via the germination growth inhibitory test using a gellan gum medium. At the outset, Hoagland's mix and 3 g of gellan gum were suspended in 1 liter of distilled water and thoroughly dissolved therein by heating in a microwave. A fraction of the resultant (15 ml) was poured into a tubular bottle before it was cooled (30 ml was injected into the plate). Pyroxasulfone (acetone solution) was simultaneously added at the time of filling of gellan gum medium into the tubular bottle or plate, followed by thorough mixing. Rice hulls were soaked in a 50-fold diluted sodium hypochlorite solution (antiformin) (Wako) for approximately 20 minutes and then thoroughly washed with water. Sterilized seeds were soaked in distilled water and allowed to stand at 27° C. for germination (for approximately 2 days). Germinated seeds were softly planted with the sprout side up in the gellan gum medium (plate) containing 0.25 µM BS. These samples, together with a beaker filled with distilled water, were placed in a transparent case, which was then covered with a clear plastic wrap. These samples were grown at 27° C. under fluorescent light illumination (14 hours of a light period and 10 hours of a dark period) for 2 days. Thereafter, rice seeds that were determined to have BS resistance with the use of root elongation as the indicator were transferred to gellan gum media containing pyroxasulfone (tubal bottles) at the final concentrations of $10^{-8}$, $10^{-7}$, $10^{-6}$, and $10^{-5}$M, respectively. Subsequently, these samples, together with a beaker filled with distilled water, were placed in a transparent case, which was then covered with a clear plastic wrap. These samples were grown at 27° C. under fluorescent light illumination (14 hours of a light period and 10 hours of a dark period) for 4 to 5 days, and the plant heights were then measured. Inhibition of shoot growth was determined by comparison to control plants grown in the absence of pyroxasulfone and the concentration required for 50% inhibition ($IC_{50}$) was determined by the Probit method.

<Results and Discussion>

FIG. 33 shows the results of pyroxasulfone resistance test of the rice plants transformed with TaQ8GTC1-R gene on the gellan gum medium containing pyroxasulfone (i.e., KLB-872#3-11 and KLB-872#2-4). Both the 2 strains subjected to the test were found to have sensitivity equivalent to that of wild-type plants. Based on the results obtained, it was indicated that the rice plants transformed with TaQ8GTC1-R gene did not exhibit the resistance to pyroxasulfone.

Example 5

In Example 5, transgenic rapeseed (*Brassica napus*) plants transformed with TaQ8GTC0 gene, which was demonstrated to have the conjugation activity for pyroxasulfone in Examples 1 to 3, were produced and sensitivity of the transgenic rapeseed plants to pyroxasulfone was examined.

<Production of Rape Transformation Vector Comprising the TaQ8GTC0 Gene (FIG. 34)>

With the use of cDNA synthesized via reverse transcription from RNA prepared from the shoots of wheat (Nohrin No. 61) as a template, PCR was carried out with the use of the set of primers TaQ8GTC0—IF-Blunt End (XbaI) and TaQ8GTC0—IF-Blunt End (SacI) to obtain an ORF of the TaQ8GTC0 gene. The resulting gene fragment was digested with XbaI and SacI and then used for the In-Fusion reaction with the use of pBI121 that was blunted with $T_4$ DNA polymerase. The resulting plasmid for rapeseed transformation (TaQ8GTC0 in pBI121) was introduced into the *E. coli* JM109 strain by transformation. Thereafter, introduction of the target plasmids into the colonies was confirmed by colony PCR, and plasmids were prepared from the colonies. The nucleotide sequence of the TaQ8GTC0 gene inserted into a site between the XbaI cleavage site and the SacI cleavage site was confirmed to be correct by sequence analysis. The set of primers used for PCR is shown below.

```
TaQ8GTC0-IF-Blunt End (XbaI):
5'-CACGGGGGACTCTAGATGGCGCCGGCGGTGAAGGT-3'
(sense: SEQ ID NO: 46)

TaQ8GTC0-IF-Blunt End (SacI):
5'-GATCGGGGAAATTCGCTACTCTGCTTTCTTTCCAA-3'
(antisense: SEQ ID NO: 47)
```

<Introduction of the TaQ8GTC0 Gene into Rapeseed Plants by Transformation>

The produced rapeseed transformation vector comprising the TaQ8GTC0 gene (pBI121-TaQ8GTC0) was introduced into *Agrobacterium* (GV3101) by electroporation (KLB-858). Subsequently, the TaQ8GTC0 gene was introduced into rapeseed by the *Agrobacterium* method and selection was then carried out with the use of kanamycin.

<Confirmation of Gene Introduction into Transgenic Rapeseed Plants>

Genomic DNA was prepared from the transgenic rapeseed plants with the use of a DNeasy Plant Mini Kit. Thereafter, PCR was carried out with the use of the prepared genomic DNA as a template, and introduction of a target construct was confirmed. PCR was carried out in a reaction mixture (25 µl in total, 2 µl of the template, 0.25 µl of a 50 04 sense primer, 0.25 µl of a 50 µM antisense primer, 2.5 µl of a 2 mM dNTP mixture, 5 µl of a Phire reaction buffer, 0.5 µl of a Phire Hot Start DNA Polymerase, and 14.5 µl of sterile water). PCR was carried out via a cycle comprising: initial denaturation at 98° C. for 20 seconds; a cycle of denaturation at 98° C. for 20 seconds, annealing at 58° C. for 15 seconds, and elongation at 72° C. for 30 seconds, which was repeated 40 times; and final elongation at 72° C. for 4 minutes. The nucleotide sequences of the primers used when confirming the introduction of the T-DNA region are shown below.

```
NOSP-2:
5'-CGCCTAAGGTCACTATCAGCTAGC-3'
(antisense: SEQ ID NO: 48)

Linker (pBI121)-2:
5'-GAACTCCAGCATGAGATC-3'
(antisense: SEQ ID NO: 49)

CAM35S-1:
5'-AGAGGACCTAACAGAACTCGCC-3'
(sense: SEQ ID NO: 50)

TaQ8GTC0-2:
5'-AAAAAACTTAAGCTACTCTGCTTTCTTTCC-3'
(antisense: SEQ ID NO: 51)
```

A rapeseed transformation vector prepared via introduction of the TaQ8GTC0 gene into pBI121 containing kanamycin as a selection reagent was introduced into the *Agrobacterium* GV3101 strain (KLB-858) by electroporation, and the resulting vector was used to introduce the TaQ8GTC0 gene into a rapeseed plant by transformation. As a result, an individual that is assumed to be a target transformant was obtained (FIG. 35 in which the individual is surrounded by a rectangle). PCR was carried out with the use of the genomic DNA extracted from the transgenic rapeseed plant as a template. As a result, the individual of interest was found to comprise two constructs in the T-DNA region introduced therein (PNOS::NPTII::TNOS, P35S::TaQ8GTC0::TNOS) and it was thus found to be the target transgenic rapeseed plant (FIG. 36). This transgenic rapeseed plant was continuously cultivated in phytotron, and T1 seeds were collected.

<Pyroxasulfone Sensitivity of Rapeseed Comprising the TaQ8GTC0 Gene Introduced Therein>

[Rapeseed Sensitivity Test 1 (Post-Sowing/Pre-Emergence Soil Treatment)]

Wild-type rapeseed plants (variety: Westar) and transgenic rapeseed plants comprising the wheat GST gene introduced therein were subjected to Rapeseed sensitivity test 1 in plastic pots (length: 8 cm; width: 8 cm; height: 6 cm). The test was carried out in Fujino soil (sandy loam soil), and 4 seeds of wild-type rapeseed and 8 seeds of transgenic rapeseed were sown in each pot (sowing depth: 1 cm). Water dispersible granules containing 50% pyroxasulfone were applied at 5 different doses of 1, 4, 16, 63, and 250 g a.i./ha (n=3). Immediately after pyroxasulfone treatment, about 1 mm of rain was fallen with the use of artificial rainfall device, and water was supplied from the bottom of the pots. Thereafter, water was supplied from the bottom of the pot when the soil surface was dried in the pot, according to need.

[Results and Discussion]

The difference in the sensitivity of rapeseed to pyroxasulfone applied pre-emergence was examined (temperature: 22° C., fluorescent light), and whether or not the transgenic rapeseed plant comprising wheat GST had pyroxasulfone resistance was evaluated in terms of the plant height, the herbicidal symptoms, and the cotyledon growth. Specifically, heights of the plants were measured 2 weeks after seeds sowing of rapeseed and pyroxasulfone application, and the inhibition was assessed by comparison to control plants grown in the absence of pyroxauslfone (n=4 to 12). The results are shown in FIGS. 37 to 39. In FIGS. 37 to 39, "TaGST" stands for a transgenic rapeseed plant comprising the TaQ8GTC0 gene. Values in the table in FIG. 38 are expressed as the mean±standard deviation (n=4 to 12).

Based on the inhibition obtained, shoot growth inhibition of transgenic rapeseed plants was found to be lower at the dose of 4 to 63 g a.i./ha, and, in particular, at 16 g a.i./ha, compared to that of wild-type rapeseed plants (the inhibition of 48.2% and 61.9% for transgenic plants and wild-type plants, respectively). Based on the herbicidal symptoms, cotyledons of wild-type rapeseed plants became dark green at the dose of 16 g a.i./ha or more, although such symptoms were not detected in transgenic rapeseed plants. While the cotyledon growth of the wild-type rapeseed plants was substantially completely inhibited at 16 g a.i./ha or more, the cotyledon of the transgenic rapeseed plants grew to a certain extent at 250 g a.i./ha (FIG. 39).

On the basis of the results demonstrated above, pyroxasulfone resistance of the transgenic rapeseed plants comprising the TaG8QGTC0 gene introduced therein was found to be superior to that of the wild-type rape plants as a result of the post-sowing/pre-emergence soil treatment test of pyroxasulfone (22° C., fluorescent light) in terms of the plant height, the herbicidal symptoms, and the cotyledon growth of the rapeseed plants.

[Rapeseed Sensitivity Test 2 (Agar Medium)]

On the basis of the results of the post-sowing/pre-emergence soil treatment test, transgenic rapeseed plants comprising the TaG8QGTC0 gene introduced therein were found to have pyroxasulfone resistance. In order to investigate the extent of pyroxasulfone resistance of the transgenic rapeseed plants comprising the TaG8QGTC0 gene introduced therein compared to wild-type plants, the growth of rapeseed was examined in an agar medium containing pyroxasulfone. Wild-type rapeseed plants (variety: Westar) and transgenic rapeseed plants comprising the TaQ8GTC0 gene introduced therein were subjected to the growth inhibitory test in an agar medium, so as to examine the resistance thereof to pyroxasulfone.

The medium (1 liter) used in the test was composed of 1× Murashige-Skoog (MS) media (a bag), thiamin hydrochloride (3 µg/ml), nicotinic acid (5 µg/ml), pyridoxin hydrochloride (0.5 µg/ml), and 1% (w/v) sucrose. The composition was added to a 1-liter beaker, a pH was adjusted to 5.7, and the volume of the composition was adjusted to 1 liter, followed by the addition of 8 g (0.8%) of agar. Thereafter, the composition was autoclaved, the temperature was cooled to room temperature, and pyroxasulfone (acetone solution) at a given concentration was added. The solution was poured into plant boxes in amounts of 50 ml (a plate comprising 30 ml solution without pyroxasulfone was also prepared).

When the rapeseed sensitivity test was performed, a necessary amount of dry seeds of rapeseed was agitated in 70% ethanol for 2 minutes and in hypochlorous acid (0.02% Triton-X-100) for 15 minutes, and the resultant was washed 10 times with sterile water. The seeds (about 30 seeds) were sowed on the surface of the medium without pyroxasulfone, the seeds were allowed to grow at 22° C. for 2 to 3 days, and 5 germinated seeds were then implanted in each media (in plant boxes). Thereafter, the plants were allowed to grow at 22° C. for 2 weeks and the data were obtained.

[Results and Discussion]

The sensitivity of rapeseed was examined in agar media comprising pyroxasulfone (0.1 µM, 1 µM, 10 µM, and 100 µM). The results are shown in FIGS. 40 to 43. FIG. 40 shows the results of wild-type rapeseed plants and values in the table are expressed as the mean±standard deviation (n=4 to 5). FIGS. 41 to 43 show the results of transgenic rapeseed plants comprising the TaG8QGTC0 gene introduced therein (indicated as "TaGST" in FIGS. 41 to 43). Values in the table in FIGS. 41 and 42 are expressed as the mean±standard deviation (n=4 to 5). Values in FIG. 43 are expressed as the means (n=4 to 5).

Based on the ratios for inhibiting the growth of plant heights and that of foliage leaves of rapeseed plants, the inhibition of wild-type rapeseed plants at a 0.1 µM (the inhibition ratio on plant height and the inhibition ratio on foliage leaf development of 8.9±2.8% and 8.4±1.4%, respectively) was equivalent to the inhibition ratio on transgenic rapeseed plants comprising wheat GST at 10 µM (the inhibition ratio on plant height and the inhibition ratio on foliage leaf development of 7.8±5.9% and 1.2±2.7%, respectively). Accordingly, pyroxasulfone resistance of the transgenic rapeseed plants comprising the TaG8QGTC0 gene introduced therein was found to be approximately 100 times stronger than that of wild-type rapeseed plants.

On the basis of the results of the sensitivity of the rapeseed plants comprising the TaG8QGTC gene introduced therein to pyroxasulfone, which was carried out via post-sowing/pre-emergence soil treatment in an agar medium, pyroxasulfone resistance of the transgenic rapeseed plants comprising the TaG8QGTC0 gene introduced therein was found to be stronger than that of wild-type rape plants by about 100 times. Thus, TaQ8GTC0 possessing the activity to metabolize pyroxasulfone in Examples 1 to 3 was found to function in rapeseed plants and confer pyroxasulfone resistance to rapeseed plants.

Example 6

In Example 6, the resistance of the transgenic *Arabidopsis thaliana* plants comprising the TaQ8GTC0 gene introduced therein (see Example 3) to high temperature stress were tested.

<Test of High Temperature Stress Resistance of Transgenic *Arabidopsis thaliana* Plants Comprising the TaQ8GTC0 Gene Introduced Therein>

The medium used for evaluating high temperature resistance of the transgenic *Arabidopsis thaliana* plants comprising the TaQ8GTC0 gene introduced therein produced in Example 3 was prepared as described below. At the outset, Murashige-Skoog (MS) media (a bag), thiamin hydrochloride (3 mg), nicotinic acid (5 mg), pyridoxin hydrochloride (0.5 mg), and sucrose (10 g) were added to a 1-liter beaker, a pH was adjusted to 5.7, and the volume of the mixture was adjusted to 1 liter, followed by the addition of 8 g (0.8%) of agar. The media were autoclaved, the temperature was cooled to room temperature, and the resulting medium (30 ml) was poured into the plate.

With the use of the resulting media, the transgenic *Arabidopsis thaliana* plants produced in Example 3 were used for the high temperature stress resistance test as described below. A necessary amount of dry seeds of *Arabidopsis thaliana* was agitated in 70% ethanol for 2 minutes and in hypochlorous acid (0.02% Triton-X-100) for 15 minutes, and the resultant was washed 10 times with sterile water. Subsequently, the seeds were suspended in 1 ml of the autoclaved 0.1% agar solution, and the suspension was thoroughly mixed to homogenous solution, and a total of 30 seeds were each placed on the medium surface. The resultant was sealed with a surgical tape and allowed to stand at 4° C. for 2 days. The resultant was transferred to 22° C. and allowed to grow for 11 days. Thereafter, the resultant was treated with high temperature stress (50° C. for 40 minutes) and then allowed to grow for additional 6 days.

[Results and Discussion]

Wild-type *Arabidopsis thaliana* plants (Columbia-0) were subjected to high temperature stress treatment as control samples, and whether or not the transgenic *Arabidopsis thaliana* plants comprising the TaQ8GTC0 gene introduced therein to high temperature stress was investigated in terms of plant phenotype using wild-type *Arabidopsis thaliana* plants as a control. Wild-type plants and 3 lineages of transgenic *Arabidopsis thaliana* plants (1-1-3, 1-1-5, and 1-2-12) were used for the test. As a result, the ratio of the wild-type plants of chlorosis (completely withered) by treatment of high temperature stress was found to be 74% (26/35), but that of the transgenic plants comprising the TaQ8GTC0 gene introduced therein (lineages 1-1-3, 1-1-5 and 1-2-12) was 0% (0/11), 24% (8/34) and 26% (10/38), respectively (values in parentheses: the number of plants of chlorosis/the number of plants tested). The results suggested that influence of high temperature treatment on the transgenic *Arabidopsis thaliana* plants comprising the TaQ8GTC0 gene introduced therein was weaker than that on wild-type plants and the transgenic *Arabidopsis thaliana* plants comprising the TaQ8GTC0 gene introduced therein had the resistance to high temperature stress. Considering that the transgenic rice plants comprising the TaQ8GTC0 gene introduced therein has high temperature stress resistance as described in Example 4, the TaQ8GTC0 gene was found to function in a wide variety of plants from monocotyledon to dicotyledon plants and confer both herbicide resistance and high temperature stress resistance to plants.

Example 7

In Example 7, whether or not the transgenic rapeseed plants (*Brassica napus*) comprising the TaQ8GTC0 gene introduced therein prepared in Example 5 had high temperature resistance was tested.

<Test of High Temperature Stress Resistance of Transgenic *Brassica napus* Plants Comprising the TaQ8GTC0 Gene Introduced Therein>

The medium used for evaluating high temperature resistance of the transgenic *Brassica napus* plants comprising the TaQ8GTC0 gene introduced therein produced in Example 5 was prepared as described below. At the outset, Murashige-Skoog (MS) media (a bag), thiamin hydrochloride (3 mg), nicotinic acid (5 mg), pyridoxine hydrochloride (0.5 mg), and sucrose (10 g) were added to a 1-liter beaker, a pH was adjusted to 5.7, and the volume of the mixture was adjusted to 1 liter, followed by the addition of 8 g (0.8%) of agar. The media were autoclaved, the temperature was cooled to room temperature, and the resulting medium (70 ml) was poured into the plant boxes.

With the use of the resulting media, the transgenic *Brassica napus* plants produced in Example 5 were used for the high temperature stress resistance test as described below. A necessary amount of dry seeds of *Brassica napus* was agitated in 70% ethanol for 2 minutes and in hypochlorous acid (0.02% Triton-X-100) for 15 minutes, and the resultant was washed 10 times with sterile water. Subsequently, about 5 seeds were sowed on the surface of the medium prepared above. The resultant was sealed with Parafilm and allowed to grow at 22° C. for 4 days. Thereafter, the resultant was treated with high temperature stress (50° C. for 1 hour or 50° C. for 2.5 hours) and then allowed to grow in isolated green houses for additional 4 days.

[Results and Discussion]

Wild-type *Brassica napus* plants (Westar) were subjected to high temperature stress treatment as control samples, and whether or not the transgenic *Brassica napus* plants comprising the TaQ8GTC0 gene introduced therein had high temperature resistance was investigated. In test 1 (treated at 50° C. for 1 hour), as a result, plant heights of the transgenic *Brassica napus* plants comprising the TaQ8GTC0 gene introduced therein were found to be significantly higher than those of wild-type plants (FIG. 44). Values in the table in FIG. 44 are expressed as the mean±standard deviation (n=3 to 7). In test 2 (treated at 50° C. for 2.5 hours), the ratio of the wild-type *Brassica napus* plants of chlorosis (completely withered) and the transgenic *Brassica napus* plants comprising the TaQ8GTC0 gene introduced therein were found to be 75% (¾) and 20% (⅕), respectively. That is, the ratio of the transgenic *Brassica napus* plants comprising the TaQ8GTC0 gene introduced therein of chlorosis was significantly lower than that of wild-type *Brassica napus* plants (values in parentheses: the number of plants of chlorosis/the number of plants tested). The results suggested that influence of high temperature treatment on the transgenic *Brassica napus* plants comprising the TaQ8GTC0 gene introduced therein was weaker than that on wild-type *Brassica napus* plants and the transgenic *Brassica napus* plants comprising the TaQ8GTC0 gene introduced therein prepared in Example 5 had the resistance to high temperature stress. Thus, the TaQ8GTC0 gene derived from wheat was found to function in *Brassica napus* plants and confer both herbicide resistance and high temperature stress resistance to plants.

The invention claimed is:

1. A method for cultivating a transgenic plant, the method comprising cultivating a transgenic plant in the presence of an isoxazoline derivative, wherein the transgenic plant comprises a transgene encoding a protein (a) or (b):
(a) a protein comprising the amino acid sequence as shown in SEQ ID NO: 2; or
(b) a protein comprising an amino acid sequence having 80% or higher identity to the amino acid sequence as shown in SEQ ID NO: 2 and having the activity of glutathione-S-transferase.

2. The method for cultivation according to claim 1, wherein the isoxazoline derivative is pyroxasulfone and/or fenoxasulfone.

3. The method for cultivation according to claim 1, wherein the transgenic plant is derived from a first plant having sensitivity to the isoxazoline derivative relative to the transgenic plant.

4. The method for cultivation according to claim 3, wherein the first plant having sensitivity to the isoxazoline derivative is a Gramineae.

5. The method for cultivation according to claim 4, wherein the first plant of the Gramineae is rice.

6. The method for cultivation according to claim 3, wherein the first plant having sensitivity to the isoxazoline derivative is a Brassicaceae, a Leguminosae, a Umbelliferae, a Amaranthaceae, a Labiatae, a Chenopodiaceae, a Rosaceae, a Compositae, a Solanaceae, or a Malvaceae.

7. The method for cultivation according to claim 6, wherein the first plant is *Brassica napus* or *Arabidopsis thaliana*.

8. A method for imparting isoxazoline-derivative resistance comprising introducing a nucleic acid encoding a protein (a) or (b) below into a first plant having sensitivity to an isoxazoline derivative to provide a transgenic plant, wherein the first plant has sensitivity to the isoxazoline derivative relative to the transgenic plant:
(a) a protein comprising the amino acid sequence as shown in SEQ ID NO: 2; or
(b) a protein comprising an amino acid sequence having 80% or higher identity to the amino acid sequence as shown in SEQ ID NO: 2 and having the activity of glutathione-S-transferase; and
growing the transgenic plant in the presence of the isoxazoline derivative.

9. The method for imparting resistance according to claim 8, wherein the isoxazoline derivative is pyroxasulfone and/or fenoxasulfone.

10. The method for imparting resistance according to claim 8, wherein the first plant having sensitivity to an isoxazoline derivative is a Gramineae.

11. The method for imparting resistance according to claim 10, wherein the first plant of the Gramineae is rice.

12. The method for imparting resistance according to claim 8, wherein the first plant having sensitivity to an isoxazoline derivative is a Brassicaceae, a Leguminosae, a Umbelliferae, a Amaranthaceae, a Labiatae, a Chenopodiaceae, a Rosaceae, a Compositae, a Solanaceae, or a Malvaceae.

13. The method for imparting resistance according to claim 12, wherein the first plant is *Brassica napus* or *Arabidopsis thaliana*.

14. A method for imparting environmental stress resistance comprising introducing a nucleic acid encoding a protein (a) or (b) below into a first plant to provide a transgenic plant, wherein the first plant has sensitivity to the environmental stress relative to the transgenic plant:
(a) a protein comprising the amino acid sequence as shown in SEQ ID NO: 2; or
(b) a protein comprising an amino acid sequence having 80% or higher identity to the amino acid sequence as shown in SEQ ID NO: 2 and having the activity of glutathione-S-transferase; and
growing the transgenic plant in the presence of an isoxazoline derivative.

15. The method for imparting resistance according to claim 14, wherein the environmental stress is high temperature stress.

16. The method for imparting resistance according to claim 14, wherein the first plant further has sensitivity to the isoxazoline derivative relative to the transgenic plant.

17. The method for imparting resistance according to claim 16, wherein the isoxazoline derivative is pyroxasulfone and/or fenoxasulfone.

18. The method for imparting resistance according to claim 14, wherein the first plant is a Gramineae.

19. The method for imparting resistance according to claim 18, wherein the first plant of the Gramineae is rice.

20. The method for imparting resistance according to claim 14, wherein the first plant is a Brassicaceae, a Leguminosae, a Umbelliferae, a Amaranthaceae, a Labiatae, a Chenopodiaceae, a Rosaceae, a Compositae, a Solanaceae, or a Malvaceae.

21. The method for imparting resistance according to claim 20, wherein the first plant is *Brassica napus* or *Arabidopsis thaliana*.

* * * * *

SEQUENCE LISTING

```
<160> NUMBER OF SEQ ID NOS: 51

<210> SEQ ID NO 1
<211> LENGTH: 669
<212> TYPE: DNA
<213> ORGANISM: Triticum aestivum
<220> FEATURE:
<221> NAME/KEY: CDS
<222> LOCATION: (1)..(669)

<400> SEQUENCE: 1 atg gcg ccg gcg gtg aag gtg tac ggg tgg gcc gtg tcg ccg ttc gtg      48
Met Ala Pro Ala Val Lys Val Tyr Gly Trp Ala Val Ser Pro Phe Val
1               5                   10                  15 gcg cgc cca ctg ctg tgc ctg gag gag gcc ggc gtc gag tac gag ctc      96
Ala Arg Pro Leu Leu Cys Leu Glu Glu Ala Gly Val Glu Tyr Glu Leu
            20                  25                  30 gtg tcc atg agc cgc gcg gcc ggc gac cac cgc cag ccg gac ttc ctc     144
Val Ser Met Ser Arg Ala Ala Gly Asp His Arg Gln Pro Asp Phe Leu
        35                  40                  45 gcc cgg aac ccc ttc ggc cag gtc ccc gtc ctc gag gac ggc gac ctc     192
Ala Arg Asn Pro Phe Gly Gln Val Pro Val Leu Glu Asp Gly Asp Leu
    50                  55                  60 acc ctc ttc gag tcg cgc gcg atc gcg agg cac gtg ctc cgg aag cac     240
Thr Leu Phe Glu Ser Arg Ala Ile Ala Arg His Val Leu Arg Lys His
65                  70                  75                  80 aag ccg gag ctg ctg ggc tgc ggc tcg ccg gag gcg gag gcg atg gtg     288
Lys Pro Glu Leu Leu Gly Cys Gly Ser Pro Glu Ala Glu Ala Met Val
                85                  90                  95 gac gtg tgg ctg gag gtg gag gcc cac cag tac aac ccc gcg gcc agc     336
Asp Val Trp Leu Glu Val Glu Ala His Gln Tyr Asn Pro Ala Ala Ser
            100                 105                 110
```

```
gcc atc gtg gtg cag tgc atc atc ttg ccg cta ctg ggc ggc gcg cgg      384
Ala Ile Val Val Gln Cys Ile Ile Leu Pro Leu Leu Gly Gly Ala Arg
    115                 120                 125 gac cag gcg gtg gtg gac gag aac gta gcc aag ctc aag aag gtg ctg      432
Asp Gln Ala Val Val Asp Glu Asn Val Ala Lys Leu Lys Lys Val Leu
130                 135                 140 gag gtg tac gag gca cgg ctg tcg gcg tcc agg tac ctc gcc ggg gac      480
Glu Val Tyr Glu Ala Arg Leu Ser Ala Ser Arg Tyr Leu Ala Gly Asp
145                 150                 155                 160 gac atc agc ctc gcc gac ctc agc cac ttc ccc ttc acg cgc tac ttc      528
Asp Ile Ser Leu Ala Asp Leu Ser His Phe Pro Phe Thr Arg Tyr Phe
            165                 170                 175 atg gag acg gag tac gcg ccg ctg gtg gcg gag ctc ccc cac gtg aac      576
Met Glu Thr Glu Tyr Ala Pro Leu Val Ala Glu Leu Pro His Val Asn
        180                 185                 190 gcg tgg tgg gag ggg ctc aag gcc agg ccg gcc gcg agg aag gtg acg      624
Ala Trp Trp Glu Gly Leu Lys Ala Arg Pro Ala Ala Arg Lys Val Thr
    195                 200                 205 gag ctc atg ccg ccg gac ctt ggg ctt gga aag aaa gca gag tag          669
Glu Leu Met Pro Pro Asp Leu Gly Leu Gly Lys Lys Ala Glu
210                 215                 220

<210> SEQ ID NO 2
<211> LENGTH: 222
<212> TYPE: PRT
<213> ORGANISM: Triticum aestivum

<400> SEQUENCE: 2

Met Ala Pro Ala Val Lys Val Tyr Gly Trp Ala Val Ser Pro Phe Val
1               5                   10                  15

Ala Arg Pro Leu Leu Cys Leu Glu Glu Ala Gly Val Glu Tyr Glu Leu
            20                  25                  30

Val Ser Met Ser Arg Ala Ala Gly Asp His Arg Gln Pro Asp Phe Leu
        35                  40                  45

Ala Arg Asn Pro Phe Gly Gln Val Pro Val Leu Glu Asp Gly Asp Leu
    50                  55                  60

Thr Leu Phe Glu Ser Arg Ala Ile Ala Arg His Val Leu Arg Lys His
65                  70                  75                  80

Lys Pro Glu Leu Leu Gly Cys Gly Ser Pro Glu Ala Glu Ala Met Val
                85                  90                  95

Asp Val Trp Leu Glu Val Glu Ala His Gln Tyr Asn Pro Ala Ala Ser
            100                 105                 110

Ala Ile Val Val Gln Cys Ile Ile Leu Pro Leu Leu Gly Gly Ala Arg
        115                 120                 125

Asp Gln Ala Val Val Asp Glu Asn Val Ala Lys Leu Lys Lys Val Leu
    130                 135                 140

Glu Val Tyr Glu Ala Arg Leu Ser Ala Ser Arg Tyr Leu Ala Gly Asp
145                 150                 155                 160

Asp Ile Ser Leu Ala Asp Leu Ser His Phe Pro Phe Thr Arg Tyr Phe
                165                 170                 175

Met Glu Thr Glu Tyr Ala Pro Leu Val Ala Glu Leu Pro His Val Asn
            180                 185                 190

Ala Trp Trp Glu Gly Leu Lys Ala Arg Pro Ala Ala Arg Lys Val Thr
        195                 200                 205

Glu Leu Met Pro Pro Asp Leu Gly Leu Gly Lys Lys Ala Glu
    210                 215                 220
```

```
<210> SEQ ID NO 3
<211> LENGTH: 30
<212> TYPE: DNA
<213> ORGANISM: Artificial
<220> FEATURE:
<223> OTHER INFORMATION: Synthetic DNA

<400> SEQUENCE: 3
aaaaaacata tggcgccggc ggtgaaggtg                                      30

<210> SEQ ID NO 4
<211> LENGTH: 30
<212> TYPE: DNA
<213> ORGANISM: Artificial
<220> FEATURE:
<223> OTHER INFORMATION: Synthetic DNA

<400> SEQUENCE: 4
aaaaaaggat ccctactctg ctttctttcc                                      30

<210> SEQ ID NO 5
<211> LENGTH: 30
<212> TYPE: DNA
<213> ORGANISM: Artificial
<220> FEATURE:
<223> OTHER INFORMATION: Synthetic DNA

<400> SEQUENCE: 5
aaaaaagtcg acatggcgcc ggcggtgaag                                      30

<210> SEQ ID NO 6
<211> LENGTH: 32
<212> TYPE: DNA
<213> ORGANISM: Artificial
<220> FEATURE:
<223> OTHER INFORMATION: Synthetic DNA

<400> SEQUENCE: 6
aaaaaagcgg ccgcctactc tgctttcttt cc                                   32

<210> SEQ ID NO 7
<211> LENGTH: 22
<212> TYPE: DNA
<213> ORGANISM: Artificial
<220> FEATURE:
<223> OTHER INFORMATION: Synthetic DNA

<400> SEQUENCE: 7
cacgtgctcc ggaagcacaa gc                                              22

<210> SEQ ID NO 8
<211> LENGTH: 20
<212> TYPE: DNA
<213> ORGANISM: Artificial
<220> FEATURE:
<223> OTHER INFORMATION: Synthetic DNA

<400> SEQUENCE: 8
ccggcaacag gattcaatct                                                 20

<210> SEQ ID NO 9
<211> LENGTH: 30
<212> TYPE: DNA
<213> ORGANISM: Artificial
<220> FEATURE:
<223> OTHER INFORMATION: Synthetic DNA
```

<400> SEQUENCE: 9
aaaaaatcta gaaaagtgca gggcaaattc                                30

<210> SEQ ID NO 10
<211> LENGTH: 30
<212> TYPE: DNA
<213> ORGANISM: Artificial
<220> FEATURE:
<223> OTHER INFORMATION: Synthetic DNA

<400> SEQUENCE: 10
aaaaaactta agctatggta tgttcccact                                30

<210> SEQ ID NO 11
<211> LENGTH: 30
<212> TYPE: DNA
<213> ORGANISM: Artificial
<220> FEATURE:
<223> OTHER INFORMATION: Synthetic DNA

<400> SEQUENCE: 11
aaaaaatcta gaatcttctt ctccgacgag                                30

<210> SEQ ID NO 12
<211> LENGTH: 30
<212> TYPE: DNA
<213> ORGANISM: Artificial
<220> FEATURE:
<223> OTHER INFORMATION: Synthetic DNA

<400> SEQUENCE: 12
aaaaaactta agctacttgg cgccaaactt                                30

<210> SEQ ID NO 13
<211> LENGTH: 30
<212> TYPE: DNA
<213> ORGANISM: Artificial
<220> FEATURE:
<223> OTHER INFORMATION: Synthetic DNA

<400> SEQUENCE: 13
aaaaaatcta gaatggagcc tatgaaggtg                                30

<210> SEQ ID NO 14
<211> LENGTH: 30
<212> TYPE: DNA
<213> ORGANISM: Artificial
<220> FEATURE:
<223> OTHER INFORMATION: Synthetic DNA

<400> SEQUENCE: 14
aaaaaactta agtcatggta ttctcccgct                                30

<210> SEQ ID NO 15
<211> LENGTH: 28
<212> TYPE: DNA
<213> ORGANISM: Artificial
<220> FEATURE:
<223> OTHER INFORMATION: Synthetic DNA

<400> SEQUENCE: 15
aaaaaatcta gatcgtttcg aggccgat                                  28

<210> SEQ ID NO 16
<211> LENGTH: 30

```
<212> TYPE: DNA
<213> ORGANISM: Artificial
<220> FEATURE:
<223> OTHER INFORMATION: Synthetic DNA

<400> SEQUENCE: 16
aaaaaactta agtcacttgg ccccgaactt                                    30

<210> SEQ ID NO 17
<211> LENGTH: 29
<212> TYPE: DNA
<213> ORGANISM: Artificial
<220> FEATURE:
<223> OTHER INFORMATION: Synthetic DNA

<400> SEQUENCE: 17
aaaaaatcta gataccagcc acgtcgctt                                     29

<210> SEQ ID NO 18
<211> LENGTH: 30
<212> TYPE: DNA
<213> ORGANISM: Artificial
<220> FEATURE:
<223> OTHER INFORMATION: Synthetic DNA

<400> SEQUENCE: 18
aaaaaactta agtcacttgg ccccgaactt                                    30

<210> SEQ ID NO 19
<211> LENGTH: 28
<212> TYPE: DNA
<213> ORGANISM: Artificial
<220> FEATURE:
<223> OTHER INFORMATION: Synthetic DNA

<400> SEQUENCE: 19
aaaaaatcta gagttgggtc tgggacac                                      28

<210> SEQ ID NO 20
<211> LENGTH: 30
<212> TYPE: DNA
<213> ORGANISM: Artificial
<220> FEATURE:
<223> OTHER INFORMATION: Synthetic DNA

<400> SEQUENCE: 20
aaaaaactta agtcaagcag atggcttcat                                    30

<210> SEQ ID NO 21
<211> LENGTH: 30
<212> TYPE: DNA
<213> ORGANISM: Artificial
<220> FEATURE:
<223> OTHER INFORMATION: Synthetic DNA

<400> SEQUENCE: 21
aaaaaatcta gaatggccga ggagaagaag                                    30

<210> SEQ ID NO 22
<211> LENGTH: 30
<212> TYPE: DNA
<213> ORGANISM: Artificial
<220> FEATURE:
<223> OTHER INFORMATION: Synthetic DNA

<400> SEQUENCE: 22
```
aaaaaactta agctactcga tgcccagcct                                    30

<210> SEQ ID NO 23
<211> LENGTH: 30
<212> TYPE: DNA
<213> ORGANISM: Artificial
<220> FEATURE:
<223> OTHER INFORMATION: Synthetic DNA

<400> SEQUENCE: 23
aaaaaagtcg acatggcggc ggcggcggag                                    30

<210> SEQ ID NO 24
<211> LENGTH: 33
<212> TYPE: DNA
<213> ORGANISM: Artificial
<220> FEATURE:
<223> OTHER INFORMATION: Synthetic DNA

<400> SEQUENCE: 24
aaaaaagcgg ccgctcactt ggccccgaac ttg                                33

<210> SEQ ID NO 25
<211> LENGTH: 30
<212> TYPE: DNA
<213> ORGANISM: Artificial
<220> FEATURE:
<223> OTHER INFORMATION: Synthetic DNA

<400> SEQUENCE: 25
aaaaaagtcg acatggcgcc gccgatgaag                                    30

<210> SEQ ID NO 26
<211> LENGTH: 33
<212> TYPE: DNA
<213> ORGANISM: Artificial
<220> FEATURE:
<223> OTHER INFORMATION: Synthetic DNA

<400> SEQUENCE: 26
aaaaaagcgg ccgcctatgg tatgttcccg ctg                                33

<210> SEQ ID NO 27
<211> LENGTH: 30
<212> TYPE: DNA
<213> ORGANISM: Artificial
<220> FEATURE:
<223> OTHER INFORMATION: Synthetic DNA

<400> SEQUENCE: 27
aaaaaatcta gagatcttca agaagcggaa                                    30

<210> SEQ ID NO 28
<211> LENGTH: 35
<212> TYPE: DNA
<213> ORGANISM: Artificial
<220> FEATURE:
<223> OTHER INFORMATION: Synthetic DNA

<400> SEQUENCE: 28
aaaaaagaat tctcacttct ctgccttctt tccga                              35

<210> SEQ ID NO 29
<211> LENGTH: 20
<212> TYPE: DNA
<213> ORGANISM: Artificial

<220> FEATURE:
<223> OTHER INFORMATION: Synthetic DNA

<400> SEQUENCE: 29
gacctcacca tcttcgagtc                                                  20

<210> SEQ ID NO 30
<211> LENGTH: 18
<212> TYPE: DNA
<213> ORGANISM: Artificial
<220> FEATURE:
<223> OTHER INFORMATION: Synthetic DNA

<400> SEQUENCE: 30
ctcgtacacg tcgaacag                                                    18

<210> SEQ ID NO 31
<211> LENGTH: 675
<212> TYPE: DNA
<213> ORGANISM: Triticum aestivum
<220> FEATURE:
<221> NAME/KEY: CDS
<222> LOCATION: (1)..(675)

<400> SEQUENCE: 31

```
atg gcg gcg ccg gcg gtg aag gtg cac ggg tgg gcg atg tcg ccg ttc      48
Met Ala Ala Pro Ala Val Lys Val His Gly Trp Ala Met Ser Pro Phe
1               5                  10                  15 gtg gcg cgc gcg ttg ctg tgc ctg gag gag gcc ggc gtg gag tac gag      96
Val Ala Arg Ala Leu Leu Cys Leu Glu Glu Ala Gly Val Glu Tyr Glu
            20                  25                  30 ctc gtc ccc atg agc cgc gag gcc ggc gac cac cgc cag ccg gac ttc     144
Leu Val Pro Met Ser Arg Glu Ala Gly Asp His Arg Gln Pro Asp Phe
        35                  40                  45 ctc gcc agg aac ccc ttc ggc cag gtc ccc gtt ctc gag gac ggc gac     192
Leu Ala Arg Asn Pro Phe Gly Gln Val Pro Val Leu Glu Asp Gly Asp
    50                  55                  60 ctc acc atc ttc gaa tcg cgc gcc gtc gcg agg cac gtg ctg cgc aag     240
Leu Thr Ile Phe Glu Ser Arg Ala Val Ala Arg His Val Leu Arg Lys
65                  70                  75                  80 cac aag ccg gag ctg ctg ggc tcc ggc tcg ccg gag tcg gcg gcg aag     288
His Lys Pro Glu Leu Leu Gly Ser Gly Ser Pro Glu Ser Ala Ala Lys
                85                  90                  95 gtg gac gtg tgg ctg gag gtg gag gcg cac cag cac cag acc ccg gcg     336
Val Asp Val Trp Leu Glu Val Glu Ala His Gln His Gln Thr Pro Ala
            100                 105                 110 ggc acc atc gtg atg cag tgc atc ctc acc ccg ttc ctc ggc tgc gag     384
Gly Thr Ile Val Met Gln Cys Ile Leu Thr Pro Phe Leu Gly Cys Glu
        115                 120                 125 cgc gac cag acc gcc atc gac gag aac gcg gca aag ctg acg aag ctg     432
Arg Asp Gln Thr Ala Ile Asp Glu Asn Ala Ala Lys Leu Thr Lys Leu
    130                 135                 140 ttc gac gtg tac gag gcg cgg ctg tcg gcg tcg agg tac ctc gcc ggg     480
Phe Asp Val Tyr Glu Ala Arg Leu Ser Ala Ser Arg Tyr Leu Ala Gly
145                 150                 155                 160 gac tcc ctc agc ctc gcc gac ctc agc cac ttc ccg ctc atg cgc tac     528
Asp Ser Leu Ser Leu Ala Asp Leu Ser His Phe Pro Leu Met Arg Tyr
                165                 170                 175 ttc atg gac acc gag tac gcg tcg ctg gtg gtg gag cgc ccg cac gtg     576
Phe Met Asp Thr Glu Tyr Ala Ser Leu Val Val Glu Arg Pro His Val
            180                 185                 190 aag gtg tgg tgg gag gag ctc aag gcc agg ccg gcg gcg aag agg gtg     624
Lys Val Trp Trp Glu Glu Leu Lys Ala Arg Pro Ala Ala Lys Arg Val
```

| Lys | Val | Trp | Trp | Glu | Glu | Leu | Lys | Ala | Arg | Pro | Ala | Ala | Lys | Arg | Val |
|---|---|---|---|---|---|---|---|---|---|---|---|---|---|---|---|
| | | 195 | | | | 200 | | | | 205 | | | | | |

```
acg gag ttc atg ccg cca aac ttc ggg ttc gga aag aag gca gag aag    672
Thr Glu Phe Met Pro Pro Asn Phe Gly Phe Gly Lys Lys Ala Glu Lys
210                 215                 220 tga                                                                 675
```

```
<210> SEQ ID NO 32
<211> LENGTH: 224
<212> TYPE: PRT
<213> ORGANISM: Triticum aestivum

<400> SEQUENCE: 32
```

Met Ala Ala Pro Ala Val Lys Val His Gly Trp Ala Met Ser Pro Phe
1               5                   10                  15

Val Ala Arg Ala Leu Leu Cys Leu Glu Glu Ala Gly Val Glu Tyr Glu
            20                  25                  30

Leu Val Pro Met Ser Arg Glu Ala Gly Asp His Arg Gln Pro Asp Phe
        35                  40                  45

Leu Ala Arg Asn Pro Phe Gly Gln Val Pro Val Leu Glu Asp Gly Asp
    50                  55                  60

Leu Thr Ile Phe Glu Ser Arg Ala Val Ala Arg His Val Leu Arg Lys
65                  70                  75                  80

His Lys Pro Glu Leu Leu Gly Ser Gly Ser Pro Glu Ser Ala Ala Lys
                85                  90                  95

Val Asp Val Trp Leu Glu Val Glu Ala His Gln His Gln Thr Pro Ala
            100                 105                 110

Gly Thr Ile Val Met Gln Cys Ile Leu Thr Pro Phe Leu Gly Cys Glu
        115                 120                 125

Arg Asp Gln Thr Ala Ile Asp Glu Asn Ala Ala Lys Leu Thr Lys Leu
    130                 135                 140

Phe Asp Val Tyr Glu Ala Arg Leu Ser Ala Ser Arg Tyr Leu Ala Gly
145                 150                 155                 160

Asp Ser Leu Ser Leu Ala Asp Leu Ser His Phe Pro Leu Met Arg Tyr
                165                 170                 175

Phe Met Asp Thr Glu Tyr Ala Ser Leu Val Val Glu Arg Pro His Val
            180                 185                 190

Lys Val Trp Trp Glu Glu Leu Lys Ala Arg Pro Ala Ala Lys Arg Val
        195                 200                 205

Thr Glu Phe Met Pro Pro Asn Phe Gly Phe Gly Lys Lys Ala Glu Lys
    210                 215                 220

```
<210> SEQ ID NO 33
<211> LENGTH: 675
<212> TYPE: DNA
<213> ORGANISM: Triticum aestivum
<220> FEATURE:
<221> NAME/KEY: CDS
<222> LOCATION: (1)..(675)

<400> SEQUENCE: 33
```

```
atg gcg gcg ccg gcg gtg aag gtg tac ggg tgg gcg atg tcg ccg ttc    48
Met Ala Ala Pro Ala Val Lys Val Tyr Gly Trp Ala Met Ser Pro Phe
1               5                   10                  15 gtg gcg cgc gcg ctg ctg tgc ctg gag gag gcc ggc gtg gag tac gag    96
Val Ala Arg Ala Leu Leu Cys Leu Glu Glu Ala Gly Val Glu Tyr Glu
            20                  25                  30 ctc gtc ccc atg agc cgc gag gcc ggc gac cac cgc cag ccc gac ttc    144
```

```
Leu Val Pro Met Ser Arg Glu Ala Gly Asp His Arg Gln Pro Asp Phe
            35                  40                  45 ctc gcc cgg aac ccc ttc ggc cag gtc ccc gtt ctc gag gac ggc gac   192
Leu Ala Arg Asn Pro Phe Gly Gln Val Pro Val Leu Glu Asp Gly Asp
     50                  55                  60 ctc acc atc ttc gag tcg cgc gcc gtc gcg agg cac gtg ctg cgc aag   240
Leu Thr Ile Phe Glu Ser Arg Ala Val Ala Arg His Val Leu Arg Lys
 65                  70                  75                  80 cac aaa ccg gag ctg ctg ggc tcc ggc tcg ccg gag tcg gcg gcg atg   288
His Lys Pro Glu Leu Leu Gly Ser Gly Ser Pro Glu Ser Ala Ala Met
                 85                  90                  95 gtg gac gtg tgg ctg gag gtg gag gcc cac cag cac cag acc ccg gcg   336
Val Asp Val Trp Leu Glu Val Glu Ala His Gln His Gln Thr Pro Ala
            100                 105                 110 ggc acc atc gtc atg cag tgc atc ctc acc ccg ttc ctc ggc tgc cag   384
Gly Thr Ile Val Met Gln Cys Ile Leu Thr Pro Phe Leu Gly Cys Gln
        115                 120                 125 cgc gac cag gcc gcc atc gac gag aac gcg gca aag ctg acg aat ctg   432
Arg Asp Gln Ala Ala Ile Asp Glu Asn Ala Ala Lys Leu Thr Asn Leu
    130                 135                 140 ttc gac gtg tac gag gcg cgc ctg tcg gcg tcg agg tac ctt gcc ggg   480
Phe Asp Val Tyr Glu Ala Arg Leu Ser Ala Ser Arg Tyr Leu Ala Gly
145                 150                 155                 160 gag gcg gtc agc ctc gcg gac ctc agc cac ttc ccg ttc atg cga tac   528
Glu Ala Val Ser Leu Ala Asp Leu Ser His Phe Pro Phe Met Arg Tyr
                165                 170                 175 ttc atg gac acc gag tac gcg tcg ctg gtg gag gag cgc ccg cac gtg   576
Phe Met Asp Thr Glu Tyr Ala Ser Leu Val Glu Glu Arg Pro His Val
            180                 185                 190 aag gcg tgg tgg gag gag ttc aag gcc agc ccg gcg gcg aag agg gtg   624
Lys Ala Trp Trp Glu Glu Phe Lys Ala Ser Pro Ala Ala Lys Arg Val
        195                 200                 205 acg gag ttc atg ccg cca aac ttc ggg ttc gga aag aag gca gag aag   672
Thr Glu Phe Met Pro Pro Asn Phe Gly Phe Gly Lys Lys Ala Glu Lys
    210                 215                 220 tga                                                               675

<210> SEQ ID NO 34
<211> LENGTH: 224
<212> TYPE: PRT
<213> ORGANISM: Triticum aestivum

<400> SEQUENCE: 34

Met Ala Ala Pro Ala Val Lys Val Tyr Gly Trp Ala Met Ser Pro Phe
  1               5                  10                  15

Val Ala Arg Ala Leu Leu Cys Leu Glu Glu Ala Gly Val Glu Tyr Glu
             20                  25                  30

Leu Val Pro Met Ser Arg Glu Ala Gly Asp His Arg Gln Pro Asp Phe
            35                  40                  45

Leu Ala Arg Asn Pro Phe Gly Gln Val Pro Val Leu Glu Asp Gly Asp
     50                  55                  60

Leu Thr Ile Phe Glu Ser Arg Ala Val Ala Arg His Val Leu Arg Lys
 65                  70                  75                  80

His Lys Pro Glu Leu Leu Gly Ser Gly Ser Pro Glu Ser Ala Ala Met
                 85                  90                  95

Val Asp Val Trp Leu Glu Val Glu Ala His Gln His Gln Thr Pro Ala
            100                 105                 110

Gly Thr Ile Val Met Gln Cys Ile Leu Thr Pro Phe Leu Gly Cys Gln
```

```
                115                 120                 125
Arg Asp Gln Ala Ala Ile Asp Glu Asn Ala Ala Lys Leu Thr Asn Leu
    130                 135                 140

Phe Asp Val Tyr Glu Ala Arg Leu Ser Ala Ser Arg Tyr Leu Ala Gly
145                 150                 155                 160

Glu Ala Val Ser Leu Ala Asp Leu Ser His Phe Pro Phe Met Arg Tyr
                165                 170                 175

Phe Met Asp Thr Glu Tyr Ala Ser Leu Val Glu Glu Arg Pro His Val
            180                 185                 190

Lys Ala Trp Trp Glu Glu Phe Lys Ala Ser Pro Ala Ala Lys Arg Val
        195                 200                 205

Thr Glu Phe Met Pro Pro Asn Phe Gly Phe Gly Lys Lys Ala Glu Lys
    210                 215                 220

<210> SEQ ID NO 35
<211> LENGTH: 33
<212> TYPE: DNA
<213> ORGANISM: Artificial
<220> FEATURE:
<223> OTHER INFORMATION: Synthetic DNA

<400> SEQUENCE: 35
aaaaaacata tggcggcgcc ggcggtgaag gtg                                  33

<210> SEQ ID NO 36
<211> LENGTH: 35
<212> TYPE: DNA
<213> ORGANISM: Artificial
<220> FEATURE:
<223> OTHER INFORMATION: Synthetic DNA

<400> SEQUENCE: 36
aaaaaagaat tctcacttct ctgccttctt tccga                               35

<210> SEQ ID NO 37
<211> LENGTH: 212
<212> TYPE: PRT
<213> ORGANISM: Arabidopsis thaliana

<400> SEQUENCE: 37

Met Ala Gly Ile Lys Val Phe Gly His Pro Ala Ser Ile Ala Thr Arg
1               5                   10                  15

Arg Val Leu Ile Ala Leu His Glu Lys Asn Leu Asp Phe Glu Leu Val
            20                  25                  30

His Val Glu Leu Lys Asp Gly Glu His Lys Lys Glu Pro Phe Leu Ser
        35                  40                  45

Arg Asn Pro Phe Gly Gln Val Pro Ala Phe Glu Asp Gly Asp Leu Lys
    50                  55                  60

Leu Phe Glu Ser Arg Ala Ile Thr Gln Tyr Ile Ala His Arg Tyr Glu
65                  70                  75                  80

Asn Gln Gly Thr Asn Leu Leu Gln Thr Asp Ser Lys Asn Ile Ser Gln
                85                  90                  95

Tyr Ala Ile Met Ala Ile Gly Met Gln Val Glu Asp His Gln Phe Asp
            100                 105                 110

Pro Val Ala Ser Lys Leu Ala Phe Glu Gln Ile Phe Lys Ser Ile Tyr
        115                 120                 125

Gly Leu Thr Thr Asp Glu Ala Val Val Ala Glu Glu Ala Lys Leu
    130                 135                 140
```

-continued

```
Ala Lys Val Leu Asp Val Tyr Glu Ala Arg Leu Lys Glu Phe Lys Tyr
145                 150                 155                 160

Leu Ala Gly Glu Thr Phe Thr Leu Thr Asp Leu His His Ile Pro Ala
                165                 170                 175

Ile Gln Tyr Leu Leu Gly Thr Pro Thr Lys Lys Leu Phe Thr Glu Arg
                180                 185                 190

Pro Arg Val Asn Glu Trp Val Ala Glu Ile Thr Lys Arg Pro Ala Ser
                195                 200                 205

Glu Lys Val Gln
    210
```

<210> SEQ ID NO 38
<211> LENGTH: 215
<212> TYPE: PRT
<213> ORGANISM: Populus trichocarpa

<400> SEQUENCE: 38

```
Met Ala Thr Pro Val Thr Ile Tyr Gly Pro Pro Leu Ser Thr Ala Val
1               5                   10                  15

Ser Arg Val Leu Ala Thr Leu Ile Glu Lys Asp Val Pro Phe His Leu
                20                  25                  30

Val Pro Ile Asp Leu Ser Lys Gly Glu Gln Lys Lys Pro Glu Tyr Leu
                35                  40                  45

Lys Ile Gln Pro Phe Gly Gln Val Pro Ala Phe Lys Asp Glu Ser Ile
    50                  55                  60

Thr Leu Phe Glu Ser Arg Ala Ile Cys Arg Tyr Ile Cys Asp Lys Tyr
65                  70                  75                  80

Ala Asp Lys Gly Asn Arg Ser Leu Tyr Gly Thr Asp Ile Leu Ser Lys
                85                  90                  95

Ala Asn Ile Asp Gln Trp Val Glu Thr Asp Gly Gln Thr Phe Gly Pro
                100                 105                 110

Pro Ser Gly Asp Leu Val His Asp Leu Leu Phe Ser Ser Val Pro Val
                115                 120                 125

Asp Glu Ala Leu Ile Lys Lys Asn Val Asp Lys Leu Ala Lys Val Leu
130                 135                 140

Asp Ile Tyr Glu Gln Lys Leu Gly Gln Thr Arg Phe Leu Ala Gly Asp
145                 150                 155                 160

Glu Phe Ser Phe Ala Asp Leu Ser His Leu Pro Asn Gly Asp Tyr Leu
                165                 170                 175

Val Asn Ser Thr Asp Lys Gly Tyr Leu Phe Thr Ser Arg Lys Asn Val
                180                 185                 190

Asn Arg Trp Trp Thr Glu Ile Ser Asn Arg Glu Ser Trp Lys Lys Val
                195                 200                 205

Leu Glu Met Arg Lys Asn Ala
    210                 215
```

<210> SEQ ID NO 39
<211> LENGTH: 214
<212> TYPE: PRT
<213> ORGANISM: Zea mays

<400> SEQUENCE: 39

```
Met Ala Pro Met Lys Leu Tyr Gly Ala Val Met Ser Trp Asn Leu Thr
1               5                   10                  15

Arg Cys Ala Thr Ala Leu Glu Glu Ala Gly Ser Asp Tyr Glu Ile Val
                20                  25                  30
```

```
Pro Ile Asn Phe Ala Thr Ala Glu His Lys Ser Pro Glu His Leu Val
        35                  40                  45

Arg Asn Pro Phe Gly Gln Val Pro Ala Leu Gln Asp Gly Asp Leu Tyr
 50                  55                  60

Leu Phe Glu Ser Arg Ala Ile Cys Lys Tyr Ala Ala Arg Lys Asn Lys
 65                  70                  75                  80

Pro Glu Leu Leu Arg Glu Gly Asn Leu Glu Glu Ala Ala Met Val Asp
                 85                  90                  95

Val Trp Ile Glu Val Glu Ala Asn Gln Tyr Thr Ala Ala Leu Asn Pro
                100                 105                 110

Ile Leu Phe Gln Val Leu Ile Ser Pro Met Leu Gly Gly Thr Thr Asp
                115                 120                 125

Gln Lys Val Val Asp Glu Asn Leu Glu Lys Leu Lys Lys Val Leu Glu
    130                 135                 140

Val Tyr Glu Ala Arg Leu Thr Lys Cys Lys Tyr Leu Ala Gly Asp Phe
145                 150                 155                 160

Leu Ser Leu Ala Asp Leu Asn His Val Ser Val Thr Leu Cys Leu Phe
                165                 170                 175

Ala Thr Pro Tyr Ala Ser Val Leu Asp Ala Tyr Pro His Val Lys Ala
                180                 185                 190

Trp Trp Ser Gly Leu Met Glu Arg Pro Ser Val Gln Lys Val Ala Ala
                195                 200                 205

Leu Met Lys Pro Ser Ala
    210

<210> SEQ ID NO 40
<211> LENGTH: 212
<212> TYPE: PRT
<213> ORGANISM: Triticum aestivum

<400> SEQUENCE: 40

Met Ala Pro Val Lys Leu Tyr Gly Ala Thr Leu Ser Trp Asn Val Thr
 1               5                  10                  15

Arg Cys Val Ala Ala Leu Glu Glu Ala Gly Val Gln Tyr Glu Ile Val
                 20                  25                  30

Pro Ile Asn Phe Gly Thr Gly Glu His Lys Ser Pro Asp His Leu Ala
        35                  40                  45

Arg Asn Pro Phe Gly Gln Val Pro Ala Leu Gln Asp Gly Asp Leu Tyr
 50                  55                  60

Val Phe Glu Ser Arg Ala Ile Cys Lys Tyr Ala Cys Arg Lys Asn Lys
 65                  70                  75                  80

Pro Glu Leu Leu Lys Glu Gly Asp Ile Lys Glu Ser Ala Met Val Asp
                 85                  90                  95

Val Trp Leu Glu Val Glu Ala His Gln Tyr Thr Ala Ala Leu Ser Pro
                100                 105                 110

Ile Leu Phe Glu Cys Leu Ile His Pro Met Leu Gly Gly Ala Thr Asp
                115                 120                 125

Gln Lys Val Ile Asp Asp Asn Leu Val Lys Ile Lys Asn Val Leu Ala
    130                 135                 140

Val Tyr Glu Ala His Leu Ser Lys Ser Lys Tyr Leu Ala Gly Asp Phe
145                 150                 155                 160

Leu Ser Leu Ala Asp Leu Asn His Val Ser Val Thr Leu Cys Leu Ala
                165                 170                 175

Ala Thr Pro Tyr Ala Ser Leu Phe Asp Ala Tyr Pro His Val Lys Ala
                180                 185                 190
```

Trp Trp Thr Asp Leu Leu Ala Arg Pro Ser Val Gln Lys Val Ala Ala
            195                 200                 205

Leu Met Lys Pro
        210

<210> SEQ ID NO 41
<211> LENGTH: 222
<212> TYPE: PRT
<213> ORGANISM: Triticum aestivum

<400> SEQUENCE: 41

Met Glu Pro Met Lys Val Tyr Gly Trp Ala Val Ser Pro Trp Met Ala
1               5                   10                  15

Arg Val Leu Val Ser Leu Glu Glu Ala Gly Ala Asp Tyr Glu Leu Val
            20                  25                  30

Pro Met Ser Arg Asn Gly Gly Asp His Arg Arg Pro Glu His Leu Ala
        35                  40                  45

Arg Asn Pro Phe Gly Glu Ile Pro Val Leu Glu Tyr Gly Gly Leu Thr
    50                  55                  60

Leu Tyr Gln Ser Arg Ala Ile Ala Arg His Ile Leu Arg Lys His Lys
65                  70                  75                  80

Pro Gly Leu Leu Gly Ala Gly Ser Leu Glu Glu Ser Ala Met Val Asp
                85                  90                  95

Val Trp Val Asp Val Asp Ala His His Leu Glu Pro Val Leu Lys Pro
            100                 105                 110

Ile Val Trp Asn Cys Ile Ile Asn Pro Phe Val Gly Arg Asp Val Asp
        115                 120                 125

Gln Gly Leu Val Asp Glu Ser Val Glu Lys Leu Lys Lys Leu Leu Glu
    130                 135                 140

Val Tyr Glu Ala Arg Leu Ser Ser Asn Lys Tyr Leu Ala Gly Asp Phe
145                 150                 155                 160

Val Ser Phe Ala Asp Leu Thr His Phe Ser Phe Met Arg Tyr Phe Met
                165                 170                 175

Ala Thr Glu His Ala Val Val Leu Asp Ala Tyr Pro His Val Lys Ala
            180                 185                 190

Trp Trp Lys Ala Leu Leu Ala Arg Pro Ser Val Lys Lys Val Ile Ala
        195                 200                 205

Gly Met Pro Pro Asp Phe Gly Phe Gly Ser Gly Arg Ile Pro
    210                 215                 220

<210> SEQ ID NO 42
<211> LENGTH: 213
<212> TYPE: PRT
<213> ORGANISM: Triticum aestivum

<400> SEQUENCE: 42

Met Ala Pro Ile Lys Leu Tyr Gly Met Met Leu Ser Ala Asn Val Thr
1               5                   10                  15

Arg Val Thr Thr Leu Leu Asn Glu Leu Gly Leu Glu Phe Asp Phe Val
            20                  25                  30

Asp Val Asp Leu Arg Thr Gly Ala His Lys His Pro Asp Phe Leu Lys
        35                  40                  45

Leu Asn Pro Phe Gly Gln Ile Pro Ala Leu Gln Asp Gly Asp Glu Val
    50                  55                  60

Val Phe Glu Ser Arg Ala Ile Asn Arg Tyr Ile Ala Thr Lys Tyr Gly
65                  70                  75                  80

```
Ala Ser Leu Leu Pro Thr Pro Ser Ala Lys Leu Glu Ala Trp Leu Glu
                85                  90                  95

Val Glu Ser His His Phe Tyr Pro Pro Ala Arg Thr Leu Val Tyr Glu
            100                 105                 110

Leu Val Ile Lys Pro Met Leu Gly Ala Pro Thr Asp Ala Ala Glu Val
        115                 120                 125

Asp Lys Asn Ala Ala Asp Leu Ala Lys Leu Leu Asp Val Tyr Glu Ala
    130                 135                 140

His Leu Ala Ala Gly Asn Lys Tyr Leu Ala Gly Asp Ala Phe Pro Leu
145                 150                 155                 160

Ala Asp Ala Asn His Met Ser Tyr Leu Phe Met Leu Thr Lys Ser Pro
                165                 170                 175

Lys Ala Asp Leu Val Ala Ser Arg Pro His Val Lys Ala Trp Trp Glu
            180                 185                 190

Glu Ile Ser Ala Arg Pro Ala Trp Ala Lys Thr Val Ala Ser Ile Pro
        195                 200                 205

Leu Pro Pro Ala Val
    210

<210> SEQ ID NO 43
<211> LENGTH: 218
<212> TYPE: PRT
<213> ORGANISM: Triticum aestivum

<400> SEQUENCE: 43

Met Ala Pro Val Lys Val Phe Gly Pro Ala Met Ser Thr Asn Val Ala
1               5                   10                  15

Arg Val Leu Val Cys Leu Glu Glu Val Gly Ala Glu Tyr Glu Val Val
            20                  25                  30

Asp Ile Asp Phe Lys Ala Met Glu His Lys Ser Pro Glu His Leu Val
        35                  40                  45

Arg Asn Pro Phe Gly Gln Ile Pro Ala Phe Gln Asp Gly Asp Leu Leu
    50                  55                  60

Leu Phe Glu Ser Arg Ala Ile Ala Arg Tyr Val Leu Arg Lys Tyr Lys
65                  70                  75                  80

Lys Asn Glu Val Asp Leu Leu Arg Glu Gly Asp Leu Lys Glu Ala Ala
                85                  90                  95

Met Val Asp Val Trp Thr Glu Val Asp Ala His Thr Tyr Asn Pro Ala
            100                 105                 110

Ile Ser Pro Ile Val Tyr Glu Cys Ser Ser Thr Ala His Ala Arg Leu
        115                 120                 125

Pro Thr Asn Gln Thr Val Val Asp Glu Ser Leu Glu Lys Leu Lys Asn
    130                 135                 140

Val Leu Glu Val Tyr Glu Ala Arg Leu Ser Lys His Asp Tyr Leu Ala
145                 150                 155                 160

Gly Asp Phe Val Ser Phe Ala Asp Leu Asn His Phe Pro Tyr Thr Phe
                165                 170                 175

Tyr Phe Met Ala Thr Pro His Ala Ala Leu Phe Asp Ser Tyr Pro His
            180                 185                 190

Val Lys Ala Trp Trp Glu Arg Ile Met Ala Arg Pro Ala Val Lys Lys
        195                 200                 205

Leu Ala Ala Gln Met Val Pro Lys Lys Pro
    210                 215
```

<210> SEQ ID NO 44
<211> LENGTH: 34
<212> TYPE: DNA
<213> ORGANISM: Artificial
<220> FEATURE:
<223> OTHER INFORMATION: Synthetic DNA

<400> SEQUENCE: 44
aaaaaagtcg acatggcggc gccggcggtg aagg                          34

<210> SEQ ID NO 45
<211> LENGTH: 32
<212> TYPE: DNA
<213> ORGANISM: Artificial
<220> FEATURE:
<223> OTHER INFORMATION: Synthetic DNA

<400> SEQUENCE: 45
aaaaaagcgg ccgctcactt ctctgccttc tt                            32

<210> SEQ ID NO 46
<211> LENGTH: 35
<212> TYPE: DNA
<213> ORGANISM: Artificial
<220> FEATURE:
<223> OTHER INFORMATION: Synthetic DNA

<400> SEQUENCE: 46
cacgggggac tctagatggc gccggcggtg aaggt                         35

<210> SEQ ID NO 47
<211> LENGTH: 35
<212> TYPE: DNA
<213> ORGANISM: Artificial
<220> FEATURE:
<223> OTHER INFORMATION: Synthetic DNA

<400> SEQUENCE: 47
gatcggggaa attcgctact ctgctttctt tccaa                         35

<210> SEQ ID NO 48
<211> LENGTH: 24
<212> TYPE: DNA
<213> ORGANISM: Artificial
<220> FEATURE:
<223> OTHER INFORMATION: Synthetic DNA

<400> SEQUENCE: 48
cgcctaaggt cactatcagc tagc                                     24

<210> SEQ ID NO 49
<211> LENGTH: 18
<212> TYPE: DNA
<213> ORGANISM: Artificial
<220> FEATURE:
<223> OTHER INFORMATION: Synthetic DNA

<400> SEQUENCE: 49
gaactccagc atgagatc                                            18

<210> SEQ ID NO 50
<211> LENGTH: 22
<212> TYPE: DNA
<213> ORGANISM: Artificial
<220> FEATURE:
<223> OTHER INFORMATION: Synthetic DNA -continued

```
<400> SEQUENCE: 50
agaggaccta acagaactcg cc                                              22

<210> SEQ ID NO 51
<211> LENGTH: 30
<212> TYPE: DNA
<213> ORGANISM: Artificial
<220> FEATURE:
<223> OTHER INFORMATION: Synthetic DNA

<400> SEQUENCE: 51
aaaaaactta agctactctg ctttctttcc                                      30
```